US012649786B2

(12) United States Patent
Kubo et al.

(10) Patent No.: US 12,649,786 B2
(45) Date of Patent: Jun. 9, 2026

---

(54) ANTI-HUMAN NR1 ANTIBODY DERIVATIVE

(71) Applicant: Arialys Therapeutics, Inc., La Jolla, CA (US)

(72) Inventors: Satoshi Kubo, Tokyo (JP); Atsuo Kanno, Tokyo (JP); Daisuke Yamajuku, Tokyo (JP); Takuya Kito, Tokyo (JP); Masashi Maeda, Tokyo (JP); Takuma Mihara, Tokyo (JP)

(73) Assignee: ARIALYS THERAPEUTICS, INC., La Jolla, CA (US)

( * ) Notice: Subject to any disclaimer, the term of this patent is extended or adjusted under 35 U.S.C. 154(b) by 540 days.

(21) Appl. No.: 18/056,635

(22) Filed: Nov. 17, 2022

(65) Prior Publication Data

US 2023/0220070 A1 Jul. 13, 2023

Related U.S. Application Data

(63) Continuation of application No. PCT/JP2021/019929, filed on May 26, 2021.

(30) Foreign Application Priority Data

May 27, 2020 (JP) ................................. 2020-092105

(51) Int. Cl.
  *C12N 15/13* (2006.01)
  *A61K 39/395* (2006.01)
  (Continued)

(52) U.S. Cl.
  CPC .............. *C07K 16/28* (2013.01); *A61P 25/00* (2018.01); *C12N 15/63* (2013.01);
  (Continued)

(58) Field of Classification Search
  None
  See application file for complete search history.

(56) References Cited

U.S. PATENT DOCUMENTS 4,676,980 A 6/1987 Segal et al.
4,816,567 A 3/1989 Cabilly et al.
(Continued)

FOREIGN PATENT DOCUMENTS

CN 114891091 A 8/2022
WO WO-1986002364 A1 4/1986
(Continued)

OTHER PUBLICATIONS

Lo et al., Effector-attenuating Substitutions That Maintain Antibody Stability and Reduce Toxicity in Mice *. The Journal of Biological Chemistry vol. 292, No. 9, pp. 3900-3908, Mar. 3, 2017 (Year: 2017).*

(Continued)

*Primary Examiner* — Aurora M Fontainhas
(74) *Attorney, Agent, or Firm* — WILSON SONSINI GOODRICH & ROSATI

(57) ABSTRACT

The present invention addresses the problem of providing a novel therapeutic agent for treating patients with anti NMDAR encephalitis. Patients with an anti NMDAR encephalitis have a pathogenic anti-human NR1 antibody that induces internalization of NMDAR on cell surface. As a result, NMDAR function is weakened in the patients' brain. The present inventors found that the one-armed anti-human NR1 antibody according to the present invention binds to NR1 competitively with the pathogenic anti-human NR1 antibody and inhibits the internalization of NMDAR by the pathogenic anti-human NR1 antibody to thereby exhibit therapeutic effect on anti NMDAR encephalitis. Accordingly, the present invention provides the a one-armed anti-human NR1 antibody, a polynucleotide encoding the antibody, an expression vector containing the polynucleotide, a host cell transformed by the expression vector, a method for producing the antibody, a pharmaceutical composition com-
(Continued)

Concentration [ng/ml]

prising the antibody, a use of the antibody in the manufacture of the pharmaceutical composition, and a method for treating anti NMDAR encephalitis using the antibody.

20 Claims, 6 Drawing Sheets

Specification includes a Sequence Listing.

(51) Int. Cl.
| | | |
|---|---|---|
| *A61P 25/00* | (2006.01) | |
| *C07K 16/28* | (2006.01) | |
| *C12N 15/63* | (2006.01) | |

(52) U.S. Cl.
CPC ...... *C07K 2317/24* (2013.01); *C07K 2317/52* (2013.01); *C07K 2317/565* (2013.01); *C07K 2317/70* (2013.01)

(56) References Cited

U.S. PATENT DOCUMENTS

| | | | |
|---|---|---|---|
| 4,946,778 | A | 8/1990 | Ladner et al. |
| 5,225,539 | A | 7/1993 | Winter |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 6,180,370 | B1 | 1/2001 | Queen et al. |
| 12,331,113 | B2 | 6/2025 | Kubo et al. |
| 2011/0200596 | A1 | 8/2011 | Huang et al. |
| 2018/0244802 | A1 * | 8/2018 | Pruess ..................... A61P 25/28 |
| 2023/0280340 | A1 | 9/2023 | Kornau et al. |

FOREIGN PATENT DOCUMENTS

| | | | | |
|---|---|---|---|---|
| WO | WO-9100360 | A1 | 1/1991 | |
| WO | WO-9220373 | A1 | 11/1992 | |
| WO | WO-1993008829 | A1 | 5/1993 | |
| WO | WO-9850431 | A2 | 11/1998 | |
| WO | WO-2014187879 | A2 | 11/2014 | |
| WO | WO-2017029299 | A1 | 2/2017 | |
| WO | WO-2019246071 | A1 * | 12/2019 | ............. A61K 38/00 |
| WO | WO-2020204977 | A1 | 10/2020 | |
| WO | WO-2021008890 | A1 | 1/2021 | |
| WO | WO-2021241616 | A1 | 12/2021 | |
| WO | WO-2024206667 | A1 | 10/2024 | |

OTHER PUBLICATIONS

Almagro et al. Humanization of antibodies. Front Biosci 13:1619-1633 (2008).
Atwell et al. Stable heterodimers from remodeling the domain interface of a homodimer using a phage display library. J. Mol. Biol., 270:26-35 (1997).
Baudino et al. Crucial role of aspartic acid at position 265 in the CH2 domain for murine IgG2a and IgG2b Fc-associated effector functions. J. Immunol., 181:6664-6669 (2008).
Bodrikov et al. Reggie-1 and reggie-2 (flotillins) participate in Rab11a-dependent cargo trafficking, spine synapse formation and LTP-related AMPA receptor (GluA1) surface exposure in mouse hippocampal neurons. Exp Neurol 289:31-45 (2017).
Bostian et al. In vitro synthesis of repressible yeast acid phosphatase: identification of multiple mRNAs and products. PNAS USA 77:4505 (1980).
Burmeister et al. Crystal structure of the complex of rat neonatal Fc receptor with Fc. Nature 372:379-383 (1994).
Clynes et al. Inhibitory Fc receptors modulate in vivo cytotoxicity against tumor targets. Nat Med. 6(4):443-6 (2000).

Dalmau et al. Autoimmune encephalitis update. Neuro Oncol. 16:771-778 (2014).
Dulbecco et al. Plaque production by the polyoma virus. Virology 67(8):396 (1959).
EAGLE. Amino acid metabolism in mammalian cell cultures. Science 130:432-437 (1950).
Fourie et al. Differential Changes in Postsynaptic Density Proteins in Postmortem Huntington's Disease and Parkinson's Disease Human Brains. J Neurodegener Dis 2014:938530 (2014).
Hughes et al. Cellular and synaptic mechanisms of anti-NMDA receptor encephalitis. J. Neurosci. 30(17):5866-5875 (2010).
Idusogie et al. Mapping of the C1q binding site on rituxan, a chimeric antibody with a human IgG1 Fc. J. Immunol., 164:4178-4184 (2000).
Kreye et al. Human cerebrospinal fluid monoclonal N-methyl-D-aspartate receptor autoantibodies are sufficient for encephalitis pathogenesis. Brain 139(pt 10):2641-2652 (2016).
Kurosawa et al. Rapid production of antigen-specific monoclonal antibodies from a variety of animals BMC Biol., 10:80 (2012).
Liu et al. Heterogeneity of monoclonal antibodies. J. Pharm. Sci., 97:2426-2447 (2008).
Lyubarskaya et al. Analysis of recombinant monoclonal antibody isoforms by electrospray ionization mass spectrometry as a strategy for streamlining characterization of recombinant monoclonal antibody charge heterogeneity. Anal. Biochem. 348(1):24-39 (2006).
Merchant et al. An efficient route to human bispecific IgG. Nature Biotechnology 16(7):677-81 (1998).
Merchant, et al. Monovalent antibody design and mechanism of action of onartuzumab, a MET antagonist with anti-tumor activity as a therapeutic agent. Proc Natl Acad Sci U S A. Aug. 6, 2013;110(32):E2987-96. doi: 10.1073/pnas.1302725110. Epub Jul. 23, 2013.
Mihara et al. A novel adenosine A(1) and A(2A) receptor antagonist ASP5854 ameliorates motor impairment in MPTP-treated marmosets: comparison with existing anti-Parkinson's disease drugs. Behav Brain Res., 194:152-161 (2008).
Moore et al. Culture of Normal Human Leukocytes. JAMA 199:519-524 (1967).
Morgan et al. Nutrition of animal cells in tissue culture; initial studies on a synthetic medium. Proc Soc Exp Biol Med 73:1-8 (1950).
PCT/JP2021/019929 International Search Report and Written Opinion dated Aug. 17, 2021 (with English Translation).
Sarmay et al., Mapping and comparison of the interaction sites on the Fc region of IgG responsible for triggering antibody dependent cellular cytotoxicity (ADCC) through different types of human Fc gamma receptor. Mol Immunol. 29(5):633-639 (1992).
Shi et al. Identification and therapeutic rescue of autophagosome and glutamate receptor defects in C9ORF72 and sporadic ALS neurons. JCI Insight 4(15):e127736 (2019).
Smith et al. Modification and secretion of human interleukin 2 produced in insect cells by a baculovirus expression vector. PNAS USA 82:8404 (1985).
Titulaer et al. Treatment and prognostic factors for long-term outcome in patients with anti-NMDA receptor encephalitis: an observational cohort study. Lancet Neurol., 12:157-165 (2013).
Traunmüller et al. Control of neuronal synapse specification by a highly dedicated alternative splicing program. Science 352(6288):982-986 (2016).
Tüzün et al. Evidence for antibody-mediated pathogenesis in anti-NMDAR encephalitis associated with ovarian teratoma. Acta Neuropathol. 118:737-743 (2009).
PCT/US2024/022024 International Search Report and Written Opinion dated Jun. 2, 2024.
Chiu et al. Optimization of an Anti-NMDA Receptor Autoantibody Diagnostic Bioassay. Front Neurol 9:661 (2018).
Contopoulos-Ioannidis et al. Toxoplasmosis and Schizophrenia: A Systematic Review and Meta-Analysis of Prevalence and Associations and Future Directions. Psychiatr Res Clin Pract. 4(2):48-60 (2022).

(56)          References Cited

OTHER PUBLICATIONS

Cullen et al. Influence of methodological and patient factors on serum NMDAR IgG antibody detection in psychotic disorders: a meta-analysis of cross-sectional and case-control studies. Lance Psychiatry 8(2):109-120 (2021).

Al-Lazikani, B. et al. Standard Conformations for the Canonical Structures of Immunoglobulins. Journal of Molecular Biology 273(4):927-948 (1997).

Altschul, Stephen F. et al. Basic Local Alignment Search Tool. Journal of Molecular Biology 215(3):403-410 (1990).

Berge, Stephen M. et al. Pharmaceutical Salts. Journal of Pharmaceutical Sciences 66(1):1-19 (1977).

Clackson, T. et al. Making Antibody Fragments using Phage Display Libraries. Nature 352(6336):624-628 (1991).

Honegger, Annemarie et al. Yet another numbering scheme for immunoglobulin variable domains: an automatic modeling and analysis tool. Journal of Molecular Biology 309(3):657-670 (2001).

Kabat, Elvin A et al. Sequences of Proteins of Immunological Interest, 5th Edition. U.S. Department of Health and Human Services NIH Publication No. 91-3242 (1991).

Karlin, S. et al. Applications and statistics for multiple high-scoring segments in molecular sequences. PNAS USA 90(12):5873-5877 (1993).

Karlin, Samuel et al. Methods for assessing the statistical significance of molecular sequence features by using general scoring schemes. PNAS USA 87(6):2264-2268 (1990).

Li, Feng et al. Cell Culture Processes for Monoclonal Antibody Production. MAbs. 2(5):466-477 (2010).

Cole, S.P.C. et al. The EBV-Hybridoma Technique and its Application to Human Lung Cancer. Monoclonal Antibodies and Cancer Therapy 27:77-96 (1985).

Fishwild, Dianne M. et al. High-avidity Human IgG kappa Monoclonal Antibodies From a Novel Strain of Minilocus Transgenic Mice. Nature Biotechnology 14(7):845-851 (1996).

Goding, James W. Chapter 3: Production of Monoclonal Antibodies. Production of monoclonal antibodies. In: Monoclonal Antibodies: Principles and Practice. London; New York: Academic Press pp. 59-103 (1986).

Kindt. Thomas J. et al. Chapter 4: Antibodies: Structure and Function, Sixth Edition. Kuby Immunology pp. 91 (2007).

Kohler, G. et al. Continuous Cultures of Fused Cells Secreting Antibody of Predefined Specificity. Nature 256(5517):495-497 (1975).

Kozbor, Danuta et al. The Production of Monoclonal Antibodies From Human Lymphocytes. Immunology Today 4(3):72-79 (1983).

Lefranc, Marie-Paule et al. IMGT Unique Numbering for Immunoglobulin and T Cell Receptor Variable Domains and Ig Superfamily V-like Domains. Developmental and Comparative Immunology 27(1):55-77 (2003).

Lonberg, N. et al. Antigen-Specific Human Antibodies From Mice Comprising Four Distinct Genetic Modifications. Nature 368(6474):856-859 (1994).

Lonberg, Nils et al. Human antibodies from transgenic mice. International reviews of immunology 13(1):65-93 (1995).

Maccallum, Robert M. et al. Antibody-Antigen Interactions: Contact Analysis and Binding Site Topography. Journal of Molecular Biology 262(5):732-745 (1996).

Marks, James D. et al. By-passing immunization: building high affinity human antibodies by chain shuffling. Biotechnology 10(7):779-783 (1992).

Mccafferty, John et al. Phage Antibodies: Filamentous Phage Displaying Antibody Variable Domains. Nature 348(6301):552-554 (1990).

Morrison, S. Immunology. Success in specification. Nature 368(6474):812-813 (1994).

Neuberger, Michael. Generating High-avidity Human Mabs in Mice. Nature Biotechnology 14(7):826 (1996).

Portolano, Stefano et al. Lack of promiscuity in autoantigen-specific H and L chain combinations as revealed by human H and L chain "roulette". Journal of immunology 150(3):880-887 (1993).

Suresh, M. R. et al. Bispecific Monoclonal Antibodies From Hybrid Hybridomas. Methods in Enzymology 121:210-228 (1986).

Traunecker, Andr et al. Bispecific Single Chain Molecules (Janusins) Target Cytotoxic Lymphocytes on HIV Infected Cells. The EMBO Journal 10(12):3655-3659 (1991).

Whitelegg, Nicholas R. et al. WAM: An Improved Algorithm for Modelling Antibodies on the WEB. Protein Engineering 13(12):819-824 (2000).

* cited by examiner

Concentration [ng/ml]

Concentration [ng/ml]

ABN-2 Concentration [ng/ml]

P003-102 10 $\mu$ g/hr
Continuous intracerebroventricular
administration (28 days)

Control antibody or, ABN-2
Continuous intracerebroventricular
administration 10 $\mu$ g/hr (14 days)

ANTI-HUMAN NR1 ANTIBODY DERIVATIVE

CROSS-REFERENCE TO RELATED APPLICATIONS

This application is a continuation of International Application No. PCT/JP2021/019929, filed May 26, 2021, which claims the benefit of Japanese Application No. JP2020092105, filed May 27, 2020, each of which are incorporated herein by reference in their entirety.

SEQUENCE LISTING

The instant application contains a Sequence Listing which has been submitted electronically in XML format and is hereby incorporated by reference in its entirety. Said XML file, created on Nov. 17, 2022, is named 62548-703_301_SL.xml and is 88,364 bytes in size.

TECHNICAL FIELD

The invention relates to an anti-human NR1 antibody derivative useful as an active ingredient in pharmaceutical compositions.

BACKGROUND OF THE INVENTION

The relation between an autoantibody to a nerve cell and disease has recently become clear. An autoantibody to a nerve cell is called an anti-neuronal antibody and it is indicated to become the etiology of neurological diseases such as autoimmune encephalitis. In recent years, new anti-neuronal antibodies against cell surface and synaptic antigens has been identified one after another. Many of them are antibodies to a receptor or a channel expressed on a nerve cell or their associated molecules (Journal of Clinical and Experimental Medicine (IGAKU NO AYUMI), 2015, Vol. 25, No. 5, pp. 497-503/Neuro-oncol. 2014, Vol. 16, pp. 771-778).

In 2007, Dalmau et al. found that in encephalitis with a unique clinical course complicated by ovarian teratoma, an autoantibody to a cell surface antigen, which exists in a patient's blood and spinal fluid, was the antibody to a NR1 (also known as GluN1) subunit of the NMDA (N-methyl-D-aspartate) receptor (hereinafter, referred to as "NMDAR"), and named this encephalitis "anti-NMDAR encephalitis." Among autoimmune encephalitis, anti-NMDAR encephalitis is the one of the most common autoimmune encephalitides, and its clinical presentation is well defined. In patients with anti-NMDAR encephalitis, typically psychiatric symptoms develop first, followed by a variety of neurologic symptoms, including memory impairment, speech impairment, disorientation, seizures, autonomic symptoms, central hypoventilation and involuntary movements. The pathogenesis of anti-NMDAR encephalitis progresses quickly, and in some cases the course of the disease is severe, requiring intensive treatment within weeks after the discovery of the initial symptoms, with treatment lasting from several months to over a year. The anti-NR1 antibody titer in a patient's spinal fluid reflects the course of the disease. Anti-NMDAR encephalitis occurs rarely in children, the elderly, and men, but is more common in young women. It has been reported that many women who develop the disease are complicated by ovarian teratomas (Lancet Neurol., 2013, Vol. 12, pp. 157-165).

Pathologically, it has been reported that IgG deposition and decrease in NMDAR expression have been observed in the brain of a patient with anti-NMDAR encephalitis (Acta Neuropathol., 2009, Vol. 118, pp. 737-743, Non-Patent Document 1). On the other hand, since no deposition of cytotoxic T cell or complement has been observed in the patient's brain (Acta Neuropathol., 2009, Vol. 118, pp. 737-743), it is assumed that NR1 antibodies alone influence a pathological formation. In vitro experiments has reported that a patient-derived NR1 antibody cross-links to NMDAR and internalizes NMDAR to reduce NMDARs in the post-synaptic membrane (Non-Patent Document 1). Furthermore, since the symptoms of anti-NMDAR encephalitis are similar to those observed in healthy subjects when administered with NMDAR antagonist (ketamine and phencyclidine), it is considered that the internalization of NMDAR by an NR1 antibody in a patient and the consequent reduction of NMDAR clusters in the postsynaptic membrane lead to a functional decline of NMDARs, causing anti-NMDAR encephalitis symptoms.

An early tumor resection and immunotherapy are recommended in tumor-associated cases of anti-NMDAR encephalitis. As an immunotherapy, steroid pulse therapy, plasma exchange, and immunoglobulin therapy are used. In refractory cases, a cyclophosphamide pulse therapy or rituximab, which is an anti-CD20 antibody, are administered. However, not all patients have good prognosis because of the severe and prolonged course of the disease. It has been reported that full or nearly full recovery is only 75% while 25% remain severely disabled or die (Lancet Neurol., 2008, Vol. 7, pp. 1091-1098).

Current treatment for anti-NMDAR encephalitis does not specifically control or remove an autoantibody that causes the pathological condition.

NMDAR is a type of glutamate receptor, expressed mainly in the central nervous system, and involved in memory and learning. NMDAR is an ion channel-coupled receptor that allows cations such as sodium, potassium, and calcium ions to permeate by binding to glutamic acid, which is ligand. NMDAR has four subunits that consists of two sets of heterodimers, NR1 and NR2. There are four types of NR2: NR2A, NR2B, NR2C, and NR2D. There is a binding site for glutamic acid in the NR2 subunit.

As anti-NR1 monoclonal antibodies, M68 (Non-Patent Document 2), MAB363 (Non-Patent Document 3), R1JHL (Non-Patent Document 4), and D65B8 (Non-Patent Document 5) have been reported. In addition, a monoclonal antibody which binds to an N-terminal site of human NR1 and inhibits an interaction with t-PA has been reported (Patent document 1). Furthermore, several anti-NR1 monoclonal antibodies derived from anti-NMDAR encephalitis patients have been identified (Non-Patent Document 6, Patent Document 2). An isolated anti-NMDAR encephalitis patient derived anti-NR1 antibody, in vitro, reduced NMDAR clustering and suppressed NMDAR function in primary neurons derived from mouse hippocampus (Non-Patent Document 6).

On the other hand, no anti-human NR1 antibody or its derivative has been reported to show therapeutic effect in patients with anti-NMDAR encephalitis.

PRIOR-ART DOCUMENTS

Patent Documents

Patent Document 1: WO2014/187879
Patent Document 2: WO2017/029299

Non-Patent Document

Non-Patent Document 1: [Journal of Neuroscience, (J. Neurosci.)], (USA), 2010; 30(17): 5866-5875

Non-Patent Document 2: [Science (Science)], (USA), 2016; 352 (6288): 982-986

Non-Patent Document 3: [Journal of neurodegenerative diseases (J. Neurodegener. Dis.)], (UK), 2014; Article ID: 938530

Non-Patent Document 4: [JCI Insight (JCI Insight)], (USA), 2019; 4(15): e127736

Non-Patent Document 5: [Experimental Neurology (Exp. Neurol.)], (USA), 2017; 289: 31-45

Non-Patent Document 6: [Brain (Brain)], (UK), 2016; 139(10): 2641-2652

SUMMARY OF THE INVENTION

Problems to be Solved by the Invention

The invention addresses the problem of providing a novel therapeutic agent for treating patients with anti-NMDAR encephalitis.

Means for Solving the Problem

The inventors have done a number of studies in producing a novel therapeutic agent to treat a patient with anti-NMDAR encephalitis. First, the inventors produced a one-armed anti-human NR1 antibody from the sequence information of an anti-human NR1 antibody clone derived from an anti-NMDAR encephalitis patient with high binding activity to NMDAR, and found that the one-armed anti-human NR1 antibody, when binding to human NMDAR in vitro, restored the cell surface expression level and function of human NMDAR caused by a patient-derived pathogenic NR1 antibody (Examples 1-4). Furthermore, based on these findings, the inventors have also produced multiple one-armed anti-human NR1 antibodies exhibiting a higher binding affinity than a pathogenic NR1 antibody, which significantly restored the cell surface expression level and function of NMDAR caused by a pathogenic anti-human NR11 antibody (Examples 5-10). Furthermore, the inventors have found that the newly obtained one-arm anti-human NR1 antibody significantly improved the symptoms of an anti-NMDAR encephalitis animal model compared to the control antibody (Example 12). Accordingly, the inventors have completed the present invention.

According to the present invention, the following inventions are provided as medically and industrially useful substances or methods, for example:

[1]

A one-armed anti-human NR1 antibody selected from any of the following (1) to (5):

(1) a one-armed anti-human NR1 antibody comprising a heavy chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, and a light chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4;

(2) a one-armed anti-human NR1 antibody comprising a heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, and a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8;

(3) a one-armed anti-human NR1 antibody comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, and a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12;

(4) a one-armed anti-human NR1 antibody comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, and a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16;

(5) a one-armed anti-human NR1 antibody comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, and a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20.

[2]

The one-armed anti-human NR1 antibody of [1] selected from any of the following (1) to (5):

(1) a one-armed anti-human NR1 antibody comprising a heavy chain variable region consisting of the amino acid sequence shown in SEQ ID NO: 2, and a light

5 chain variable region consisting of the amino acid sequence shown in SEQ ID NO: 4;

(2) a one-armed anti-human NR1 antibody comprising a heavy chain variable region consisting of the amino acid sequence shown in SEQ ID NO: 6, and a light chain variable region consisting of the amino acid sequence shown in SEQ ID NO: 8;

(3) a one-armed anti-human NR1 antibody comprising a heavy chain variable region consisting of the amino acid sequence shown in SEQ ID NO: 10, and a light chain variable region consisting of the amino acid sequence shown in SEQ ID NO: 12;

(4) a one-armed anti-human NR1 antibody comprising a heavy chain variable region consisting of the amino acid sequence shown in SEQ ID NO: 14, and a light chain variable region consisting of the amino acid sequence shown in SEQ ID NO: 16;

(5) a one-armed anti-human NR1 antibody comprising a heavy chain variable region consisting of the amino acid sequence shown in SEQ ID NO: 18, and a light chain variable region consisting of the amino acid sequence shown in SEQ ID NO: 20.

[3]
The one-armed anti-human NR1 antibody of [1] selected from any of the following (1) to (5):

(1) a one-armed anti-human NR1 antibody comprising a heavy chain comprising a heavy chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, a light chain comprising a light chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4, as well as an Fc polypeptide;

(2) a one-armed anti-human NR1 antibody comprising a heavy chain comprising heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, a light chain comprising a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8, as well as an Fc polypeptide;

(3) a one-armed anti-human NR1 antibody comprising a heavy chain comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, a light chain comprising a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12, as well as an Fc polypeptide;

(4) a one-armed anti-human NR1 antibody comprising a heavy chain comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, a light chain comprising a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16, as well as an Fc polypeptide;

(5) a one-armed anti-human NR1 antibody comprising a heavy chain comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, a light chain comprising a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20; and an Fc polypeptide.

[4]
The one-armed anti-human NR1 antibody of [3] selected from any of the following (1) to (5):

(1) a one-armed anti-human NR1 antibody comprising a heavy chain comprising a heavy chain variable region consisting of the amino acid sequence shown in SEQ ID NO: 2, a light chain comprising a light chain variable region consisting of the amino acid sequence shown in SEQ ID NO: 4, and an Fc polypeptide;

(2) a one-armed anti-human NR1 antibody comprising a heavy chain comprising a heavy chain variable region consisting of the amino acid sequence shown in SEQ ID NO: 6, a light chain comprising a light chain variable region consisting of the amino acid sequence shown in SEQ ID NO: 8, and an Fc polypeptide;

(3) a one-armed anti-human NR1 antibody comprising a heavy chain comprising a heavy chain variable region consisting of the amino acid sequence shown in SEQ ID NO: 10, a light chain comprising a light chain variable region consisting of the amino acid sequence shown in SEQ ID NO: 12, and an Fc polypeptide;

(4) a one-armed anti-human NR1 antibody comprising a heavy chain comprising a heavy chain variable region consisting of the amino acid sequence shown in SEQ ID NO: 14, a light chain comprising a light chain variable region consisting of the amino acid sequence shown in SEQ ID NO: 16, and an Fc polypeptide;

(5) a one-armed anti-human NRA antibody comprising a heavy chain comprising a heavy chain variable region consisting of the amino acid sequence shown in SEQ ID NO: 18, a light chain comprising a light chain variable region consisting of the amino acid sequence shown in SEQ ID NO: 20, and an Fc polypeptide.

[5]
The one-armed anti-human NR1 antibody of any one of [1] to [4] comprising an Fc region comprising a LALA mutation (L234A and L235A).

[6]
The one-armed anti-human NR1 antibody of any one of [1] to [4] comprising an Fc region comprising a Knobs into holes mutation.

[7]
The one-armed anti-human NR1 antibody of any one of [1] to [4] comprising an Fc region comprising a LALA mutation (L234A and L235A) and a Knobs into holes mutation.

[8]
The one-armed anti-human NR1 antibody of [6] or [7], wherein the Knobs into holes mutation is a T366W mutation in one Fc polypeptide forming an Fc region, and T366S, L368A and Y407V mutation in another Fc polypeptide forming an Fc region.

[9]
The one-armed anti-human NR1 antibody of any one of [1] to [8], wherein the one-armed anti-human NR1 antibody is a human antibody or a humanized antibody.

[10]
A one-armed anti-human NR1 antibody comprising a heavy chain consisting of the amino acid sequence shown in SEQ ID NO: 22, a light chain consisting of the amino acid sequence shown in SEQ ID NO: 24, and an Fc polypeptide consisting of the amino acid sequence shown in SEQ ID NO: 42.

[11]
A one-armed anti-human NR1 antibody comprising a heavy chain consisting of the amino acid sequence shown in SEQ ID NO: 26, a light chain consisting of the amino acid sequence shown in SEQ ID NO: 28, and an Fc polypeptide consisting of the amino acid sequence shown in SEQ ID NO: 42.

[12]
A one-armed anti-human NR1 antibody comprising a heavy chain consisting of the amino acid sequence shown in SEQ ID NO: 30, a light chain consisting of the amino acid sequence shown in SEQ ID NO: 32, and an Fc polypeptide consisting of the amino acid sequence shown in SEQ ID NO: 42.

[13]
A one-armed anti-human NR1 antibody comprising a heavy chain consisting of the amino acid sequence shown in SEQ ID NO: 34, a light chain consisting of the amino acid sequence shown in SEQ ID NO: 36, and an Fc polypeptide consisting of the amino acid sequence shown in SEQ ID NO: 42.

[14]
A one-armed anti-human NR1 antibody comprising a heavy chain consisting of the amino acid sequence shown in SEQ ID NO: 38, a light chain consisting of the amino acid sequence shown in SEQ ID NO: 40, and an Fc polypeptide consisting of the amino acid sequence shown in SEQ ID NO: 42.

[15]
A one-armed anti-human NR1 antibody, wherein the one-armed anti-human NR1 antibody binds to human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR cell internalization by a pathogenic anti-human NR1 antibody derived from an anti-NMDAR encephalitis patient.

[16]
The one-armed anti-human NR1 antibody of any one of [1] to [15], wherein the one-armed anti-human NR1 antibody is post-translationally modified.

[17]
The one-armed anti-human NR1 antibody of [16], wherein the post-translational modification is pyroglutamylation of the N-terminal heavy chain variable region and/or deletion of the C-terminal heavy chain lysine.

[18]
A polynucleotide comprising the nucleotide sequence set forth in (a) and/or (b) below:
    (a) a nucleotide sequence encoding the heavy chain variable region of the one-armed anti-human NR1 antibody of any of (2) to (5) of [1] and (2) to (5) of [2];
    (b) a nucleotide sequence encoding the light chain variable region of the one-armed anti-human NR1 antibody of any of (2) to (5) of [1] and (2) to (5) of [2].

[19]
A polynucleotide comprising the nucleotide sequence set forth in (a) and/or (b) below:
    (a) a nucleotide sequence encoding the heavy chain of the one-armed anti-human NR1 antibody of any of (2) to (5) of [3] and (2) to (5) of [4];
    (b) a nucleotide sequence encoding the light chain of the one-armed anti-human NR1 antibody of any of (2) to (5) of [3] and (2) to (5) of [4].

[20]
A polynucleotide comprising the nucleotide sequence set forth in (a) and/or (b) below:
    (a) a nucleotide sequence encoding the heavy chain consisting of the amino acid sequence shown in SEQ ID NO: 26;
    (b) a nucleotide sequence encoding the light chain consisting of the amino acid sequence shown in SEQ ID NO: 28.

[21]
A polynucleotide comprising the nucleotide sequence set forth in (a) and/or (b) below:
    (a) a nucleotide sequence encoding the heavy chain consisting of the amino acid sequence shown in SEQ ID NO: 30;
    (b) a nucleotide sequence encoding the light chain consisting of the amino acid sequence shown in SEQ ID NO: 32.

[22]
A polynucleotide comprising the nucleotide sequence set forth in (a) and/or (b) below:
    (a) a nucleotide sequence encoding the heavy chain consisting of the amino acid sequence shown in SEQ ID NO: 34;
    (b) a nucleotide sequence encoding the light chain consisting of the amino acid sequence shown in SEQ ID NO: 36.

[23]
A polynucleotide comprising the nucleotide sequence set forth in (a) and/or (b) below:
    (a) a nucleotide sequence encoding the heavy chain consisting of the amino acid sequence shown in SEQ ID NO: 38;
    (b) a nucleotide sequence encoding the light chain consisting of the amino acid sequence shown in SEQ ID NO: 40.

9

[24]
A polynucleotide comprising the nucleotide sequence set forth in (a) and/or (b) below:
   (a) a nucleotide sequence encoding the heavy chain of the one-armed anti-human NR1 antibody of [15];
   (b) a nucleotide sequence encoding the light chain of the one-armed anti-human NR1 antibody of [15].

[25]
An expression vector comprising a polynucleotide comprising the nucleotide sequence set forth in (a) and/or (b) below:
   (a) a polynucleotide comprising a nucleotide sequence encoding a heavy chain variable region of the one-armed anti-human NR1 antibody set forth in any of (2) to (5) of [1] and (2) to (5) of [2];
   (b) a polynucleotide comprising a nucleotide sequence encoding the light chain variable region of the one-armed anti-human NR1 antibody set forth in any of (2) to (5) of [1] and (2) to (5) of [2].

[26]
An expression vector comprising a polynucleotide comprising the nucleotide sequence set forth in (a) and/or (b) below:
   (a) a polynucleotide comprising a nucleotide sequence encoding a heavy chain of the one-armed anti-human NR1 antibody set forth in any of (2) to (5) of [3] and (2) to (5) of [4];
   (b) a polynucleotide comprising a nucleotide sequence encoding a light chain of the one-armed anti-human NR1 antibody set forth in any of (2) to (5) of [3] and (2) to (5) of [4].

[27]
The expression vector of [25] or [26], further comprising a polynucleotide comprising a nucleotide sequence encoding an Fc polypeptide.

[28]
An expression vector comprising a polynucleotide set forth in (a) and/or (b) below, as well as a polynucleotide comprising a nucleotide sequence encoding an Fc polypeptide consisting of the amino acid sequence shown in SEQ ID NO: 42:
   (a) a polynucleotide comprising a nucleotide sequence encoding a heavy chain consisting of the amino acid sequence shown in SEQ ID NO: 22;
   (b) a polynucleotide comprising a nucleotide sequence encoding a light chain consisting of the amino acid sequence shown in SEQ ID NO: 24.

[29]
An expression vector comprising the polynucleotide set forth in (a) and/or (b) below:
   (a) a polynucleotide comprising a nucleotide sequence encoding a heavy chain consisting of the amino acid sequence shown in SEQ ID NO: 26;
   (b) a polynucleotide comprising a nucleotide sequence encoding a light chain consisting of the amino acid sequence shown in SEQ ID NO: 28.

[30]
An expression vector comprising the polynucleotide set forth in (a) and/or (b) below:
   (a) a polynucleotide comprising a nucleotide sequence encoding a heavy chain consisting of the amino acid sequence shown in SEQ ID NO: 30;
   (b) a polynucleotide comprising a nucleotide sequence encoding a light chain consisting of the amino acid sequence shown in SEQ ID NO: 32.

[31]
An expression vector comprising the polynucleotide set forth in (a) and/or (b) below:

(a) a polynucleotide comprising a nucleotide sequence encoding a heavy chain consisting of the amino acid sequence shown in SEQ ID NO: 34;
   (b) a polynucleotide comprising a nucleotide sequence encoding a light chain consisting of the amino acid sequence shown in SEQ ID NO: 36.

[32]
An expression vector comprising the polynucleotide set forth in (a) and/or (b) below:
   (a) a polynucleotide comprising a nucleotide sequence encoding a heavy chain consisting of the amino acid sequence shown in SEQ ID NO: 38;
   (b) a polynucleotide comprising a nucleotide sequence encoding a light chain consisting of the amino acid sequence shown in SEQ ID NO: 40.

[33]
The expression vector of any one of [29] to [32], further comprising a polynucleotide comprising a nucleotide sequence encoding an Fc polypeptide consisting of the amino acid sequence shown in SEQ ID NO: 42.

[34]
An expression vector comprising the polynucleotide set forth in (a) to (f) below comprising a nucleotide sequence:
   (a) a polynucleotide comprising a nucleotide sequence encoding a heavy chain of the one-armed anti-human NR1 antibody of [15];
   (b) a polynucleotide comprising a nucleotide sequence encoding a light chain of the one-armed anti-human NR1 antibody of [15];
   (c) a polynucleotide comprising a nucleotide sequence encoding a heavy chain of the one-armed anti-human NR1 antibody of [15], and a polynucleotide comprising a nucleotide sequence encoding a light chain of the antibody;
   (d) a polynucleotide comprising a nucleotide sequence encoding a heavy chain of the one-armed anti-human NR1 antibody of [15], and a polynucleotide comprising a nucleotide sequence encoding an Fc polypeptide of the antibody;
   (e) a polynucleotide comprising a nucleotide sequence encoding a light chain of the one-armed anti-human NR1 antibody of [15], and a polynucleotide comprising a nucleotide sequence encoding an Fc polypeptide of the antibody;
   (f) a polynucleotide comprising a nucleotide sequence encoding a heavy chain of the one-armed anti-human NR1 antibody of [15], a polynucleotide comprising a nucleotide sequence encoding a light chain of the antibody, and a polynucleotide comprising a nucleotide sequence encoding an Fc polypeptide of the antibody.

[35]
A host cell transformed with an expression vector or vectors selected from (a) to (d) below:
   (a) an expression vector comprising a polynucleotide comprising a nucleotide sequence encoding a heavy chain variable region of the one-armed anti-human NR1 antibody set forth in any of (2) to (5) of [1] and (2) to (5) of [2];
   (b) an expression vector comprising a polynucleotide comprising a nucleotide sequence encoding a light chain variable region of the one-armed anti-human NR1 antibody set forth in any of (2) to (5) of [1] and (2) to (5) of [2];
   (c) an expression vector comprising a polynucleotide comprising a nucleotide sequence encoding a heavy chain variable region of the one-armed anti-human NR1 antibody set forth in any of (2) to (5) of [1] and (2) to (5) of [2], and a polynucleotide comprising a nucleotide sequence encoding a light chain variable region of the antibody;

(d) an expression vector comprising a polynucleotide comprising a nucleotide sequence encoding a heavy chain variable region of the one-armed anti-human NR1 antibody set forth in any of (2) to (5) of [1] and (2) to (5) of [2], and an expression vector comprising a polynucleotide comprising an nucleotide sequence encoding a light chain variable region of the antibody.

[36]

A host cell transformed with an expression vector or vectors selected from (a) to (d) below:

(a) an expression vector comprising a polynucleotide comprising a nucleotide sequence encoding a heavy chain of the one-armed anti-human NR1 antibody set forth in any of (2) to (5) of [3] and (2) to (5) of [4];

(b) an expression vector comprising a polynucleotide comprising a nucleotide sequence encoding a light chain of the one-armed anti-human NR1 antibody set forth in any of (2) to (5) of [3] and (2) to (5) of [4];

(c) an expression vector comprising a polynucleotide comprising a nucleotide sequence encoding a heavy chain of the one-armed anti-human NR1 antibody set forth in any of (2) to (5) of [3] and (2) to (5) of [4], and a polynucleotide comprising an nucleotide sequence encoding a light chain of the antibody;

(d) an expression vector comprising a polynucleotide comprising a nucleotide sequence encoding a heavy chain of the one-armed anti-human NR1 antibody set forth in any of (2) to (5) of [3] and (2) to (5) of [4], and an expression vector comprising a polynucleotide comprising a nucleotide sequence encoding a light chain of the antibody.

[37]

A host cell transformed with an expression vector or vectors selected from (a) to (i) below:

(a) an expression vector comprising a polynucleotide comprising a nucleotide sequence encoding a heavy chain of the one-armed anti-human NR1 antibody set forth in any of (1) to (5) of [3] and (1) to (5) of [4] and an expression vector comprising a polynucleotide comprising a nucleotide sequence encoding an Fc polypeptide of the antibody;

(b) an expression vector comprising a polynucleotide comprising a nucleotide sequence encoding a light chain of the one-armed anti-human NR1 antibody set forth in any of (1) to (5) of [3] and (1) to (5) of [4] and an expression vector comprising a polynucleotide comprising a nucleotide sequence encoding an Fc polypeptide of the antibody;

(c) an expression vector comprising a polynucleotide comprising a nucleotide sequence encoding a heavy chain of the one-armed anti-human NR1 antibody set forth in any of (1) to (5) of [3] and (1) to (5) of [4] and a polynucleotide comprising a nucleotide sequence encoding a light chain of the antibody, as well as an expression vector comprising a polynucleotide comprising a nucleotide sequence encoding an Fc polypeptide of the antibody;

(d) an expression vector comprising a polynucleotide comprising a nucleotide sequence encoding a heavy chain of the one-armed anti-human NR1 antibody set forth in any of (1) to (5) of [3] and (1) to (5) of [4], an expression vector comprising a polynucleotide comprising a nucleotide sequence encoding a light chain of the antibody, and an expression vector comprising a polynucleotide comprising a nucleotide sequence encoding an Fc polypeptide of the antibody;

(e) an expression vector comprising a polynucleotide comprising a nucleotide sequence encoding a heavy chain of the one-armed anti-human NR1 antibody set forth in any of (1) to (5) of [3] and (1) to (5) of [4] and a polynucleotide comprising a nucleotide sequence encoding an Fc polypeptide of the antibody;

(f) an expression vector comprising a polynucleotide comprising a nucleotide sequence encoding a light chain of the one-armed anti-human NR1 antibody set forth in any of (1) to (5) of [3] and (1) to (5) of [4], as well as a polynucleotide comprising a nucleotide sequence encoding an Fc polypeptide of the antibody;

(g) an expression vector comprising a polynucleotide comprising a nucleotide sequence encoding a heavy chain of the one-armed anti-human NR1 antibody set forth in any of (1) to (5) of [3] and (1) to (5) of [4] and a polynucleotide comprising a nucleotide sequence encoding an Fc polypeptide of the antibody, as well as an expression vector comprising a polynucleotide comprising a nucleotide sequence encoding a light chain of the antibody;

(h) an expression vector comprising a polynucleotide comprising a nucleotide sequence encoding a heavy chain of the one-armed anti-human NR1 antibody set forth in any of (1) to (5) of [3] and (1) to (5) of [4], as well as an expression vector comprising a polynucleotide comprising a nucleotide sequence encoding a light chain of the antibody and a polynucleotide comprising a nucleotide sequence encoding an Fc polypeptide of the antibody;

(i) an expression vector comprising a polynucleotide comprising a nucleotide sequence encoding a heavy chain of the one-armed anti-human NR1 antibody set forth in any of (1) to (5) of [3] and (1) to (5) of [4], a polynucleotide comprising a nucleotide sequence encoding a light chain of the antibody, and a polynucleotide comprising a nucleotide sequence encoding an Fc polypeptide of the antibody.

[38]

A host cell transformed with an expression vector or vectors selected from (a) to (i) below:

(a) an expression vector comprising a polynucleotide comprising a nucleotide sequence encoding a heavy chain consisting of the amino acid sequence shown in SEQ ID NO: 22, and an expression vector comprising a polynucleotide comprising a nucleotide sequence encoding an Fc polypeptide consisting of the amino acid sequence shown in SEQ ID NO: 42;

(b) an expression vector comprising a polynucleotide comprising a nucleotide sequence encoding a heavy chain consisting of the amino acid sequence shown in SEQ ID NO: 22 and a polynucleotide comprising a nucleotide sequence encoding an Fc polypeptide consisting of the amino acid sequence shown in SEQ ID NO: 42;

(c) an expression vector comprising a polynucleotide comprising a nucleotide sequence encoding a light chain consisting of the amino acid sequence shown in SEQ ID NO: 24, as well as an expression vector comprising a polynucleotide comprising a nucleotide sequence encoding an Fc polypeptide consisting of the amino acid sequence shown in SEQ ID NO: 42;

(d) an expression vector comprising a polynucleotide comprising a nucleotide sequence encoding a light chain consisting of the amino acid sequence shown in SEQ ID NO: 24 and a polynucleotide comprising a nucleotide sequence encoding an Fc polypeptide consisting of the amino acid sequence shown in SEQ ID NO: 42;

(e) an expression vector comprising a polynucleotide comprising a nucleotide sequence encoding a heavy chain consisting of the amino acid sequence shown in SEQ ID NO: 22 and a polynucleotide comprising a nucleotide sequence encoding a light chain consisting of the amino acid sequence shown in SEQ ID NO: 24, as well as an expression vector comprising a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a heavy chain consisting of the amino acid sequence shown in SEQ ID NO: 22 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 24;

(g) an expression vector comprising a polynucleotide comprising a nucleotide sequence encoding a heavy chain consisting of the amino acid sequence shown in SEQ ID NO: 22, as well as an expression vector comprising a polynucleotide comprising a nucleotide sequence encoding a light chain consisting of the amino acid sequence shown in SEQ ID NO: 24 and a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a heavy chain consisting of the amino acid sequence shown in SEQ ID NO: 22, an expression vector comprising a polynucleotide comprising a nucleotide sequence encoding a light chain consisting of the amino acid sequence shown in SEQ ID NO: 24, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 22, a polynucleotide comprising a nucleotide sequence encoding a light chain consisting of the amino acid sequence shown in SEQ ID NO: 24, and a polynucleotide comprising a nucleotide sequence encoding an Fc polypeptide consisting of the amino acid sequence shown in SEQ ID NO: 42.

[39]
A host cell transformed with an expression vector or vectors selected from (a) to (m) below:

(a) an expression vector comprising a polynucleotide comprising a nucleotide sequence encoding a heavy chain consisting of the amino acid sequence shown in SEQ ID NO: 26;

(b) an expression vector comprising a polynucleotide comprising a nucleotide sequence encoding a light chain consisting of the amino acid sequence shown in SEQ ID NO: 28; (c) an expression vector comprising a polynucleotide comprising a nucleotide sequence encoding a heavy chain consisting of the amino acid sequence shown in SEQ ID NO: 26 and a polynucleotide comprising a nucleotide sequence encoding a light chain consisting of the amino acid sequence shown in SEQ ID NO: 28;

(d) an expression vector comprising a polynucleotide comprising a nucleotide sequence encoding a heavy chain consisting of the amino acid sequence shown in SEQ ID NO: 26, and an expression vector comprising a polynucleotide comprising a nucleotide sequence encoding a light chain consisting of the amino acid sequence shown in SEQ ID NO: 28;

(e) an expression vector comprising a polynucleotide comprising a nucleotide sequence encoding a heavy chain consisting of the amino acid sequence shown in SEQ ID NO: 26, and a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a light chain consisting of the amino acid sequence shown in SEQ ID NO: 28 and a polynucleotide comprising a nucleotide sequence encoding an Fc polypeptide consisting of the amino acid sequence shown in SEQ ID NO: 42;

(g) an expression vector comprising a polynucleotide comprising a nucleotide sequence encoding a heavy chain consisting of the amino acid sequence shown in SEQ ID NO: 26, and an expression vector comprising a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a light chain consisting of the amino acid sequence shown in SEQ ID NO: 28, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 26 and a polynucleotide comprising a nucleotide sequence encoding a light chain consisting of the amino acid sequence shown in SEQ ID NO: 28, as well as an expression vector comprising a polynucleotide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 26 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 28;

(k) an expression vector comprising a polynucleotide comprising a nucleotide sequence encoding a heavy chain consisting of the amino acid sequence shown in SEQ ID NO: 26, as well as an expression vector comprising a polynucleotide comprising a nucleotide sequence encoding a light chain consisting of the amino acid sequence shown in SEQ ID NO: 28 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 26, an expression vector comprising a polynucleotide comprising a nucleotide sequence encoding a light chain consisting of the amino acid sequence shown in SEQ ID NO: 28, and an expression vector comprising polynucleotide comprising a nucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 26, a polynucleotide comprising a nucleotide sequence encoding a light chain consisting of the amino acid sequence shown in SEQ ID NO: 28, and a polynucleotide comprising a nucleotide sequence encoding an Fc polypeptide consisting of the amino acid sequence shown in SEQ ID NO: 42.

[40]

A host cell transformed with an expression vector or vectors selected from (a) to (m) below:

(a) an expression vector comprising a polynucleotide comprising a nucleotide sequence encoding a heavy chain consisting of the amino acid sequence shown in SEQ ID NO: 30;

(b) an expression vector comprising a polynucleotide comprising a nucleotide sequence encoding a light chain consisting of the amino acid sequence shown in SEQ ID NO: 32; (c) an expression vector comprising a polynucleotide comprising a nucleotide sequence encoding a heavy chain consisting of the amino acid sequence shown in SEQ ID NO: 30 and a polynucleotide comprising a nucleotide sequence encoding a light chain consisting of the amino acid sequence shown in SEQ ID NO: 32;

(d) an expression vector comprising a polynucleotide comprising a nucleotide sequence encoding a heavy chain consisting of the amino acid sequence shown in SEQ ID NO: 30, and an expression vector comprising a polynucleotide comprising a nucleotide sequence encoding a light chain consisting of the amino acid sequence shown in SEQ ID NO: 32;

(e) an expression vector comprising a polynucleotide comprising a nucleotide sequence encoding a heavy chain consisting of the amino acid sequence shown in SEQ ID NO: 30 and a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a light chain consisting of the amino acid sequence shown in SEQ ID NO: 32 and a polynucleotide comprising a nucleotide sequence encoding an Fc polypeptide consisting of the amino acid sequence shown in SEQ ID NO: 42;

(g) an expression vector comprising a polynucleotide comprising a nucleotide sequence encoding a heavy chain consisting of the amino acid sequence shown in SEQ ID NO: 30, and an expression vector comprising a polynucleotide comprising a nucleotide sequence encoding an Fc polypeptide consisting of the amino acid sequence shown on SEQ ID NO: 42;

(h) an expression vector comprising a polynucleotide comprising a nucleotide sequence encoding a light chain consisting of the amino acid sequence shown in SEQ ID NO: 32, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 30 and a polynucleotide comprising a nucleotide sequence encoding a light chain consisting of the amino acid sequence shown in SEQ ID NO: 32, as well as an expression vector comprising a polynucleotide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 30 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 32;

(k) an expression vector comprising a polynucleotide comprising a nucleotide sequence encoding a heavy chain consisting of the amino acid sequence shown in SEQ ID NO: 30, as well as an expression vector comprising a polynucleotide comprising a nucleotide sequence encoding a light chain consisting of the amino acid sequence shown in SEQ ID NO: 32 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 30, an expression vector comprising a polynucleotide comprising a nucleotide sequence encoding a light chain consisting of the amino acid sequence shown in SEQ ID NO: 32, and an expression vector comprising a polynucleotide comprising a nucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 30, a polynucleotide comprising a nucleotide sequence encoding a light chain consisting of the amino acid sequence shown in SEQ ID NO: 32, and a polynucleotide comprising a nucleotide sequence encoding an Fc polypeptide consisting of the amino acid sequence shown in SEQ ID NO: 42.

[41]

A host cell transformed with an expression vector or vectors selected from (a) to (m) below:

(a) an expression vector comprising a polynucleotide comprising a nucleotide sequence encoding a heavy chain consisting of the amino acid sequence shown in SEQ ID NO: 34;

(b) an expression vector comprising a polynucleotide comprising a nucleotide sequence encoding a light chain consisting of the amino acid sequence shown in SEQ ID NO: 36;

(c) an expression vector comprising a polynucleotide comprising a nucleotide sequence encoding a heavy chain consisting of the amino acid sequence shown in SEQ ID NO: 34 and a polynucleotide comprising a nucleotide sequence encoding a light chain consisting of the amino acid sequence shown in SEQ ID NO: 36;

(d) an expression vector comprising a polynucleotide comprising a nucleotide sequence encoding a heavy chain consisting of the amino acid sequence shown in SEQ ID NO: 34, and an expression vector comprising a polynucleotide comprising a nucleotide sequence encoding a light chain consisting of the amino acid sequence shown in SEQ ID NO: 36;

(e) an expression vector comprising a polynucleotide comprising a nucleotide sequence encoding a heavy chain consisting of the amino acid sequence shown in SEQ ID NO: 34, and a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a light chain consisting of the amino acid sequence shown in SEQ ID NO: 36 and a polynucleotide comprising a nucleotide sequence encoding an Fc polypeptide consisting of the amino acid sequence shown in SEQ ID NO: 42;

(g) an expression vector comprising a polynucleotide comprising a nucleotide sequence encoding a heavy chain consisting of the amino acid sequence shown in SEQ ID NO: 34, and an expression vector comprising a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a light chain consisting of the amino acid sequence shown in SEQ ID NO: 36, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 34 and a polynucleotide comprising a nucleotide sequence encoding a light chain consisting of the amino acid sequence shown in SEQ ID NO: 36, as well as an expression vector comprising a polynucleotide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 34 and a polynucleotide comprising a nucleotide sequence comprising an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 36;

(k) an expression vector comprising a polynucleotide comprising a nucleotide sequence encoding a heavy chain consisting of the amino acid sequence shown in SEQ ID NO: 34, as well as an expression vector comprising a polynucleotide comprising a nucleotide sequence encoding a light chain consisting of the amino acid sequence shown in SEQ ID NO: 36 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 34, an expression vector comprising a polynucleotide comprising a nucleotide sequence encoding a light chain consisting of the amino acid sequence shown in SEQ ID NO: 36, and an expression vector comprising a polynucleotide comprising a nucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 34, a polynucleotide comprising a nucleotide sequence encoding a light chain consisting of the amino acid sequence shown in SEQ ID NO: 36, and a polynucleotide comprising a nucleotide sequence encoding an Fc polypeptide consisting of the amino acid sequence shown in SEQ ID NO: 42.

[42]
A host cell transformed with an expression vector or vectors selected from (a) to (m) below:

(a) an expression vector comprising a polynucleotide comprising a nucleotide sequence encoding a heavy chain consisting of the amino acid sequence shown in SEQ ID NO: 38;

(b) an expression vector comprising a polynucleotide comprising a nucleotide sequence encoding a light chain consisting of the amino acid sequence shown in SEQ ID NO: 40;

(c) an expression vector comprising a polynucleotide comprising a nucleotide sequence encoding a heavy chain consisting of the amino acid sequence shown in SEQ ID NO: 38 and a polynucleotide comprising a nucleotide sequence encoding a light chain consisting of the amino acid sequence shown in SEQ ID NO: 40;

(d) an expression vector comprising a polynucleotide comprising a nucleotide sequence encoding a heavy chain consisting of the amino acid sequence shown in SEQ ID NO: 38, and an expression vector comprising a polynucleotide comprising a nucleotide sequence encoding a light chain consisting of the amino acid sequence shown in SEQ ID NO: 40;

(e) an expression vector comprising a polynucleotide comprising a nucleotide sequence encoding a heavy chain consisting of the amino acid sequence shown in SEQ ID NO: 38, and a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a light chain consisting of the amino acid sequence shown in SEQ ID NO: 40 and a polynucleotide comprising a nucleotide sequence encoding an Fc polypeptide consisting of the amino acid sequence shown in SEQ ID NO: 42;

(g) an expression vector comprising a polynucleotide comprising a nucleotide sequence encoding a heavy chain consisting of the amino acid sequence shown in SEQ ID NO: 38, and an expression vector comprising a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a light chain consisting of the amino acid sequence shown in SEQ ID NO: 40, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 38 and a polynucleotide comprising a nucleotide sequence encoding a light chain consisting of the amino acid sequence shown in SEQ ID NO: 40, as well as an expression vector comprising a polynucleotide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 38 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 40;

(k) an expression vector comprising a polynucleotide comprising a nucleotide sequence encoding a heavy chain consisting of the amino acid sequence shown in SEQ ID NO: 38, as well as an expression vector comprising a polynucleotide comprising a nucleotide sequence encoding a light chain consisting of the amino acid sequence shown in SEQ ID NO: 40 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 38, an expression vector comprising a polynucleotide comprising a nucleotide sequence encoding a light chain consisting of the amino acid sequence shown in SEQ ID NO: 40, and an expression vector comprising a polynucleotide comprising a nucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 38, a polynucleotide comprising a nucleotide sequence encoding a light chain consisting of the amino acid sequence shown in SEQ ID NO: 40, and a polynucleotide comprising a nucleotide sequence encoding an Fc polypeptide consisting of the amino acid sequence shown in SEQ ID NO: 42.

[43]

A host cell transformed with an expression vector or vectors selected from (a) to (m) below:

(a) an expression vector comprising a polynucleotide comprising a nucleotide sequence encoding a heavy chain of the one-armed anti-human NR1 antibody of [15];

(b) an expression vector comprising a polynucleotide comprising a nucleotide sequence encoding a light chain of the one-armed anti-human NR1 antibody of [15];

(c) an expression vector comprising a polynucleotide comprising a nucleotide sequence encoding a heavy chain of the one-armed anti-human NR1 antibody of [15] and a polynucleotide comprising a nucleotide sequence encoding a light chain of the antibody;

(d) an expression vector comprising a polynucleotide comprising a nucleotide sequence encoding a heavy chain of the one-armed anti-human NR1 antibody of [15], and an expression vector comprising a polynucleotide comprising a nucleotide sequence encoding a light chain of the antibody;

(e) an expression vector comprising a polynucleotide comprising a nucleotide sequence encoding a heavy chain of the one-armed anti-human NR1 antibody of [15] and a polynucleotide comprising a nucleotide sequence encoding an Fc polypeptide of the antibody;

(f) an expression vector comprising a polynucleotide comprising a nucleotide sequence encoding a light chain of the one-armed anti-human NR1 antibody of [15] and a polynucleotide comprising a nucleotide sequence encoding an Fc polypeptide of the antibody;

(g) an expression vector comprising a polynucleotide comprising a nucleotide sequence encoding a heavy chain of the one-armed anti-human NR1 antibody of [15], and an expression vector comprising a polynucleotide comprising a nucleotide sequence encoding an Fc polypeptide of the antibody;

(h) an expression vector comprising a polynucleotide comprising a nucleotide sequence encoding a light chain of the one-armed anti-human NR1 antibody of [15], and an expression vector comprising a polynucleotide comprising a nucleotide sequence encoding an Fc polypeptide of the antibody;

(i) an expression vector comprising a polynucleotide comprising a nucleotide sequence encoding a heavy chain of the one-armed anti-human NR1 antibody of [15] and a polynucleotide comprising a nucleotide sequence encoding a light chain of the antibody, as well as an expression vector comprising a polynucleotide comprising a nucleotide sequence encoding an Fc polypeptide of the antibody;

(j) an expression vector comprising a polynucleotide comprising a nucleotide sequence encoding a heavy chain of the one-armed anti-human NR1 antibody of [15] and a polynucleotide comprising a nucleotide sequence encoding an Fc polypeptide of the antibody, as well as an expression vector comprising a polynucleotide comprising a nucleotide sequence encoding a light chain of the antibody;

(k) an expression vector comprising a polynucleotide comprising a nucleotide sequence encoding a heavy chain of the one-armed anti-human NR1 antibody of [15], as well as an expression vector comprising a polynucleotide comprising a nucleotide sequence encoding a light chain of the antibody and a polynucleotide comprising a nucleotide sequence encoding an Fc polypeptide of the antibody;

(l) an expression vector comprising a polynucleotide comprising a nucleotide sequence encoding a heavy chain of the one-armed anti-human NR1 antibody of [15], an expression vector comprising a polynucleotide comprising a nucleotide sequence encoding a light chain of the antibody, and an expression vector comprising a polynucleotide comprising a nucleotide sequence encoding an Fc polypeptide of the antibody;

(m) an expression vector comprising a polynucleotide comprising a nucleotide sequence encoding a heavy chain of the one-armed anti-human NR1 antibody of [15], a polynucleotide comprising a nucleotide sequence encoding a light chain of the antibody, and a polynucleotide comprising a nucleotide sequence encoding an Fc polypeptide of the antibody.

[44]

A method for producing a one-armed anti-human NR1 antibody, comprising culturing the host cell of any one of [35] to [43], and expressing a polypeptide that constitutes a one-armed anti-human NR1 antibody.

[45]

A pharmaceutical composition comprising the one-armed anti-human NR1 antibody of any one of [1] to [17], and a pharmaceutically acceptable excipient.

[46]

The pharmaceutical composition of [45], wherein the pharmaceutical composition is for the treatment of anti-NMDAR encephalitis.

[47]

A method of treating anti-NMDAR encephalitis comprising administering a therapeutically effective amount of the one-armed anti-human NR1 antibody of any one of [1] to [17].

[48]

The one-armed anti-human NR1 antibody of any one of [1] to [17] for use in the treatment of anti-NMDAR encephalitis.

[49]

Use of the one-armed anti-human NR1 antibody of any one of [1] to [17] in the production of a pharmaceutical composition for the treatment of anti-NMDAR encephalitis.

[50]

A monovalent anti-human NR1 antibody derivative selected from any of the following (1) to (4):

(1) a monovalent anti-human NR1 antibody derivative comprising a heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, as well as a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8;

(2) a monovalent anti-human NR1 antibody derivative comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, as well as a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12;

(3) a monovalent anti-human NR1 antibody derivative comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, as well as a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16;

(4) a monovalent anti-human NR1 antibody derivative comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, as well as a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20.

[51]

A monovalent anti-human NR1 antibody derivative selected from any of the following (1) to (4):

(1) a monovalent anti-human NR1 antibody derivative comprising a heavy chain variable region consisting of the amino acid sequence shown in SEQ ID NO: 6, and a light chain variable region consisting of the amino acid sequence shown in SEQ ID NO: 8;

(2) a monovalent anti-human NR1 antibody derivative comprising a heavy chain variable region consisting of the amino acid sequence shown in SEQ ID NO: 10, and a light chain variable region consisting of the amino acid sequence shown in SEQ ID NO: 12;

(3) a monovalent anti-human NR1 antibody derivative comprising a heavy chain variable region consisting of the amino acid sequence shown in SEQ ID NO: 14, and a light chain variable region consisting of the amino acid sequence shown in SEQ ID NO: 16;

(4) a monovalent anti-human NR1 antibody derivative comprising a heavy chain variable region consisting of the amino acid sequence shown in SEQ ID NO: 18, and a light chain variable region consisting of the amino acid sequence shown in SEQ ID NO: 20.

[52]

A monovalent anti-human NR1 antibody derivative, wherein the antibody binds to human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR cell internalization by a pathogenic anti-human NR1 antibody derived from an anti-NMDAR encephalitis patient.

23

[53]
A polypeptide comprising a nucleotide sequence encoding the monovalent anti-human NR1 antibody derivative of any one of [50] to [52].
[54]
An expression vector comprising the polynucleotide of [53].
[55]
A host cell transformed with the expression vector of [54].
[56]
A method for producing a monovalent anti-human NR1 antibody derivative, comprising culturing the host cell of [55], and expressing a polypeptide that constitutes a monovalent anti-human NR1 antibody derivative.
[57]
A pharmaceutical composition comprising the monovalent anti-human NR1 antibody derivative of any one of [50] to [52], and a pharmaceutically acceptable excipient.
[58]
The pharmaceutical composition of [57], wherein the pharmaceutical composition is for the treatment of anti-NMDAR encephalitis.
[59]
A method of treating anti-NMDAR encephalitis comprising administering a therapeutically effective amount of the monovalent anti-human NR1 antibody derivative of any one of [50] to [52].
[60]
The monovalent anti-human NR1 antibody derivative of any one of [50] to [52] for use in the treatment of anti-NMDAR encephalitis.
[61]
Use of the monovalent anti-human NR1 antibody derivative of any one of [50] to [52] in the production of a pharmaceutical composition for the treatment of anti-NMDAR encephalitis.

Effects of the Invention

A monovalent human NR1 antibody derivative of the invention can be used as a therapeutic agent by binding to NMDAR competitively with a pathogenic anti-human NR1 antibody derived from an anti-NMDAR encephalitis patient and inhibiting NMDAR internalization.

Figure 4:
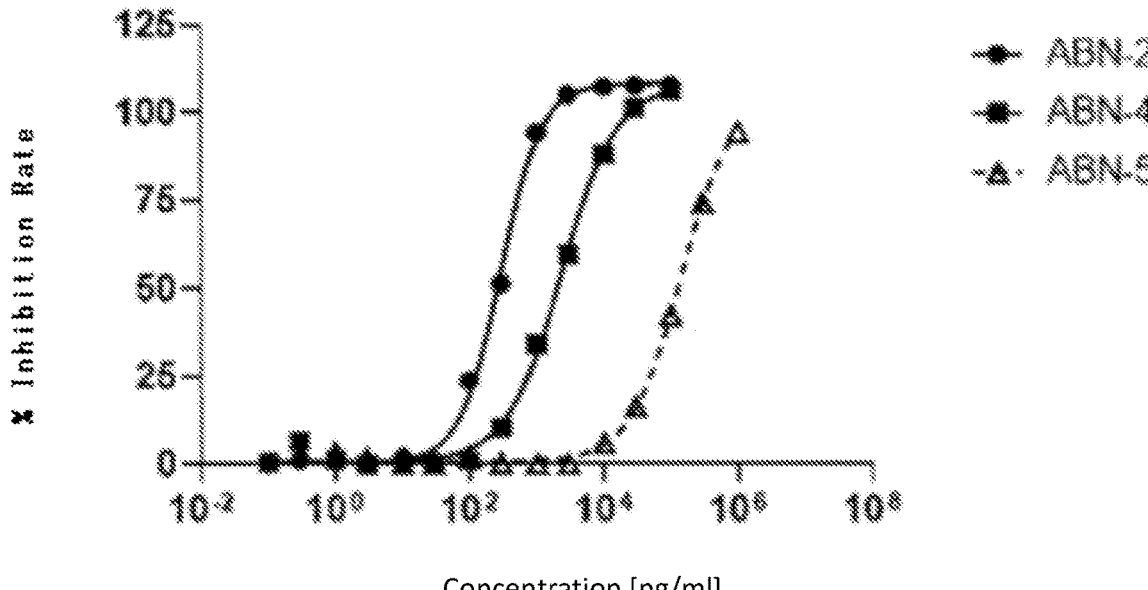
Figure 5:
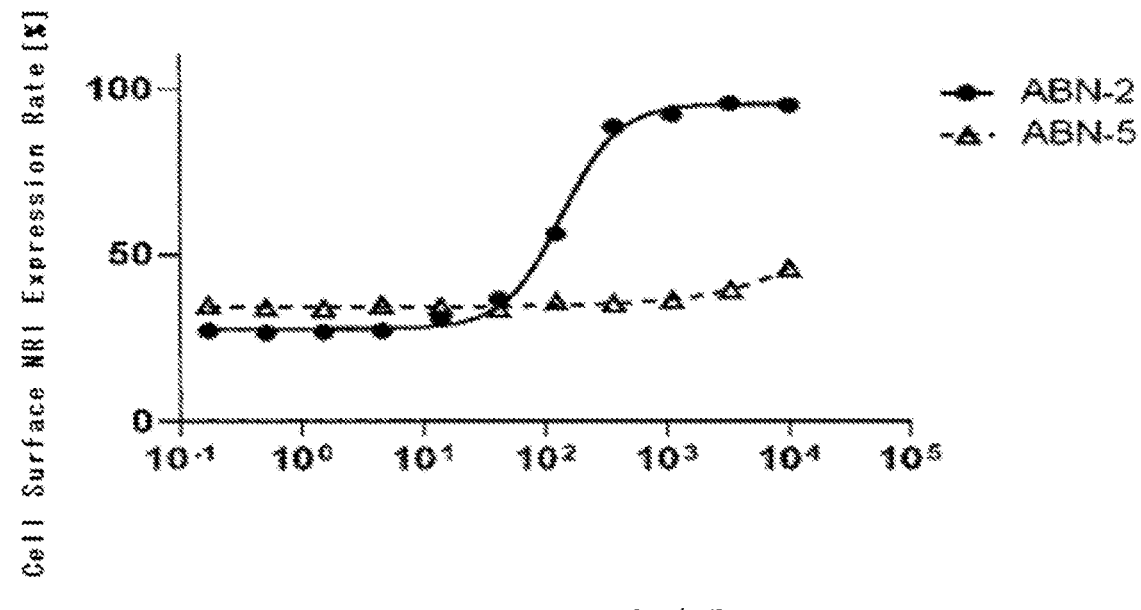
Figure 6:
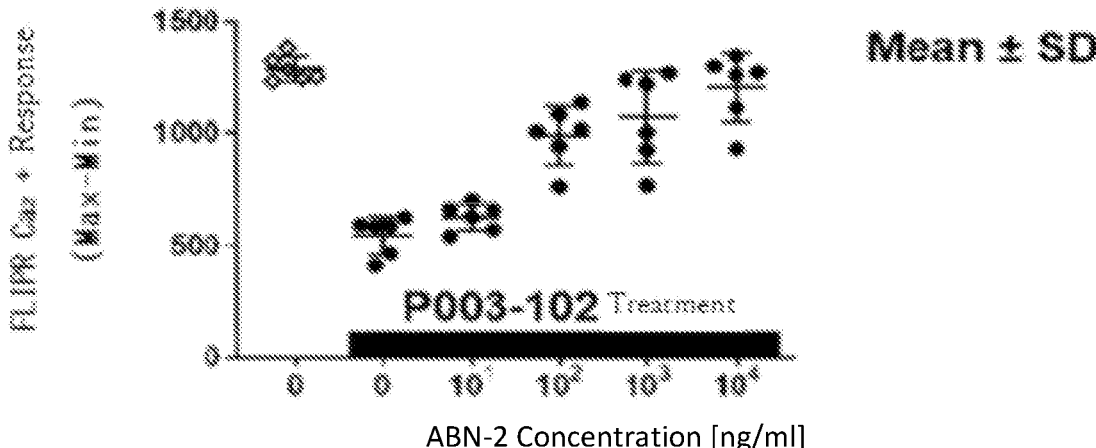
Figure 7:
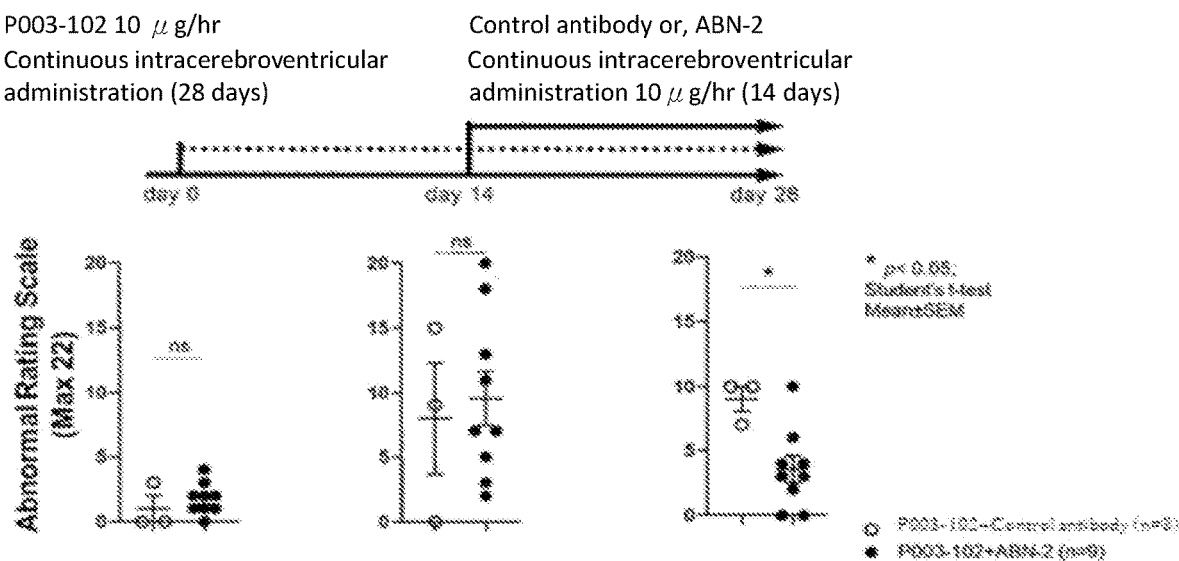
Figure 8:
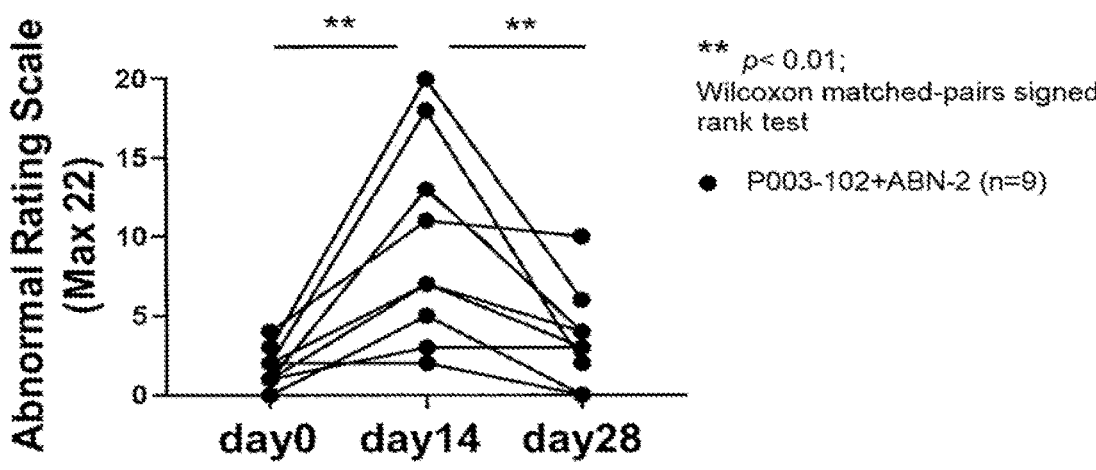
Figure 9:
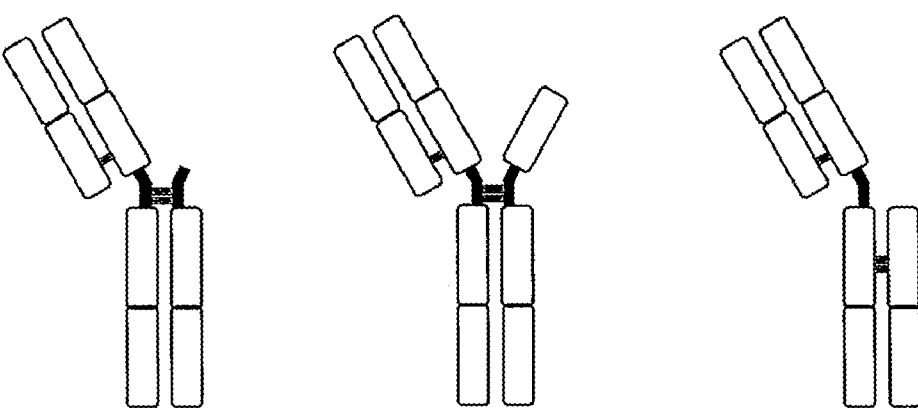

24 fluorescence intensity (GeoMFI) and the horizontal axis indicates the antibody concentration.
FIG. 4 illustrates inhibitory activity of ABN-2, ABN-4 and ABN-5 to a pathogenic anti-human NR1 antibody P003-102. The vertical axis indicates the inhibitory activity (inhibition rate) of biotin-labeled P003-102 to the binding to a human NR1 protein, and the horizontal axis indicates the antibody concentration.
FIG. 5 illustrates the rescue effect of ABN-2 in the expression level of NMDAR on the cell surface caused by a pathogenic anti-human NR1 antibody mixture. The vertical axis indicates NR1 expression rate (%) on the cell surface of an NMDAR-expressing HEK cell, and the horizontal axis indicates the antibody concentration.
FIG. 6 illustrates the rescue effect of ABN-2 on the decrease in the ion channel function of NMDAR caused by a pathogenic anti-human NR1 antibody P003-102. The vertical axis indicates a calcium ion influx caused by a NMDA stimulation, and the horizontal axis indicates the antibody concentration.
FIG. 7 illustrates the therapeutic effect of ABN-2 on common marmosets (hereinafter, referred to as "marmosets") wherein anti-NMDAR encephalitis-like symptoms were induced by a continuous intracerebroventricular administration of a pathogenic anti-human NR1 antibody P003-102. Day 0 is the day on which the administration of P003-102 to the marmosets in the control antibody administration group (P003-102+control antibody, n=3) and ABN-2 administration group (P003-102+ABN-2, n=9) was started. The control antibody or ABN-2 was administered intracerebroventricularly continuously for 14 days from day 14 (day 14) to day 28 (day 28). The vertical axes in the left, the center, and the right of FIG. 7, respectively, indicate the Abnormal Rating Scale (ARS) which is modified from the Parkinson's Disease Unified Scale (UPDRS, Behav. Brain Res. 2008, Vol. 194, pp. 152-161). The left of FIG. 7 shows the ARS of the control antibody administration group and the ABN-2 administration group on day 0, the center of FIG. 7 shows that on day 14 and the right of FIG. 7 shows that on day 28, respectively.
FIG. 8 illustrates the therapeutic effect of ABN-2 on common marmosets wherein anti-NMDAR encephalitis-like symptoms were induced by a continuous intracerebroventricular administration of the pathogenic anti-human NR1 antibody P003-102 as a change over time in ARS for each individual in the ABN-2 administration group (P003-102+ABN-2).
FIG. 9 illustrates a schematic diagram of a one-armed antibody.

DETAILED DESCRIPTION OF THE INVENTION

The following is a detailed description of the invention.
An antibody (or immunoglobulin) molecule is a glycoprotein composed of multiple units. There are five classes of antibodies: IgG, IgM, IgA, IgD and IgE. The basic structure of the antibody molecule, common to all classes, is a Y-shaped four-chain structure comprising two heavy chains with a molecular weight of 50,000 to 70,000 and two light chains with a molecular weight of 20,000 to 30,000. Heavy chains usually consist of a polypeptide chain comprising about 440 amino acids and have characteristic structures depending on the class, and they are called Igγ, Igμ, Igα, Igδ, and Igε, corresponding to IgG, IgM, IgA, IgD, and IgE, respectively. Furthermore, IgG has subclasses of IgG1, IgG2, IgG3, and IgG4, and the corresponding heavy chains are called Igγ1, Igγ2, Igγ3, and Igγ4, respectively. The light chains usually consist of a polypeptide chain comprising about 220 amino acids, and two types are known: L-type and K-type, called Igλ and Igκ, respectively. The two types of light chains can be paired with any type of heavy chain. The peptide composition of the basic structure of an antibody molecule consists of two identical heavy chains and two identical light chains, each linked by a disulfide bond and non-covalent bond, and the molecular weight of the antibody molecule is 150,000 to 190,000.

There are four intrachain disulfide bonds of an antibody molecule in a heavy chain (five in Igμ and Igε) and two in a light chain, forming a loop for every 100 to 110 amino acid residues. Their conformations are similar between the loops and are called structural unit or domain. A domain with both heavy chain and light chain located at N-termini, even if the sample is from the same class (subclass) of the same species of animal, has a diverse amino acid sequence and is called variable region. Each N-terminal domain of a heavy chain and light chain is called "heavy chain variable region (VH) and light chain variable region (VL)", respectively. The amino acid sequence of a C-terminal domain which is downstream of a variable region is almost constant for each class or subclass and is called a "constant region." The heavy chain constant region (CH) is further divided into three domains from the N-terminal side: CH1, CH2, and CH3. The light chain constant region is called "CL."

In the Y-shaped structure of an antibody, the portion corresponding to the vertical bar in the lower half of the Y-shape is called "Fc (Fragment, crystallizable) region". The Fc region consists of two "Fc polypeptides". The Fc polypeptide consists of CH2 and CH3 domains of a heavy chain. On the other hand, in the Y-shaped structure of an antibody, the portion corresponding to the diagonal bar that constitutes the V-shaped portion in the upper half of the Y-shaped structure is called "Fab (Fragment, antigen binding) region". A Fab region consists of VH and CH1 domains of a heavy chain and a light chain (VL and CL). An antibody binds to an antigen at the tip portion (antigen binding site) of the V-shape composed of two Fab regions. The Fab region and Fc region of a heavy chain are connected by a region called a hinge region. Further, the two heavy chains of the antibody are disulfide bonded.

An "antigen binding site" is composed of VH and VL, and the binding specificity to an antigen is determined by the amino acid sequence at this site. On the other hand, biological activities such as binding to a complement and various Fc receptor-expressing cells reflect differences in the structure of a constant region of each Ig class. The variability of the variable regions of a light chain and a heavy chain has been understood to be limited to three small hypervariable regions, which exist in both chains, and are referred to as "complementarity-determining region (CDR)" and has relatively large changes in amino acid sequence. On the other hand, the rest of the variable region is called framework region (FR) consisting of FR1 to FR4, and the changes in amino acid sequence is relatively small.

There are three CDRs in each N-terminus of a heavy chain and a light chain in the order of "CDR1," "CDR2," and "CDR3", consisting of about 5 to 10 amino acid residues. In particular, the CDR of a heavy chain is known to contribute to the binding to an antigen. In addition, among CDR1 to CDR3, the contribution of CDR3 is known to be the greatest.

The amino acid residue numbers of antibodies used herein can be defined according to their numbering system by specifying the Kabat numbering or EU index (Kabat, Sequences of Proteins of Immunological Interest, 5th Ed, 1991, NIH Publication No. 91-3242).

An "antibody derivative" herein is a molecule comprising at least one polypeptide chain derived from a full-length immunoglobulin molecule, which has antigen-binding activity. Representative antibody derivatives include a single chain variable region fragment (scFv), Fab fragment, Fab' fragment and F(ab')₂ fragment. An "scFv" is a monovalent antibody derivative consisting of a VH and VL linked by a linker. A "Fab fragment" is a monovalent antibody derivative consisting of a light chain and a heavy chain fragment comprising VH, CH1 domain and a part of a hinge region. A "F(ab')₂ Fab' fragment" is a monovalent antibody derivative consisting of a light chain and a heavy chain fragment comprising VH, CH1 domain and a part of a hinge region, and this part of a hinge region comprises a cysteine residue that constitutes the S—S binding between heavy chains. The term "monovalent" means comprising one antigen binding site.

A "one-armed antibody" is also a type of antibody derivative. Herein, a "one-armed antibody" is a monovalent antibody derivative comprising one Fab region and one Fc region, wherein the Fab region is connected to one of two Fc polypeptides in the Fc region. The Fab region and the one Fc polypeptide may be connected via a hinge region or peptide linker. In one embodiment, a one-armed antibody comprises one heavy chain (VH, CH1 domain, hinge region, Fc polypeptides (CH2 domain and CH3 domain)), one light chain (VL and CL) and Fc polypeptides (FIG. 9). In one embodiment, a one-armed antibody is a one-armed antibody comprising one heavy chain, one light chain, and Fc polypeptides, wherein a hinge region is added to the Fc polypeptides (FIG. 9—left). In one embodiment, a one-armed antibody is a one-armed antibody consisting of one heavy chain, one light chain, and Fc polypeptides, wherein a CH1 domain is connected to the Fc polypeptides via a hinge region (FIG. 9—center). In one embodiment, a one-armed antibody is a one-armed antibody consisting of one heavy chain, one light chain, and Fc polypeptides (FIG. 9—right). In one embodiment, a one-armed antibody may have two Fc polypeptides bound by an S—S bond between heavy chains in the hinge region portion (FIG. 9—left and center), or the two Fc polypeptides may comprise a modified residue or added cysteine residue in one or both Fc polypeptides to allow them to bind to each other (FIG. 9—right).

An "anti-human NR1 antibody" herein means an antibody that binds to human NR1. Whether or not it binds to human NR1 can be found using a well-known method for measuring binding activity. Methods for measuring binding activity include, for example, Enzyme-Linked Immunosorbent Assay (ELISA). If ELISA is used, for example, a full-length or partial polypeptide of a human NR1 protein that can be produced by referring to an amino acid sequence indicated in GenBank accession #NP_015566.1 is solid-phased on an ELISA plate, and after being reacted by adding a test antibody, it is reacted with a secondary antibody such as an anti-IgG antibody labeled with an enzyme such as horseradish peroxidase (HRP). After the reaction, it becomes possible to confirm whether the test antibody binds to human NR1 or not by identifying the binding of the secondary antibody through performing washing operation and activity measurement using a reagent or the like to detect its activity. As a specific evaluation method, for example, the method described in Example 5 below can be used.

An anti-human NR1 antibody of the invention also comprises an antibody that binds to NR1 derived from another animal (e.g., anti-monkey NR1) in addition to an anti-human NR1, as long as the antibody binds to a human NR1.

<One-Armed Anti-Human NR1 Antibody of the Present Invention>

Herein, a "one-armed anti-human NR1 antibody" is a one-armed antibody that binds to human NR1.

A one-armed anti-human NR1 antibody of the invention comprises a one-armed anti-human NR1 antibody selected from any of the following (1) to (5):

(1) a one-armed anti-human NR1 antibody comprising a heavy chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, and a light chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4;

(2) a one-armed anti-human NR1 antibody comprising a heavy chain variable region comprising a CDR1 consisting of the amino acid sequence of amino acid numbers 31 to 35 of SEQ ID NO: 6, a CDR2 consisting of the amino acid sequence of amino acid numbers 50 to 60 of SEQ ID NO: 6, and a CDR3 consisting of the amino acid sequence of amino acid numbers 99 to 110 of SEQ ID NO: 6, and a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8;

(3) a one-armed anti-human NR1 antibody comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, and a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12;

(4) a one-armed anti-human NR1 antibody comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, and a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16;

(5) a one-armed anti-human NR1 antibody comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, and a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20.

In one embodiment, a one-armed anti-human NR1 antibody of the invention is a one-armed anti-human NR1 antibody selected from any of the following (6) to (10):

(6) a one-armed anti-human NR1 antibody comprising a heavy chain variable region consisting of the amino acid sequence shown in SEQ ID NO: 2, and a light chain variable region consisting of the amino acid sequence shown in SEQ ID NO: 4;

(7) a one-armed anti-human NR1 antibody comprising a heavy chain variable region consisting of the amino acid sequence shown in SEQ ID NO: 6, and a light chain variable region consisting of the amino acid sequence shown in SEQ ID NO: 8;

(8) a one-armed anti-human NR1 antibody comprising a heavy chain variable region consisting of the amino acid sequence shown in SEQ ID NO: 10, and a light chain variable region consisting of the amino acid sequence shown in SEQ ID NO: 12;

(9) a one-armed anti-human NR1 antibody comprising a heavy chain variable region consisting of the amino acid sequence shown in SEQ ID NO: 14, and a light chain variable region consisting of the amino acid sequence shown in SEQ ID NO: 16;

(10) a one-armed anti-human NR1 antibody comprising a heavy chain variable region consisting of the amino acid sequence shown in SEQ ID NO: 18, and a light chain variable region consisting of the amino acid sequence shown in SEQ ID NO: 20.

In one embodiment, a one-armed anti-human NR1 antibody of the invention is a one-armed anti-human NR1 antibody selected from any of the following (1) to (5):

(1) a one-armed anti-human NR1 antibody comprising a heavy chain comprising a heavy chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, a light chain comprising a light chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4, as well as an Fc polypeptide;

(2) a one-armed anti-human NR1 antibody comprising a heavy chain comprising heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, a light chain comprising a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8, as well as an Fc polypeptide;

(3) a one-armed anti-human NR1 antibody comprising a heavy chain comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, a light chain comprising a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12, as well as an Fc polypeptide;

(4) a one-armed anti-human NR1 antibody comprising a heavy chain comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, a light chain comprising a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16, as well as an Fc polypeptide;

(5) a one-armed anti-human NR1 antibody comprising a heavy chain comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, a light chain comprising a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20; and an Fc polypeptide.

In one embodiment, a one-armed anti-human NR1 antibody of the invention is a one-armed anti-human NR1 antibody selected from any of the following (6) to (10):

(6) a one-armed anti-human NR1 antibody comprising a heavy chain comprising a heavy chain variable region consisting of the amino acid sequence shown in SEQ ID NO: 2, a light chain comprising a light chain variable region consisting of the amino acid sequence shown in SEQ ID NO: 4, and an Fc polypeptide;

(7) a one-armed anti-human NR1 antibody comprising a heavy chain comprising a heavy chain variable region consisting of the amino acid sequence shown in SEQ ID NO: 6, a light chain comprising a light chain variable region consisting of the amino acid sequence shown in SEQ ID NO: 8, and an Fc polypeptide;

(8) a one-armed anti-human NR1 antibody comprising a heavy chain comprising a heavy chain variable region consisting of the amino acid sequence shown in SEQ ID NO: 10, a light chain comprising a light chain variable region consisting of the amino acid sequence shown in SEQ ID NO: 12, and an Fc polypeptide;

(9) a one-armed anti-human NR1 antibody comprising a heavy chain comprising a heavy chain variable region consisting of the amino acid sequence shown in SEQ ID NO: 14, a light chain comprising a light chain variable region consisting of the amino acid sequence shown in SEQ ID NO: 16, and an Fc polypeptide;

(10) a one-armed anti-human NR1 antibody comprising a heavy chain comprising a heavy chain variable region consisting of the amino acid sequence shown in SEQ ID NO: 18, a light chain comprising a light chain variable region consisting of the amino acid sequence shown in SEQ ID NO: 20, and an Fc polypeptide.

As a heavy chain constant region from which a CH1 domain and FC polypeptides of a one-armed anti-human NR1 antibody of the invention are derived, any of Igγ, Igμ, Igα, Igδ or Igε constant regions can be selected. Igγ, for example, can be selected from Igγ1, Igγ2, Igγ3 or Igγ4. In one embodiment, a one-armed anti-human NR1 antibody of the invention comprises a CH1 domain and Fc polypeptide derived from an Igγ1 constant region. In one embodiment, a one-armed anti-human NR1 antibody of the invention comprises a CH1 domain and Fc polypeptide derived from a human Igγ1 constant region.

As a CL of a one-armed anti-human NR1 antibody of the invention, any of Igλ or Igκ constant regions can be selected. In one embodiment, a one-armed anti-human NR1 antibody of the invention comprises a CL which is an Igk constant region. In one embodiment, a one-armed anti-human NR antibody of the invention comprises a CL, which is a human Igκ constant region.

A heavy chain constant region of a one-armed anti-human NR1 antibody of the invention may have mutations that decrease antibody-dependent cytotoxic activity or complement-dependent cytotoxic activity. L234A indicates a substitution of alanine for leucine at amino acid position 234 according to the EU index in the human Igγ1 constant region. L235A indicates a substitution of alanine for leucine at amino acid position 235 according to the EU index in the human Igγ1 constant region. A human Igγ1 constant region which has L234A and L235A amino acid mutations (hereinafter, referred to as "LALA mutation") includes, for example, a human Igγ1 constant region consisting of the amino acid sequence of amino acid numbers 121 to 450 in SEQ ID NO: 22. The mutation is known to decrease antibody-dependent cytotoxic activity and complement-dependent cytotoxic activity of the antibody (Mol. Immunol., 1992, Vol. 29, pp. 633-639/J. Immunol., 2000, Vol. 164, pp. 4178-4184). In addition, in a mouse antibody, D265A amino acid mutation in IgG1 is known to decrease antibody-dependent cytotoxic activity and complement-dependent cytotoxic activity of the antibody (J. Immunol., 2008, Vol. 181, pp. 6664-6669/Nat. Med., 2000, Vol. 6, pp. 443-446). If the effect of an antibody with decreased antibody-dependent cytotoxic activity or complement-dependent cytotoxic activity is to be observed in a mouse model, a mouse antibody which has a D265A amino acid mutation antibody can be used in place of a human antibody which has LALA mutations.

Other mutations based on known techniques can also be introduced into a heavy chain constant region of a one-armed anti-human NR1 antibody of the invention. For example, a one-armed anti-human NR1 antibody of the invention may have a mutation based on the knobs-into-holes technology (hereinafter, referred to as "Knobs-into-holes mutation"). The knobs-into-holes technology is a technology for obtaining the desired heterodimerized antibody molecule efficiently by substituting the amino acid side chain present in the CH3 region of one of the heavy chains with a larger side chain (knob) and by substituting the amino acid side chain present in the CH3 region of the other one of the heavy chains with a smaller side chain (hole) so that the knob is positioned within the hole, thereby promoting het-erodimerization of the heavy chains (Nature, 1994, Vol. 372, pp. 379-383/Nature Biotech., 1998, Vol. 16, pp. 677-681/J. Mol. Biol., 1997, Vol. 270, pp. 26-35/Proc. Natl. Acad. Sci. USA, 2013, Vol. 110, pp. E2987-E2996).

In one embodiment, a one-armed anti-human NR1 antibody of the invention comprises the Fc region which has L234A and L235A amino acid mutations (LALA mutations).

In one embodiment, a one-armed anti-human NR1 antibody of the invention comprises the Fc region which has knobs-into-holes mutation.

In one embodiment, a one-armed anti-human NR1 antibody of the invention comprises the Fc region which has L234A and L235A amino acid mutations (LALA mutations) and knobs-into-holes mutations.

In one embodiment, knobs-into-holes mutations of a one-armed anti-human NR1 antibody of the invention are a T366W mutation in one Fc polypeptide which forms its Fc region and T366S, L368A and Y407V mutations in the other Fc polypeptide which forms its Fc region (see WO1998/050431).

A "human antibody" herein refers to an antibody with a human immunoglobulin amino acid sequence. A "humanized antibody" herein refers to an antibody wherein some, most, or all of the amino acid residues other than the CDRs are substituted with amino acid residues derived from human immunoglobulin molecules. A humanized antibody can be produced by referring to, for example, U.S. Pat. Nos. 5,225,539 and 6,180,370, etc.

In one embodiment, a one-armed anti-human NR1 antibody of the invention is a human antibody or humanized antibody.

In one embodiment, a one-armed anti-human NR1 antibody of the invention is a one-armed anti-human NR1 antibody comprising a heavy chain consisting of the amino acid sequence shown in SEQ ID NO: 22, a light chain consisting of the amino acid sequence shown in SEQ ID NO: 24, and an Fc polypeptide consisting of the amino acid sequence shown in SEQ ID NO: 42.

A heavy chain comprising the amino acid sequence shown in SEQ ID NO: 22 has LALA mutations, and the mutations are located in the alanine residues at amino acid numbers 237 and 238 in SEQ ID NO: 22.

A heavy chain consisting of the amino acid sequence shown in SEQ ID NO: 22 has knobs-into-holes mutations (T366S, L368A and Y407V), and the mutations are located in the serine residue at amino acid number 369, the alanine residue at amino acid number 371, and the valine residue at amino acid number 410 in SEQ ID NO: 22.

An Fc polypeptide consisting of the amino acid sequence shown in SEQ ID NO: 42 has LALA mutations, and the mutations are located in the alanine residues at amino acid numbers 9 and 10 in SEQ ID NO: 42. The Fc polypeptide comprising the amino acid sequence shown in SEQ ID NO: 42 also has a knobs-into-holes mutation (T366W) and the mutation is located in the tryptophan residue at amino acid number 141.

In one embodiment, a one-armed anti-human NR1 antibody of the invention is a one-armed anti-human NR1 antibody comprising a heavy chain consisting of the amino acid sequence shown in SEQ ID NO: 26, a light chain consisting of the amino acid sequence shown in SEQ ID NO: 28, and an Fc polypeptide consisting of the amino acid sequence shown in SEQ ID NO: 42.

In one embodiment, a one-armed anti-human NR1 antibody of the invention is a one-armed anti-human NR1 antibody comprising a heavy chain consisting of the amino acid sequence shown in SEQ ID NO: 30, a light chain consisting of the amino acid sequence shown in SEQ ID NO: 32, and an Fc polypeptide consisting of the amino acid sequence shown in SEQ ID NO: 42.

In one embodiment, a one-armed anti-human NR1 antibody of the invention is a one-armed anti-human NR1 antibody comprising a heavy chain consisting of the amino acid sequence shown in SEQ ID NO: 34, a light chain consisting of the amino acid sequence shown in SEQ ID NO: 36, and an Fc polypeptide consisting of the amino acid sequence shown in SEQ ID NO: 42.

In one embodiment, a one-armed anti-human NR1 antibody of the invention is a one-armed anti-human NR1 antibody comprising a heavy chain consisting of the amino acid sequence shown in SEQ ID NO: 38, a light chain consisting of the amino acid sequence shown in SEQ ID NO: 40, and an Fc polypeptide consisting of the amino acid sequence shown in SEQ ID NO: 42.

Like the heavy chain consisting of the amino acid sequence shown in SEQ ID NO: 22, the heavy chains consisting of the amino acid sequence shown in SEQ ID NO: 26, 30, 34 and 38 also have LALA mutations and knobs-into-holes mutations (T366S, L368A and Y407V).

In one embodiment, a one-armed anti-human NR1 antibody of the invention binds to a human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR receptor cell internalization by a patho-genic anti-human NR1 antibody derived from an anti-NMDAR encephalitis patient.

Herein, two antibodies binding "competitively" to the same antigen protein means that the epitopes on the antigen protein to which each of the two antibodies binds are identical, or that a portion of the epitopes on the antigen protein to which each of the two antibodies binds is common, or that one of the antibodies binding to an epitope on this antigen protein changes the three-dimensional structure of the antigen protein comprising the epitope portion to which the other antibody binds on the antigen protein, resulting that the other antibody will no longer be able to bind to the epitope portion on the antigen protein.

For example, a person skilled in the art can obtain multiple one-armed anti-human NR1 antibodies that have been produced based on an antibody that was obtained by immunizing a mouse or a rat with a human NR1 polypeptide. Then, according to the method disclosed in Examples 3-5, etc., herein, a one-armed anti-human NR1 antibody can be selected from the obtained multiple anti-human NR1 antibodies by screening using an anti-human NR1 antibody comprising a heavy chain variable region consisting of the amino acid sequence shown in SEQ ID NO: 2 and a light chain variable region consisting of the amino acid sequence shown in SEQ ID NO: 4, and selecting an anti-human NR antibody that binds to human NRA competitively with the anti-human NR1 antibody and inhibits NMDA receptor cell internalization by a pathogenic anti-human NR1 antibody.

A "one-armed anti-human NR1 antibody that binds to a human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4" includes, for example, ABN_1-1-175, ABN_1-178.3, ABN_3-385, ABN_3-502, and their derivatives that are identified as a result of the ELISA competitive assay described in Example 5 herein.

A "one-armed anti-human NR1 antibody that binds to a human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NM/DAR receptor cell internalization by a pathogenic anti-human NR1 antibody derived from an anti-NMDAR encephalitis patient" includes, for example, the ABN 1-175, ABN_1-178, ABN_3-385, ABN_3-502 or a one-armed antibody comprising an antigen binding site of P003-102 described in Example 1, or more specifically, a one-armed anti-human NR1 antibody ABN-1 to -5 produced in Example 2 or Example 6 herein.

When antibodies are expressed in cells, they are known to undergo post-translational modifications. Examples of post-translational modifications include cleavage of a heavy chain C-terminal lysine by carboxypeptidase, modification of a heavy chain and light chain N-terminal glutamine or glutamic acid with a pyroglutamic acid by pyroglutamylation, glycosylation, oxidation, deamidation and sacchari-fication, etc. Such post-translational modifications are known to occur in various antibodies (J. Pharm. Sci., 2008, Vol. 97, pp. 2426-2447).

An example of a one-armed anti-human NR1 antibody of the invention resulted from a post-translational modification includes a one-arm anti-human NR1 antibody that has undergone N-terminal pyroglutamylation of a heavy chain variable region and/or deletion of a heavy chain C-terminal lysine. It is known in the art that such post-translational modifications by N-terminal pyroglutamylation or C-terminus lysine deletion do not affect the activity of an antibody (Anal. Biochem., 2006, Vol. 348, pp. 24-39).

In one embodiment, a one-armed anti-human NR1 antibody resulted from a post-translational modification.

In one embodiment, a one-armed anti-human NR1 antibody resulted from a post-translational modification of N-terminal pyroglutamylation of a heavy chain variable region and/or deletion of a heavy chain C-terminal lysine of the one-armed anti-human NR1 antibody of the invention.

A one-armed anti-human NR1 antibody of the invention can be easily produced by a person skilled in the art using a method well-known in the art, based on the VH and VL sequence information etc., of a one-armed anti-human NR1 antibody of the invention disclosed herein. The one-armed anti-human NR1 antibody of the invention can be produced by, for example, the method described in "Method for producing a one-armed anti-human NR1 antibody of the present invention, and the one-armed anti-human NR1 antibody produced thereby" below, but not limited thereto.

A one-armed anti-human NR1 antibody of the invention, after further purification, if necessary, is formulated by a standard method and can be used for the treatment of anti-NMDAR encephalitis, etc.

<Polynucleotide of the Invention>

A polynucleotide of the invention includes a polynucleotide comprising a nucleotide sequence encoding a heavy chain variable region of the one-armed anti-human NR1 antibody of the invention and a polynucleotide comprising a nucleotide sequence encoding a light chain variable region of the one-armed anti-human NR1 antibody of the invention.

In one embodiment, the polynucleotide of the invention is a polynucleotide comprising a sequence described in (a) and/or (b) below:

(a) a nucleotide sequence encoding a heavy chain variable region of the one-armed anti-human NR1 antibody selected from (a-1) to (a-4) below:

(a-1) a heavy chain variable region comprising CDR1 consisting of the amino acid sequence of amino acid numbers 31 to 35 of SEQ ID NO: 6, CDR2 consisting of the amino acid sequence of amino acid numbers 50 to 66 of SEQ ID NO: 6, and CDR3 consisting of the amino acid sequence of amino acid numbers 99 to 110 of SEQ ID NO: 6;

(a-2) a heavy chain variable region comprising CDR1 consisting of the amino acid sequence of amino acid numbers 31 to 35 of SEQ ID NO: 10, CDR2 consisting of the amino acid sequence of amino acid numbers 50 to 66 of SEQ ID NO: 10, and CDR3 consisting of the amino acid sequence of amino acid numbers 99 to 111 of SEQ ID NO: 10;

(a-3) a heavy chain variable region comprising CDR1 consisting of the amino acid sequence of amino acid numbers 31 to 36 of SEQ ID NO: 14, CDR2 consisting of the amino acid sequence of amino acid numbers 51 to 66 of SEQ ID NO: 14, and CDR3 consisting of the amino acid sequence of amino acid numbers 99 to 108 of SEQ ID NO: 14;

(a-4) a heavy chain variable region comprising CDR1 consisting of the amino acid sequence of amino acid numbers 31 to 36 of SEQ ID NO: 18, CDR2 consisting of the amino acid sequence of amino acid numbers 51 to 66 of SEQ ID NO: 18, and CDR3 consisting of the amino acid sequence of amino acid numbers 99 to 108 of SEQ ID NO: 18; and/or (b) a nucleotide sequence encoding a light chain variable region of the one-armed anti-human NR1 antibody selected from (b-1) to (b-4) below:

(b-1) a light chain variable region comprising CDR1 consisting of the amino acid sequence of amino acid numbers 24 to 34 of SEQ ID NO: 8, CDR2 consisting of the amino acid sequence of amino acid numbers 50 to 56 of SEQ ID NO: 8, and CDR3 consisting of the amino acid sequence of amino acid numbers 89 to 98 of SEQ ID NO: 8;

(b-2) a light chain variable region comprising CDR1 consisting of the amino acid sequence of amino acid numbers 24 to 34 of SEQ ID NO: 12, CDR2 consisting of the amino acid sequence of amino acid numbers 50 to 56 of SEQ ID NO: 12, and CDR3 consisting of the amino acid sequence of amino acid numbers 89 to 97 of SEQ ID NO: 12;

(b-3) a light chain variable region comprising CDR1 consisting of amino acid sequences of amino acid number 24 to 34 of SEQ ID NO: 16, CDR2 consisting of the amino acid sequence of amino acid numbers 50 to 56 of SEQ ID NO: 16, and CDR3 consisting of the amino acid sequence of amino acid numbers 89 to 97 of SEQ ID NO: 16;

(b-4) a light chain variable region comprising CDR1 consisting of the amino acid sequence of amino acid numbers 24 to 34 of SEQ ID NO: 20, CDR2 consisting of the amino acid sequence of amino acid numbers 50 to 56 of SEQ ID NO: 20, and CDR3 consisting of the amino acid sequence of amino acid numbers 89 to 98 of SEQ ID NO: 20.

In one embodiment, the polynucleotide of the invention is a polynucleotide comprising a nucleotide sequence described in (a) and/or (b) below:

(a) a nucleotide sequence encoding a heavy chain variable region of the one-armed anti-human NR1 antibody selected from (a-1) to (a-4) below:

(a-1) a heavy chain variable region consisting of amino acid sequence shown in SEQ ID NO: 6;

(a-2) a heavy chain variable region consisting of amino acid sequence shown in SEQ ID NO: 10;

(a-3) a heavy chain variable region consisting of amino acid sequence shown in SEQ ID NO: 14;

(a-4) a heavy chain variable region consisting of amino acid sequence shown in SEQ ID NO: 18; and/or (b) a nucleotide sequence encoding a light chain variable region of the one-armed anti-human NR1 antibody selected from (b-1) to (b-4) below:

(b-1) a light chain variable region consisting of amino acid sequence shown in SEQ ID NO: 8;

(b-2) a light chain variable region consisting of amino acid sequence shown in SEQ ID NO: 12;

(b-3) a light chain variable region consisting of amino acid sequence shown in SEQ ID NO: 16;

(b-4) a light chain variable region consisting of amino acid sequence shown in SEQ ID NO: 20.

In one embodiment, the polynucleotide of the invention is a polynucleotide comprising a nucleotide sequence described in (a) and/or (b) below:

(a) a nucleotide sequence encoding a heavy chain of the one-armed anti-human NR1 antibody selected from (a-1) to (a-4) below:

(a-1) a heavy chain comprising a heavy chain variable region comprising CDR1 consisting of the amino acid sequence of amino acid numbers 31 to 35 of SEQ ID NO: 6, CDR2 consisting of the amino acid sequence of amino acid numbers 50 to 66 of SEQ ID NO: 6, and CDR3 consisting of the amino acid sequence of amino acid numbers 99 to 110 of SEQ ID NO: 6;

(a-2) a heavy chain comprising a heavy chain variable region comprising CDR1 consisting of the amino acid sequence of amino acid numbers 31 to 35 of SEQ ID NO: 10, CDR2 consisting of the amino acid sequence of amino acid numbers 50 to 66 of SEQ ID NO: 10, and CDR3 consisting of the amino acid sequence of amino acid numbers 99 to 111 of SEQ ID NO: 10;

(a-3) a heavy chain comprising a heavy chain variable region comprising CDR1 consisting of the amino acid sequence of amino acid numbers 31 to 36 of SEQ ID NO: 14, CDR2 consisting of the amino acid sequence of amino acid numbers 51 to 66 of SEQ ID NO: 14, and CDR3 consisting of the amino acid sequence of amino acid numbers 99 to 108 of SEQ ID NO: 14;

(a-4) a heavy chain comprising a heavy chain variable region comprising CDR1 consisting of the amino acid sequence of amino acid numbers 31 to 36 of SEQ ID NO: 18, CDR2 consisting of the amino acid sequence of amino acid numbers 51 to 66 of SEQ ID NO: 18, and CDR3 consisting of the amino acid sequence of amino acid numbers 99 to 108 of SEQ ID NO: 18; and/or (b) a nucleotide sequence encoding a light chain of the one-armed anti-human NR1 antibody selected from (b-1) to (b-4) below:

(b-1) a light chain comprising a light chain variable region comprising CDR1 consisting of the amino acid sequence of amino acid numbers 24 to 34 of SEQ ID NO: 8, CDR2 consisting of the amino acid sequence of amino acid numbers 50 to 56 of SEQ ID NO: 8, and CDR3 consisting of the amino acid sequence of amino acid numbers 89 to 98 of SEQ ID NO: 8;

(b-2) a light chain comprising a light chain variable region comprising CDR1 consisting of the amino acid sequence of amino acid numbers 24 to 34 of SEQ ID NO: 12, CDR2 consisting of the amino acid sequence of amino acid numbers 50 to 56 of SEQ ID NO: 12, and CDR3 consisting of the amino acid sequence of amino acid numbers 89 to 97 of SEQ ID NO: 12;

(b-3) a light chain comprising a light chain variable region comprising CDR1 consisting of the amino acid sequence of amino acid numbers 24 to 34 of SEQ ID NO: 16, CDR2 consisting of the amino acid sequence of amino acid numbers 50 to 56 of SEQ ID NO: 16, and CDR3 consisting of the amino acid sequence of amino acid numbers 89 to 97 of SEQ ID NO: 16;

(b-4) a light chain comprising a light chain variable region comprising CDR1 consisting of the amino acid sequence of amino acid numbers 24 to 34 of SEQ ID NO: 20, CDR2 consisting of the amino acid sequence of amino acid numbers 50 to 56 of SEQ ID NO: 20, and CDR3 consisting of the amino acid sequence of amino acid numbers 89 to 97 of SEQ ID NO: 20.

In one embodiment, the polynucleotide of the invention comprises a nucleotide sequence described in (a) and/or (b) below:

(a) A nucleotide sequence encoding a heavy chain variable region of the one-armed anti-human NR1 antibody selected from (a-1) to (a-4) below:

(a-1) a heavy chain comprising a heavy chain variable region consisting of amino acid sequence shown in SEQ ID NO: 6;

(a-2) a heavy chain comprising a heavy chain variable region consisting of the amino acid sequence shown in SEQ ID NO: 10;

(a-3) a heavy chain comprising a heavy chain variable region consisting of the amino acid sequence shown in SEQ ID NO: 14 (a-4) a heavy chain comprising a heavy chain variable region consisting of the amino acid sequence shown in SEQ ID NO: 18; and/or (b) a nucleotide sequence encoding a light chain variable region of the one-armed anti-human NR1 antibody selected from (b-1) to (b-4) below:

(b-1) a light chain comprising a light chain variable region consisting of the amino acid sequence shown in SEQ ID NO: 8;

(b-2) a light chain comprising a light chain variable region consisting of the amino acid sequence shown in SEQ ID NO: 12;

(b-3) a light chain comprising a light chain variable region consisting of the amino acid sequence shown in SEQ ID NO: 16;

(b-4) a light chain comprising a light chain variable region consisting of the amino acid sequence shown in SEQ ID NO: 20.

In one embodiment, the polynucleotide of the invention comprises a nucleotide sequence described in (a) and/or (b) below:

(a) a nucleotide sequence encoding a heavy chain consisting of the amino acid sequence shown in SEQ ID NO: 26; and/or (b) a nucleotide sequence encoding a light chain consisting of the amino acid sequence shown in SEQ ID NO: 28.

The polynucleotide encoding a heavy chain consisting of the amino acid sequence shown in SEQ ID NO: 26 includes, for example, a polynucleotide comprising the nucleotide sequence shown in SEQ ID NO: 25.

The polynucleotide encoding a light chain consisting of the amino acid sequence shown in SEQ ID NO: 28 includes, for example, a polynucleotide comprising the nucleotide sequence shown in SEQ ID NO: 27.

In one embodiment, the polynucleotide of the invention comprises a nucleotide sequence described in (a) and/or (b) below:

(a) a nucleotide sequence encoding a heavy chain consisting of amino acid sequence shown in SEQ ID NO: 30; and/or (b) a nucleotide sequence encoding a light chain consisting of amino acid sequence shown in SEQ ID NO: 32.

The polynucleotide comprising a nucleotide sequence encoding a heavy chain consisting of the amino acid sequence shown in SEQ ID NO: 30 includes, for example, a polynucleotide comprising the nucleotide sequence shown in SEQ ID NO: 29.

The polynucleotide comprising a nucleotide sequence encoding a light chain consisting of the amino acid sequence shown in SEQ ID NO: 32 includes, for example, a polynucleotide comprising the nucleotide sequence shown in SEQ ID NO: 31.

In one embodiment, the polynucleotide of the invention comprises a nucleotide sequence described in (a) and/or (b) below:

(a) a nucleotide sequence encoding a heavy chain consisting of the amino acid sequence shown in SEQ ID NO: 34; and/or (b) a nucleotide sequence encoding a light chain consisting of the amino acid sequence shown in SEQ ID NO: 36.

The polynucleotide comprising a nucleotide sequence encoding a heavy chain consisting of the amino acid sequence shown in SEQ ID NO: 34 includes, for example, a polynucleotide comprising the nucleotide sequence shown in SEQ ID NO: 33.

The polynucleotide comprising a nucleotide sequence encoding a light chain consisting of the amino acid sequence shown in SEQ ID NO: 36 includes, for example, polynucleotide comprising the nucleotide sequence shown in SEQ ID NO: 35.

In one embodiment, the polynucleotide of the invention comprises a nucleotide sequence described in (a) and/or (b) below:

(a) a nucleotide sequence encoding a heavy chain consisting of the amino acid sequence shown in SEQ ID NO: 38; and/or (b) a nucleotide sequence encoding a light chain consisting of the amino acid sequence shown in SEQ ID NO: 40.

The polynucleotide comprising a nucleotide sequence encoding a heavy chain consisting of the amino acid sequence shown in SEQ ID NO: 38 includes, for example, a polynucleotide comprising the nucleotide sequence shown in SEQ ID NO: 37.

The polynucleotide comprising a nucleotide sequence encoding a light chain consisting of amino acid sequence shown in SEQ ID NO: 40 includes, for example, a polynucleotide comprising a nucleotide sequence shown in SEQ ID NO: 39.

In one embodiment, the polynucleotide of the invention may further comprise a nucleotide sequence encoding an Fc polypeptide, and in one embodiment, the polynucleotide of the invention may comprise a nucleotide sequence encoding an Fc polypeptide consisting of the amino acid sequence shown in SEQ ID NO: 42.

In one embodiment, the polynucleotide of the invention comprises a nucleotide sequence described in (a) and/or (b) and (c) below:

(a) a nucleotide sequence encoding a heavy chain consisting of the amino acid sequence shown in SEQ ID NO: 22;

(b) a nucleotide sequence encoding a light chain consisting of the amino acid sequence shown in SEQ ID NO: 24.

(c) a nucleotide sequence encoding an Fc polypeptide consisting of the amino acid sequence shown in SEQ ID NO: 42.

The polynucleotide comprising a nucleotide sequence encoding a heavy chain consisting of the amino acid sequence shown in SEQ ID NO: 22 includes, for example, a polynucleotide comprising a nucleotide sequence shown in SEQ ID NO: 21.

The polynucleotides comprising a nucleotide sequence encoding a light chain consisting of the amino acid sequence shown in SEQ ID NO: 24 includes, for example, a polynucleotide comprising a nucleotide sequence shown in SEQ ID NO: 23.

In one embodiment, the polynucleotide of the invention is a polynucleotide comprising a nucleotide sequence encoding a heavy chain of and/or a nucleotide sequence encoding a light chain of a one-armed anti-human NR1 antibody, wherein the antibody binds to human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR cell internalization by a pathogenic anti-human NR1 antibody derived from an anti-NMDAR encephalitis patient.

The polynucleotide of the invention can be easily produced by a person skilled in the art based on its nucleotide sequence and by using methods well known in the art. For example, the polynucleotide of the invention can be synthesized by utilizing gene synthesis methods known in the art. Such gene synthesis methods which can be used include a variety of methods known to a person skilled in the art, such as a method for synthesizing antibody genes described in WO90/07861.

Expression Vector of the Invention

An expression vector of the invention includes an expression vector comprising a polynucleotide comprising a nucleotide sequence encoding a heavy chain variable region of a one-armed anti-human antibody, an expression vector comprising a polynucleotide comprising a nucleotide sequence encoding a light chain variable region of a one-armed anti-human antibody, and an expression vector comprising the polynucleotide comprising the nucleotide sequence encoding the heavy chain variable region of the one-armed anti-human antibody of the invention and the polynucleotide comprising the nucleotide sequence encoding the light chain variable region of the antibody. Moreover, the expression vector of the invention includes an expression vector comprising a polynucleotide comprising a nucleotide sequence encoding a heavy chain of the one-armed anti-human antibody of the invention, an expression vector comprising a polynucleotide comprising a nucleotide sequence encoding a light chain of the one-armed anti-human antibody of the invention, and an expression vector comprising the polynucleotide comprising the nucleotide sequence encoding the heavy chain of the one-armed anti-human antibody of the invention and the polynucleotide comprising the nucleotide sequence encoding the light chain of the antibody. The expression vector of the invention may include a polynucleotide comprising a nucleotide sequence encoding an Fc polypeptide.

In one embodiment, the expression vector of the invention comprises a polynucleotide comprising a nucleotide sequence encoding a heavy chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, and/or a polynucleotide comprising a nucleotide sequence encoding a light chain variable region comprising CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4. In one embodiment, the expression vector of the invention comprises a polynucleotide comprising a nucleotide sequence encoding a heavy chain variable region consisting of an amino acid sequence shown in SEQ ID NO: 2 and/or a polynucleotide comprising a nucleotide sequence encoding a light chain variable region consisting of the amino acid sequence shown in SEQ ID NO: 4. In one embodiment, the expression vector of the invention comprises a polynucleotide comprising a nucleotide sequence encoding a heavy chain comprising a heavy chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, and/or a polynucleotide comprising a nucleotide sequence encoding a light chain comprising a light chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4. In one embodiment, the expression vector of the invention comprises a polynucleotide comprising a nucleotide sequence encoding a heavy chain comprising a heavy chain variable region consisting of the amino acid sequence shown in SEQ ID NO: 2, and/or a polynucleotide comprising a nucleotide sequence encoding a light chain comprising a light chain variable region consisting of the amino acid sequence shown in SEQ ID NO: 4. In one embodiment, the expression vector of the invention comprises a polynucleotide comprising a nucleotide sequence encoding a heavy chain consisting of the amino acid sequence shown in SEQ ID NO: 22 and/or a polynucleotide comprising a nucleotide sequence encoding a light chain consisting of the amino acid sequence shown in SEQ ID NO: 24.

In one embodiment, the expression vector of the invention comprises a polynucleotide comprising a nucleotide sequence encoding a heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, and/or a polynucleotide comprising a nucleotide sequence encoding a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8. In one embodiment, the expression vector of the invention comprises a polynucleotide comprising a nucleotide sequence encoding a heavy chain variable region consisting of the amino acid sequence shown in SEQ ID NO: 6, and/or a polynucleotide comprising a nucleotide sequence encoding a light chain variable region consisting of the amino acid sequence shown in SEQ ID NO: 8. In one embodiment, the expression vector of the invention comprises a polynucleotide comprising a nucleotide sequence encoding a heavy chain comprising a heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, and/or a polynucleotide comprising a nucleotide sequence encoding a light chain comprising a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8. In one embodiment, the expression vector of the invention comprises a polynucleotide comprising a nucleotide sequence encoding a heavy chain comprising a heavy chain variable region consisting of the amino acid sequence shown in SEQ ID NO: 6, and/or a polynucleotide comprising a nucleotide sequence encoding a light chain comprising a light chain variable region consisting of the amino acid sequence shown in SEQ ID NO: 8. In one embodiment, the expression vector of the invention comprises a polynucleotide comprising a nucleotide sequence encoding a heavy chain consisting of the amino acid sequence shown in SEQ ID NO: 26 and/or a polynucleotide comprising a nucleotide sequence encoding a light chain consisting of the amino acid sequence shown in SEQ ID NO: 28.

In one embodiment, the expression vector of the invention comprises a polynucleotide comprising a nucleotide sequence encoding a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, and/or a polynucleotide comprising a nucleotide sequence encoding a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12.

In one embodiment, the expression vector of the invention comprises a polynucleotide comprising a nucleotide sequence encoding a heavy chain variable region consisting of an amino acid sequence shown in SEQ ID NO: 10, and/or a polynucleotide comprising a nucleotide sequence encoding a light chain variable region consisting of an amino acid sequence shown in SEQ ID NO: 12. In one embodiment, the expression vector of the invention comprises a polynucleotide comprising a nucleotide sequence encoding a heavy chain comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, and/or a polynucleotide comprising a nucleotide sequence encoding a light chain comprising a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12. In one embodiment, the expression vector of the invention comprises a polynucleotide comprising a nucleotide sequence encoding a heavy chain comprising a heavy chain variable region consisting of the amino acid sequence shown in SEQ ID NO: 10 and/or a polynucleotide comprising a nucleotide sequence encoding a light chain comprising a light chain variable region consisting of the amino acid sequence shown in SEQ ID NO: 12. In one embodiment, the expression vector of the invention comprises a polynucleotide comprising a nucleotide sequence encoding a heavy chain consisting of the amino acid sequence shown in SEQ ID NO: 30, and/or a polynucleotide comprising a nucleotide sequence encoding a light chain consisting of the amino acid sequence shown in SEQ ID NO: 32.

In one embodiment, the expression vector of the invention comprises a polynucleotide comprising a nucleotide sequence encoding a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, and/or a polynucleotide comprising a nucleotide sequence encoding a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16. In one embodiment, the expression vector of the invention comprises a polynucleotide comprising a nucleotide sequence encoding a heavy chain variable region consisting of the amino acid sequence shown in SEQ ID NO: 14, and/or a polynucleotide comprising a nucleotide sequence encoding a light chain variable region consisting of the amino acid sequence shown in SEQ ID NO: 16. In one embodiment, the expression vector of the invention comprises a polynucleotide comprising a nucleotide sequence encoding a heavy chain comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, and/or a polynucleotide comprising a nucleotide sequence encoding a light chain comprising a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16. In one embodiment, the expression vector of the invention comprises a polynucleotide comprising a nucleotide sequence encoding a heavy chain comprising a heavy chain variable region consisting of the amino acid sequence shown in SEQ ID NO: 14, and/or a polynucleotide comprising a nucleotide sequence encoding a light chain comprising a light chain variable region consisting of the amino acid sequence shown in SEQ ID NO: 16. In one embodiment, the expression vector of the invention comprises a polynucleotide comprising a nucleotide sequence encoding a heavy chain consisting of the amino acid sequence shown in SEQ ID NO: 34, and/or a polynucleotide comprising a nucleotide sequence encoding a light chain consisting of the amino acid sequence shown in SEQ ID NO: 36.

In one embodiment, the expression vector of the invention comprises a polynucleotide comprising a nucleotide sequence encoding a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, and/or a polynucleotide comprising a nucleotide sequence encoding a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20. In one embodiment, the expression vector of the invention comprises a polynucleotide comprising a nucleotide sequence encoding a heavy chain variable region consisting of the amino acid sequence shown in SEQ ID NO: 18 and/or a polynucleotide comprising a nucleotide sequence encoding a light chain variable region consisting of the amino acid sequence shown in SEQ ID NO: 20. In one embodiment, the expression vector of the invention comprises a polynucleotide comprising a nucleotide sequence encoding a heavy chain comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, and/or a polynucleotide comprising a nucleotide sequence encoding a light chain comprising a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20. In one embodiment, the expression vector of the invention comprises a polynucleotide comprising a nucleotide sequence encoding a heavy chain comprising a heavy chain variable region consisting of the amino acid sequence shown in SEQ ID NO: 18, and/or a polynucleotide comprising a nucleotide sequence encoding a light chain comprising a light chain variable region consisting of the amino acid sequence shown in SEQ ID NO: 20. In one embodiment, the expression vector of the invention comprises a polynucleotide comprising a nucleotide sequence encoding a heavy chain consisting of the amino acid sequence shown in SEQ ID NO: 38, and/or a polynucleotide comprising a nucleotide sequence encoding a light chain consisting of the amino acid sequence shown in SEQ ID NO: 40.

In one embodiment, the expression vector of the invention may further comprise a polynucleotide comprising a nucleotide sequence encoding an Fc polypeptide. In one embodiment, the expression vector of the invention may further comprise a polynucleotide comprising a nucleotide sequence encoding an Fc polypeptide shown in SEQ ID NO: 42.

In one embodiment, the expression vector of the invention is an expression vector comprising a polynucleotide comprising a nucleotide sequence encoding a heavy chain of a one-armed anti-human NR1 antibody and/or a polynucleotide comprising a nucleotide sequence encoding a light chain of the antibody, wherein the antibody binds to human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR cell internalization by a pathogenic anti-human NR1 antibody derived from an anti-NMDAR encephalitis patient.

In one embodiment, the expression vector of the invention is an expression vector comprising a polynucleotide comprising a nucleotide sequence encoding a heavy chain of a one-armed anti-human NR1 antibody and/or a polynucleotide comprising a nucleotide sequence encoding a light chain of the antibody, and an Fc polypeptide of the antibody, wherein the antibody that binds to human NRA competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits an NMDAR cell internalization by a pathogenic anti-human NR1 antibody derived from an anti-NMDAR encephalitis patient.

The expression vector used for expressing the polynucleotide of the invention includes, but not limited to, those that can express, in various kinds of host cells such as eukaryotic cells (e.g. animal cells, insect cells, plant cells, and yeast) and/or prokaryotic cells (e.g. E. coli), a polynucleotide comprising a nucleotide sequence encoding a heavy chain of the one-armed anti-human NR1 antibody of the invention, a polynucleotide comprising a nucleotide sequence encoding a light chain of the one-armed anti-human NR1 antibody of the invention, or a polynucleotide comprising a nucleotide sequence encoding an Fc polypeptide which binds to the heavy chain to form an Fc region, and produce the polypeptide encoded by them. Such an expression vector includes, for example, plasmid vector, viral vector (e.g., adenovirus and retrovirus), etc. In one embodiment, pEE6.4 or pEE12.4 (Lonza) can be used as expression vectors.

The expression vector of the invention may comprise a promoter operably coupled to the polynucleotide of the invention. The promoter for expressing the polynucleotide of the invention in animal cell includes, for example, viral-derived promoters, such as CMV, RSV, and SV40, actin promoter, EF (elongation factor) 1 alpha promoter, heat shock promoter, etc. The promoter for expressing the polynucleotide of the invention in bacteria (e.g., *Escherichia coli*) includes, for example, trp promoter, lac promoter, λPL promoter, tac promoter, etc. The promoter for expressing the polynucleotide of the invention in yeast includes, for example, GAL 1 promoter, GAL 10 promoter, PH05 promoter, PGK promoter, GAP promoter, ADH promoter, etc.

When using an animal cell, an insect cell, or yeast as a host cell, the expression vector of the invention may include start codon, stop codon, enhancer sequence, 5' and 3' untranslated region of the gene encoding the present one-armed anti-human NR1 antibody or its heavy chain or light chain, a secretion signal sequence, a splice junction, a polyadenylation site, or a replicable unit, etc. When using *E. coli* as a host cell, the expression vector of the invention may include start codon, stop codon, terminator region, and replicable unit. The expression vector of the invention may include selective markers generally used depending on the purpose (e.g., tetracycline-resistance gene, ampicillin-resistant gene, kanamycin-resistant gene, neomycin resistance gene, and dihydrofolate-reductase gene).

<Transformed Host Cell of the Invention>

A transformed host cell of the invention comprises a transformed host cell with the expression vector of the invention. The transformed host cell of the invention includes a host cell selected from the group consisting of (1)-(4) below:

(1) a transformed host cell with the expression vector comprising a polynucleotide comprising a nucleotide sequence encoding a heavy chain variable region of the one-armed anti-human NR1 antibody of the invention;

(2) a transformed host cell with the expression vector comprising a polynucleotide comprising a nucleotide sequence encoding a light chain variable region of the one-armed anti-human NR1 antibody of the invention;

(3) a transformed host cell with the expression vector comprising a polynucleotide comprising a nucleotide sequence encoding a heavy chain variable region of the one-armed anti-human NR1 antibody of the invention, and a polynucleotide comprising a nucleotide sequence encoding a light chain variable region of the antibody;

(4) a transformed host cell with the expression vector comprising a polynucleotide comprising a nucleotide sequence encoding a heavy chain variable region of the one-armed anti-human NR1 antibody of the invention, and the expression vector comprising a polynucleotide comprising a nucleotide sequence encoding a light chain variable region of the antibody.

The transformed host cell of the invention also includes a host cell selected from the group consisting of (a)-(d) below:

(a) a transformed host cell with the expression vector comprising a polynucleotide comprising a nucleotide sequence encoding a heavy chain of the one-armed anti-human NR1 antibody of the invention;

(b) a transformed host cell with the expression vector comprising a polynucleotide comprising a nucleotide sequence encoding a light chain of the one-armed anti-human NR1 antibody of the invention;

(c) a transformed host cell with the expression vector comprising a polynucleotide comprising a nucleotide sequence encoding a heavy chain of the one-armed anti-human NR1 antibody of the invention, and a polynucleotide comprising a nucleotide sequence encoding a light chain of the antibody;

(d) a transformed host cell with the expression vector comprising a polynucleotide comprising a nucleotide sequence encoding a heavy chain of the one-armed anti-human NR1 antibody of the invention of the invention, and the expression vector comprising a polynucleotide comprising a nucleotide sequence encoding a light chain of the antibody.

In one embodiment, the expression vector included in the host cell in the above-mentioned (a)-(d) may further comprise a polynucleotide comprising a nucleotide sequence encoding an Fc polypeptide. In one embodiment, the host cell in the above-mentioned (a)-(d) may further comprise an expression vector comprising a polynucleotide comprising a nucleotide sequence encoding an Fc polypeptide.

Examples of the transformed host cell of the invention includes a transformed host cell with a polynucleotide comprising a nucleotide sequence encoding a heavy chain of the one-armed anti-human NR1 antibody of the invention, a polynucleotide comprising a nucleotide sequence encoding a light chain of the antibody, and an expression vector comprising a polynucleotide comprising a nucleotide sequence encoding an Fc polypeptide of the antibody; a transformed host cell with an expression vector comprising a polynucleotide comprising a nucleotide sequence encoding a heavy chain of the one-armed anti-human NR1 antibody of the invention, an expression vector comprising a polynucleotide comprising a nucleotide sequence encoding a light chain of the antibody, and an expression vector comprising a polynucleotide comprising a nucleotide sequence encoding an Fc polypeptide of the antibody; and a transformed host cell with an expression vector comprising a polynucleotide comprising a nucleotide sequence encoding a heavy chain of the one-armed anti-human NR1 antibody of the invention and a polynucleotide comprising a nucleotide sequence encoding a light chain of the antibody, and an expression vector comprising a polynucleotide comprising a nucleotide sequence encoding an Fc polypeptide of the antibody.

In one embodiment, the host cell of the invention is a transformed host cell with an expression vector selected from (a)-(d) below:

(a) an expression vector comprising a polynucleotide comprising a nucleotide sequence encoding a heavy chain variable region of the one-armed anti-human NR1 antibody of the invention set forth in any of the following (1) to (8);

(b) an expression vector comprising a polynucleotide comprising a nucleotide sequence encoding a light chain variable region of the one-armed anti-human NR1 antibody of the invention set forth in any of the following (1) to (8);

(c) an expression vector comprising a polynucleotide comprising a nucleotide sequence encoding a heavy chain variable region of the one-armed anti-human NR1 antibody of the invention set forth in any of the following (1) to (8) and a polynucleotide comprising a nucleotide sequence encoding a light chain variable region of the antibody;

(d) an expression vector comprising a polynucleotide comprising a nucleotide sequence encoding a heavy chain variable region of the one-armed anti-human NR1 antibody of the invention set forth in any of the following (1) to (8), and an expression vector comprising a polynucleotide comprising a nucleotide sequence encoding a light chain variable region of the antibody:

(1) a one-armed anti-human NR1 antibody comprising a heavy chain variable region comprising a CDR1 consisting of the amino acid sequence of amino acid numbers 31 to 35 of SEQ ID NO: 6, a CDR2 consisting of the amino acid sequence of amino acid numbers 50 to 60 of SEQ ID NO: 6, and a CDR3 consisting of the amino acid sequence of amino acid numbers 99 to 110 of SEQ ID NO: 6, and a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8;

(2) a one-armed anti-human NR1 antibody comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, and a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12;

(3) a one-armed anti-human NR1 antibody comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, and a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16;

(4) a one-armed one anti-human NR1 antibody comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, and a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20;

(5) a one-armed anti-human NR1 antibody comprising a heavy chain variable region consisting of the amino acid sequence shown in SEQ ID NO: 6, and a light chain variable region consisting of the amino acid sequence shown in SEQ ID NO: 8;

(6) a one-armed anti-human NR1 antibody comprising a heavy chain variable region consisting of the amino acid sequence shown in SEQ ID NO: 10, and a light chain variable region consisting of the amino acid sequence shown in SEQ ID NO: 12;

(7) a one-armed anti-human NR1 antibody comprising a heavy chain variable region consisting of the amino acid sequence shown in SEQ ID NO: 14, and a light chain variable region consisting of the amino acid sequence shown in SEQ ID NO: 16;

(8) a one-armed anti-human NR1 antibody comprising a heavy chain variable region consisting of the amino acid sequence shown in SEQ ID NO: 18, and a light chain variable region consisting of the amino acid sequence shown in SEQ ID NO: 20.

In one embodiment, the host cell of the invention is a transformed host cell with an expression vector selected from:

(a) an expression vector comprising a polynucleotide comprising a nucleotide sequence encoding a heavy chain of the one-armed anti-human NR1 antibody of the invention set forth in any of the following (1) to (8);

(b) an expression vector comprising a polynucleotide comprising a nucleotide sequence encoding a light chain of the one-armed anti-human NR1 antibody of the invention set forth in any of the following (1) to (8);

(c) an expression vector comprising a polynucleotide comprising a nucleotide sequence encoding a heavy chain of the one-armed anti-human NR1 antibody of the invention set forth in any of the following (1) to (8) and a polynucleotide comprising a nucleotide sequence encoding a light chain variable region of the antibody;

(d) an expression vector comprising a polynucleotide comprising a nucleotide sequence encoding a heavy chain of the one-armed anti-human NR1 antibody of the invention set forth in any of the following (1) to (8) and an expression vector comprising a polynucleotide comprising a nucleotide sequence encoding a light chain of the antibody:

(1) a one-armed anti-human NR1 antibody comprising a heavy chain comprising heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, a light chain comprising a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8, as well as an Fc polypeptide;

(2) a one-armed anti-human NR1 antibody comprising a heavy chain comprising a heavy chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10; a light chain comprising a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12; and an Fc polypeptide;

(3) a one-armed anti-human NR1 antibody comprising a heavy chain comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14; a light chain comprising a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16, as well as an Fc polypeptide;

(4) a one-armed anti-human NR1 antibody comprising a heavy chain comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18; a light chain comprising a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20; and an Fc polypeptide;

(5) a one-armed anti-human NR1 antibody comprising a heavy chain comprising a heavy chain variable region consisting of the amino acid sequence shown in SEQ ID NO: 6, a light chain comprising a light chain variable region consisting of the amino acid sequence shown in SEQ ID NO: 8, and an Fc polypeptide;

(6) one anti-human NR1 antibody comprising a heavy chain comprising a heavy chain variable region consisting of the amino acid sequence shown in SEQ ID NO: 10, a light chain comprising a light chain variable region consisting of the amino acid sequence shown in SEQ ID NO: 12, and an Fc polypeptide;

(7) a one-armed anti-human NR1 antibody comprising a heavy chain comprising a heavy chain variable region consisting of the amino acid sequence shown in SEQ ID NO: 14, a light chain comprising a light chain variable region consisting of the amino acid sequence shown in SEQ ID NO: 16, and an Fc polypeptide;

(8) one anti-human NR1 antibody comprising a heavy chain comprising a heavy chain variable region consisting of the amino acid sequence shown in SEQ ID NO: 18, a light chain comprising a light chain variable region consisting of the amino acid sequence shown in SEQ ID NO: 20, and an Fc polypeptide.

In one embodiment, the host cell of the invention is a transformed host cell with an expression vector selected from (a)-(i) below:

(a) an expression vector comprising a polynucleotide comprising a nucleotide sequence encoding a heavy chain of the one-armed anti-human NR1 antibody of the invention set forth in any of the following (1) to (10) and an expression vector comprising a polynucleotide comprising a nucleotide sequence encoding an Fc polypeptide of the antibody;

(b) an expression vector comprising a polynucleotide comprising a nucleotide sequence encoding a light chain of the one-armed anti-human NR1 antibody of the invention set forth in any of the following (1) to (10) and an expression vector comprising a polynucleotide comprising a nucleotide sequence encoding an Fc polypeptide of the antibody;

(c) an expression vector comprising a polynucleotide comprising a nucleotide sequence encoding a heavy chain of the one-armed anti-human NR1 antibody of the invention set forth in any of the following (1) to (10) and a polynucleotide comprising a nucleotide sequence encoding a light chain of the antibody, as well as an expression vector comprising a polynucleotide comprising a nucleotide sequence encoding an Fc polypeptide of the antibody;

(d) an expression vector comprising a polynucleotide comprising a nucleotide sequence encoding a heavy chain of the one-armed anti-human NR1 antibody of the invention set forth in any of the following (1) to (10), an expression vector comprising a polynucleotide comprising a nucleotide sequence encoding a light chain of the antibody, and an expression vector comprising a polynucleotide comprising a nucleotide sequence encoding an Fc polypeptide of the antibody;

(e) an expression vector comprising a polynucleotide comprising a nucleotide sequence encoding a heavy chain of the one-armed anti-human NR1 antibody of the invention set forth in any of the following (1) to (10) and a polynucleotide comprising a nucleotide sequence encoding an Fc polypeptide of the antibody;

(f) an expression vector comprising a polynucleotide comprising a nucleotide sequence encoding a light chain of the one-armed anti-human NR1 antibody of the invention set forth in any of the following (1) to (10) as well as a polynucleotide comprising a nucleotide sequence encoding an Fc polypeptide of the antibody;

(g) an expression vector comprising a polynucleotide comprising a nucleotide sequence encoding a heavy chain of the one-armed anti-human NR1 antibody of the invention set forth in any of the following (1) to (10) and a polynucleotide comprising a nucleotide sequence encoding an Fc polypeptide of the antibody, as well as an expression vector comprising a polynucleotide comprising a nucleotide sequence encoding a light chain of the antibody;

(h) an expression vector comprising a polynucleotide comprising a nucleotide sequence encoding a heavy chain of the one-armed anti-human NR1 antibody of the invention set forth in any of the following (1) to (10), as well as an expression vector comprising a polynucleotide comprising a nucleotide sequence encoding a light chain of the antibody and a polynucleotide comprising a nucleotide sequence encoding an Fc polypeptide of the antibody;

(i) an expression vector comprising a polynucleotide comprising a nucleotide sequence encoding a heavy chain of the one-armed anti-human NR1 antibody of the invention set forth in any of the following (1) to (10), a polynucleotide comprising a nucleotide sequence encoding a light chain of the antibody, and a polynucleotide comprising a nucleotide sequence encoding an Fc polypeptide of the antibody:

(1) a one-armed anti-human NR1 antibody comprising a heavy chain comprising a heavy chain variable region comprising a CDR1 consisting of the amino acid sequence of amino acid numbers consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2; a light chain comprising a light chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4; and an Fc polypeptide;

(2) a one-armed anti-human NR1 antibody comprising a heavy chain comprising heavy chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6; a light chain comprising a light chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8; and an Fc polypeptide;

(3) a one-armed anti-human NR1 antibody comprising a heavy chain comprising a heavy chain variable region comprising CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10; a light chain comprising a light chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12; and an Fc polypeptide;

(4) a one-armed anti-human NR1 antibody comprising a heavy chain comprising a heavy chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14; a light chain comprising a light chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16; and an Fc polypeptide;

(5) a one-armed anti-human NR1 antibody comprising a heavy chain comprising a heavy chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18; a light chain comprising a light chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20; and an Fc polypeptide;

(6) a one-armed anti-human NR1 antibody comprising a heavy chain comprising a heavy chain variable region consisting of the amino acid sequence shown in SEQ ID NO: 2, a light chain comprising a light chain variable region consisting of the amino acid sequence shown in SEQ ID NO: 4, and an F polypeptide;

(7) a one-armed anti-human NR1 antibody comprising a heavy chain comprising a heavy chain variable region consisting of the amino acid sequence shown in SEQ ID NO: 6, a light chain comprising a light chain variable region consisting of the amino acid sequence shown in SEQ ID NO: 8, and an Fc polypeptide;

(8) a one-armed anti-human NR1 antibody comprising a heavy chain comprising a heavy chain variable region consisting of the amino acid sequence shown in SEQ ID NO: 10, a light chain comprising a light chain variable region consisting of the amino acid sequence shown in SEQ ID NO: 12, and an Fc polypeptide;

(9) a one-armed anti-human NR1 antibody comprising a heavy chain comprising a heavy chain variable region consisting of the amino acid sequence shown in SEQ ID NO: 14, a light chain comprising a light chain variable region consisting of the amino acid sequence shown in SEQ ID NO: 16, and an Fc polypeptide;

(10) a one-armed anti-human NR1 antibody comprising a heavy chain comprising a heavy chain variable region consisting of the amino acid sequence shown in SEQ ID NO: 18, a light chain comprising a light chain variable region consisting of the amino acid sequence shown in SEQ ID NO: 20, and an Fc polypeptide.

In one embodiment, the host cell of the invention is a transformed host cell with an expression vector selected from (a)-(i) below:

(a) an expression vector comprising a polynucleotide comprising a nucleotide sequence encoding a heavy chain consisting of the amino acid sequence shown in SEQ ID NO: 22, and an expression vector comprising a polynucleotide comprising a nucleotide sequence encoding an Fc polypeptide consisting of the amino acid sequence shown in SEQ ID NO: 42;

(b) an expression vector comprising a polynucleotide comprising a nucleotide sequence encoding a heavy chain consisting of the amino acid sequence shown in SEQ ID NO: 22 and a polynucleotide comprising a nucleotide sequence encoding an Fc polypeptide consisting of the amino acid sequence shown in SEQ ID NO: 42;

(c) an expression vector comprising a polynucleotide comprising a nucleotide sequence encoding a light chain consisting of the amino acid sequence shown in SEQ ID NO: 24, and an expression vector comprising a polynucleotide comprising a nucleotide sequence encoding an Fc polypeptide consisting of the amino acid sequence shown in SEQ ID NO: 42;

(d) an expression vector comprising a polynucleotide comprising a nucleotide sequence encoding a light chain consisting of the amino acid sequence shown in SEQ ID NO: 24 and a polynucleotide comprising a nucleotide sequence encoding an Fc polypeptide consisting of the amino acid sequence shown in SEQ ID NO: 42;

(e) an expression vector comprising a polynucleotide comprising a nucleotide sequence encoding a heavy chain consisting of the amino acid sequence shown in SEQ ID NO: 22 and a polynucleotide comprising a nucleotide sequence encoding a light chain consisting of the amino acid sequence shown in SEQ ID NO: 24, as well as an expression vector comprising a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a heavy chain consisting of the amino acid sequence shown in SEQ ID NO: 22 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 24;

(g) an expression vector comprising a polynucleotide comprising a nucleotide sequence encoding a heavy chain consisting of the amino acid sequence shown in SEQ ID NO: 22, as well as an expression vector comprising a polynucleotide comprising a nucleotide sequence encoding a light chain consisting of the amino acid sequence shown in SEQ ID NO: 24 and a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a heavy chain consisting of the amino acid sequence shown in SEQ ID NO: 22, an expression vector comprising a polynucleotide comprising a nucleotide sequence encoding a light chain consisting of the amino acid sequence shown in SEQ ID NO: 24 and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 22, a polynucleotide comprising a nucleotide sequence encoding a light chain consisting of the amino acid sequence shown in SEQ ID NO: 24, and a polynucleotide comprising a nucleotide sequence encoding an Fc polypeptide consisting of the amino acid sequence shown in SEQ ID NO: 42.

In one embodiment, the host cell of the invention is a transformed host cell with an expression vector or vectors selected from:

(a) an expression vector comprising a polynucleotide comprising a nucleotide sequence encoding a heavy chain consisting of the amino acid sequence shown in SEQ ID NO: 26;

(b) an expression vector comprising a polynucleotide comprising a nucleotide sequence encoding a light chain consisting of the amino acid sequence shown in SEQ ID NO: 28;

(c) an expression vector comprising a polynucleotide comprising a nucleotide sequence encoding a heavy chain consisting of the amino acid sequence shown in SEQ ID NO: 26 and a polynucleotide comprising a nucleotide sequence encoding a light chain consisting of the amino acid sequence shown in SEQ ID NO: 28;

(d) an expression vector comprising a polynucleotide comprising a nucleotide sequence encoding a heavy chain consisting of the amino acid sequence shown in SEQ ID NO: 26, and an expression vector comprising a polynucleotide comprising a nucleotide sequence encoding a light chain consisting of the amino acid sequence shown in SEQ ID NO: 28;

(e) an expression vector comprising a polynucleotide comprising a nucleotide sequence encoding a heavy chain consisting of the amino acid sequence shown in SEQ ID NO: 26, and a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a light chain consisting of the amino acid sequence shown in SEQ ID NO: 28 and a polynucleotide comprising a nucleotide sequence encoding an Fc polypeptide consisting of the amino acid sequence shown in SEQ ID NO: 42;

(g) an expression vector comprising a polynucleotide comprising a nucleotide sequence encoding a heavy chain consisting of the amino acid sequence shown in SEQ ID NO: 26, and an expression vector comprising a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a light chain consisting of the amino acid sequence shown in SEQ ID NO: 28, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 26 and a polynucleotide comprising a nucleotide sequence encoding a light chain consisting of the amino acid sequence shown in SEQ ID NO: 28, as well as an expression vector comprising a polynucleotide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 26 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 28;

(k) an expression vector comprising a polynucleotide comprising a nucleotide sequence encoding a heavy chain consisting of the amino acid sequence shown in SEQ ID NO: 26, as well as an expression vector comprising a polynucleotide comprising a nucleotide sequence encoding a light chain consisting of the amino acid sequence shown in SEQ ID NO: 28 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 26, an expression vector comprising a polynucleotide comprising a nucleotide sequence encoding a light chain consisting of the amino acid sequence shown in SEQ ID NO: 28, and an expression vector comprising polynucleotide comprising a nucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 26, a polynucleotide comprising a nucleotide sequence encoding a light chain consisting of the amino acid sequence shown in SEQ ID NO: 28, and a polynucleotide comprising a nucleotide sequence encoding an Fc polypeptide consisting of the amino acid sequence shown in SEQ ID NO: 42.

In one embodiment, a host cell of the invention is a transformed host cell with an expression vector or vectors selected from:

(a) an expression vector comprising a polynucleotide comprising a nucleotide sequence encoding a heavy chain consisting of the amino acid sequence shown in SEQ ID NO: 30;

(b) an expression vector comprising a polynucleotide comprising a nucleotide sequence encoding a light chain consisting of the amino acid sequence shown in SEQ ID NO: 32;

(c) an expression vector comprising a polynucleotide comprising a nucleotide sequence encoding a heavy chain consisting of the amino acid sequence shown in SEQ ID NO: 30 and a polynucleotide comprising a nucleotide sequence encoding a light chain consisting of the amino acid sequence shown in SEQ ID NO: 32;

(d) an expression vector comprising a polynucleotide comprising a nucleotide sequence encoding a heavy chain consisting of the amino acid sequence shown in SEQ ID NO: 30, and an expression vector comprising a polynucleotide comprising a nucleotide sequence encoding a light chain consisting of the amino acid sequence shown in SEQ ID NO: 32;

(e) an expression vector comprising a polynucleotide comprising a nucleotide sequence encoding a heavy chain consisting of the amino acid sequence shown in SEQ ID NO: 30 and a polynucleotide comprising a nucleotide sequence encoding an Fc polypeptide con-
sisting of the amino acid sequence shown in SEQ ID
NO: 42;
(f) an expression vector comprising a polynucleotide
comprising a nucleotide sequence encoding a light
chain consisting of the amino acid sequence shown in
SEQ ID NO: 32 and a polynucleotide comprising a
nucleotide sequence encoding an Fc polypeptide con-
sisting of the amino acid sequence shown in SEQ ID
NO: 42;
(g) an expression vector comprising a polynucleotide
comprising a nucleotide sequence encoding a heavy
chain consisting of the amino acid sequence shown in
SEQ ID NO: 30, and an expression vector comprising
a polynucleotide comprising a nucleotide sequence
encoding an Fc polypeptide consisting of the amino
acid sequence shown on SEQ ID NO: 42;
(h) an expression vector comprising a polynucleotide
comprising a nucleotide sequence encoding a light
chain consisting of the amino acid sequence shown in
SEQ ID NO: 32, and an expression vector comprising
a polynucleotide comprising a nucleotide sequence
encoding an Fc polypeptide consisting of the amino
acid sequence shown in SEQ ID NO: 42;
(i) an expression vector comprising a polynucleotide
comprising a nucleotide sequence encoding a heavy
chain consisting of the amino acid sequence shown in
SEQ ID NO: 30 and a polynucleotide comprising a
nucleotide sequence encoding a light chain consisting
of the amino acid sequence shown in SEQ ID NO: 32,
as well as an expression vector comprising a polynucle-
otide comprising a nucleotide sequence encoding an Fc
polypeptide consisting of the amino acid sequence
shown in SEQ ID NO: 42;
(j) an expression vector comprising a polynucleotide
comprising a nucleotide sequence encoding a heavy
chain consisting of the amino acid sequence shown in
SEQ ID NO: 30 and a polynucleotide comprising a
nucleotide sequence encoding an Fc polypeptide con-
sisting of the amino acid sequence shown in SEQ ID
NO: 42, as well an expression vector comprising a
polynucleotide comprising a nucleotide sequence
encoding a light chain consisting of the amino acid
sequence shown in SEQ ID NO: 32;
(k) an expression vector comprising a polynucleotide
comprising a nucleotide sequence encoding a heavy
chain consisting of the amino acid sequence shown in
SEQ ID NO: 30, as well as an expression vector
comprising a polynucleotide comprising a nucleotide
sequence encoding a light chain consisting of the amino
acid sequence shown in SEQ ID NO: 32 and a poly-
nucleotide comprising a nucleotide sequence encoding
an Fc polypeptide consisting of the amino acid
sequence shown in SEQ ID NO: 42;
(l) an expression vector comprising a polynucleotide
comprising a nucleotide sequence encoding a heavy
chain consisting of the amino acid sequence shown in
SEQ ID NO: 30, an expression vector comprising a
polynucleotide comprising a nucleotide sequence
encoding a light chain consisting of the amino acid
sequence shown in SEQ ID NO: 32, and an expression
vector comprising a polynucleotide sequence encoding
an Fc polypeptide consisting of the amino acid
sequence shown in SEQ ID NO: 42;
(m) an expression vector comprising a polynucleotide
comprising a nucleotide sequence encoding a heavy
chain consisting of the amino acid sequence shown in SEQ ID NO: 30, polynucleotide comprising a nucleo-
tide sequence encoding a light chain consisting of the
amino acid sequence shown in SEQ ID NO: 32, and a
polynucleotide comprising a nucleotide sequence
encoding an Fc polypeptide consisting of the amino
acid sequence shown in SEQ ID NO: 42.
In one embodiment, the host cell of the invention is a
transformed host cell with an expression vector or vectors
selected from:
(a) an expression vector comprising a polynucleotide
comprising a nucleotide sequence encoding a heavy
chain consisting of the amino acid sequence shown in
SEQ ID NO: 34;
(b) an expression vector comprising a polynucleotide
comprising a nucleotide sequence encoding a light
chain consisting of the amino acid sequence shown in
SEQ ID NO: 36;
(c) an expression vector comprising a polynucleotide
comprising a nucleotide sequence encoding a heavy
chain consisting of the amino acid sequence shown in
SEQ ID NO: 34 and a polynucleotide comprising a
nucleotide sequence encoding a light chain consisting
of the amino acid sequence shown in SEQ ID NO: 36;
(d) an expression vector comprising a polynucleotide
comprising a nucleotide sequence encoding a heavy
chain consisting of the amino acid sequence shown in
SEQ ID NO: 34, and an expression vector comprising
a polynucleotide comprising a nucleotide sequence
encoding a light chain consisting of the amino acid
sequence shown in SEQ ID NO: 36;
(e) an expression vector comprising a polynucleotide
comprising a nucleotide sequence encoding a heavy
chain consisting of the amino acid sequence shown in
SEQ ID NO: 34, and a polynucleotide comprising a
nucleotide sequence encoding an Fc polypeptide con-
sisting of the amino acid sequence shown in SEQ ID
NO: 42;
(f) an expression vector comprising a polynucleotide
comprising a nucleotide sequence encoding a light
chain consisting of the amino acid sequence shown in
SEQ ID NO: 36 and a polynucleotide comprising a
nucleotide sequence encoding an Fc polypeptide con-
sisting of the amino acid sequence shown in SEQ ID
NO: 42;
(g) an expression vector comprising a polynucleotide
comprising a nucleotide sequence encoding a heavy
chain consisting of the amino acid sequence shown in
SEQ ID NO: 34, and an expression vector comprising
a polynucleotide comprising a nucleotide sequence
encoding an Fc polypeptide consisting of the amino
acid sequence shown in SEQ ID NO: 42;
(h) an expression vector comprising a polynucleotide
comprising a nucleotide sequence encoding a light
chain consisting of the amino acid sequence shown in
SEQ ID NO: 36, and an expression vector comprising
a polynucleotide comprising a nucleotide sequence
encoding an Fc polypeptide consisting of the amino
acid sequence shown in SEQ ID NO: 42;
(i) an expression vector comprising a polynucleotide
comprising a nucleotide sequence encoding a heavy
chain consisting of the amino acid sequence shown in
SEQ ID NO: 34 and a polynucleotide comprising a
nucleotide sequence encoding a light chain consisting
of the amino acid sequence shown in SEQ ID NO: 36,
as well as an expression vector comprising a polynucle-
otide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 34 and a polynucleotide comprising a nucleotide sequence comprising an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 36;

(k) an expression vector comprising a polynucleotide comprising a nucleotide sequence encoding a heavy chain consisting of the amino acid sequence shown in SEQ ID NO: 34, as well as an expression vector comprising a polynucleotide comprising a nucleotide sequence encoding a light chain consisting of the amino acid sequence shown in SEQ ID NO: 36 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 34, an expression vector comprising a polynucleotide comprising a nucleotide sequence encoding a light chain consisting of the amino acid sequence shown in SEQ ID NO: 36, and an expression vector comprising a polynucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 34, a polynucleotide comprising a nucleotide sequence encoding a light chain consisting of the amino acid sequence shown in SEQ ID NO: 36, and a polynucleotide comprising a nucleotide sequence encoding an Fc polypeptide consisting of the amino acid sequence shown in SEQ ID NO: 42.

In one embodiment, the host cell of the invention is a transformed host cell with an expression vector or vectors selected from:

(a) an expression vector comprising a polynucleotide comprising a nucleotide sequence encoding a heavy chain consisting of the amino acid sequence shown in SEQ ID NO: 38;

(b) an expression vector comprising a polynucleotide comprising a nucleotide sequence encoding a light chain consisting of the amino acid sequence shown in SEQ ID NO: 40;

(c) an expression vector comprising a polynucleotide comprising a nucleotide sequence encoding a heavy chain consisting of the amino acid sequence shown in SEQ ID NO: 38 and a polynucleotide comprising a nucleotide sequence encoding a light chain consisting of the amino acid sequence shown in SEQ ID NO: 40;

(d) an expression vector comprising a polynucleotide comprising a nucleotide sequence encoding a heavy chain consisting of the amino acid sequence shown in SEQ ID NO: 38, and an expression vector comprising a polynucleotide comprising a nucleotide sequence encoding a light chain consisting of the amino acid sequence shown in SEQ ID NO: 40;

(e) an expression vector comprising a polynucleotide comprising a nucleotide sequence encoding a heavy chain consisting of the amino acid sequence shown in SEQ ID NO: 38, and a polynucleotide comprising a nucleotide sequence encoding an Fc polypeptide consisting of the amino acid sequence shown in SEQ ID NO: 42;

(f) an expression vector comprising a polynucleotide comprising a nucleotide sequence encoding a light chain consisting of the amino acid sequence shown in SEQ ID NO: 40 and a polynucleotide comprising a nucleotide sequence encoding an Fc polypeptide consisting of the amino acid sequence shown in SEQ ID NO: 42;

(g) an expression vector comprising a polynucleotide comprising a nucleotide sequence encoding a heavy chain consisting of the amino acid sequence shown in SEQ ID NO: 38, and an expression vector comprising a polynucleotide comprising a nucleotide sequence encoding an Fc polypeptide consisting of the amino acid sequence shown in SEQ ID NO: 42;

(h) an expression vector comprising a polynucleotide comprising a nucleotide sequence encoding a light chain consisting of the amino acid sequence shown in SEQ ID NO: 40, and an expression vector comprising a polynucleotide comprising a nucleotide sequence encoding an Fc polypeptide consisting of the amino acid sequence shown in SEQ ID NO: 42;

(i) an expression vector comprising a polynucleotide comprising a nucleotide sequence encoding a heavy chain consisting of the amino acid sequence shown in SEQ ID NO: 38 and a polynucleotide comprising a nucleotide sequence encoding a light chain consisting of the amino acid sequence shown in SEQ ID NO: 40, as well as an expression vector comprising a polynucleotide comprising a nucleotide sequence encoding an Fc polypeptide consisting of the amino acid sequence shown in SEQ ID NO: 42;

(j) an expression vector comprising a polynucleotide comprising a nucleotide sequence encoding a heavy chain consisting of the amino acid sequence shown in SEQ ID NO: 38 and a polynucleotide comprising a nucleotide sequence encoding an Fc polypeptide consisting of the amino acid sequence shown in SEQ ID NO: 42, as well as an expression vector comprising a polynucleotide comprising a nucleotide sequence encoding a light chain consisting of the amino acid sequence shown in SEQ ID NO: 40;

(k) an expression vector comprising a polynucleotide comprising a nucleotide sequence encoding a heavy chain consisting of the amino acid sequence shown in SEQ ID NO: 38, as well as an expression vector comprising a polynucleotide comprising a nucleotide sequence encoding a light chain consisting of the amino acid sequence shown in SEQ ID NO: 40 and a polynucleotide comprising a nucleotide sequence encoding an Fc polypeptide consisting of the amino acid sequence shown in SEQ ID NO: 42;

(l) an expression vector comprising a polynucleotide comprising a nucleotide sequence encoding a heavy chain consisting of the amino acid sequence shown in SEQ ID NO: 38, an expression vector comprising a polynucleotide comprising a nucleotide sequence encoding a light chain consisting of the amino acid sequence shown in SEQ ID NO: 40, and an expression vector comprising a polynucleotide sequence encoding an Fc polypeptide consisting of the amino acid sequence shown in SEQ ID NO: 42;

(m) an expression vector comprising a polynucleotide comprising a nucleotide sequence encoding a heavy chain consisting of the amino acid sequence shown in SEQ ID NO: 38, a polynucleotide comprising a nucleotide sequence encoding a light chain consisting of the amino acid sequence shown in SEQ ID NO: 40, and a polynucleotide comprising a nucleotide sequence encoding an Fc polypeptide consisting of the amino acid sequence shown in SEQ ID NO: 42.

In one embodiment, the host cell of the invention is a transformed host cell with the expression vectors encoding a heavy chain and/or a light chain of a one-armed anti-human NR1 antibody, that binds to human NR1 competitively with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR cell internalization by a pathogenic anti-human NR1 antibody derived from an anti-NMDAR encephalitis patient, wherein, The host cell of the invention is a transformed host cell with an expression vector or vectors selected from:

(a) an expression vector comprising a polynucleotide comprising a nucleotide sequence encoding a heavy chain of the antibody;

(b) an expression vector comprising a polynucleotide comprising a nucleotide sequence encoding a light chain of the antibody;

(c) an expression vector comprising a polynucleotide comprising a nucleotide sequence encoding a heavy chain of the antibody and a polynucleotide comprising a nucleotide sequence encoding a light chain of the antibody;

(d) an expression vector comprising a polynucleotide comprising a nucleotide sequence encoding a heavy chain of the antibody and an expression vector comprising a polynucleotide comprising a nucleotide sequence encoding a light chain of the antibody;

(e) an expression vector comprising a polynucleotide comprising a nucleotide sequence encoding a heavy chain of the antibody, and a polynucleotide comprising a nucleotide sequence encoding an Fc polypeptide of the antibody;

(f) an expression vector comprising a polynucleotide comprising a nucleotide sequence encoding a light chain of the antibody and a polynucleotide comprising a nucleotide sequence encoding an Fc polypeptide of the antibody;

(g) an expression vector comprising a polynucleotide comprising a nucleotide sequence encoding a heavy chain of the antibody, and an expression vector comprising a polynucleotide comprising a nucleotide sequence encoding an Fc polypeptide of the antibody;

(h) an expression vector comprising a polynucleotide comprising a nucleotide sequence encoding a light chain of the antibody and an expression vector comprising a polynucleotide comprising a nucleotide sequence encoding an Fc polypeptide of the antibody;

(i) an expression vector comprising a polynucleotide comprising a nucleotide sequence encoding a heavy chain of the antibody and a polynucleotide comprising a nucleotide sequence encoding a light chain of the antibody, as well as an expression vector comprising a polynucleotide comprising a nucleotide sequence encoding an Fc polypeptide of the antibody;

(j) an expression vector comprising a polynucleotide comprising a nucleotide sequence encoding a heavy chain of the antibody and a polynucleotide comprising a nucleotide sequence encoding an Fc polypeptide of the antibody, as well as an expression vector comprising a polynucleotide comprising a nucleotide sequence encoding a light chain of the antibody;

(k) an expression vector comprising a polynucleotide comprising a nucleotide sequence encoding a heavy chain of the antibody, as well as an expression vector comprising a polynucleotide comprising a nucleotide sequence encoding a light chain of the antibody and a polynucleotide comprising a nucleotide sequence encoding an Fc polypeptide of the antibody;

(l) an expression vector comprising a polynucleotide comprising a nucleotide sequence encoding a heavy chain of the antibody, an expression vector comprising a polynucleotide comprising a nucleotide sequence encoding a light chain of the antibody, and an expression vector comprising a polynucleotide comprising a nucleotide sequence encoding an Fc polypeptide of the antibody;

(m) an expression vector comprising a polynucleotide comprising a nucleotide sequence encoding a heavy chain of the antibody, a polynucleotide comprising a nucleotide sequence encoding a light chain of the antibody, and a polynucleotide comprising a nucleotide sequence encoding an Fc polypeptide of the antibody.

A transformed host cell is not particularly limited as long as it is compatible with the expression vectors being used, and capable of being transformed with the expression vector or vectors, and expressing an antibody. A transformed host cell includes, for example, various cells, such as regularly used natural cells or artificially established cells in the technical field of the invention, (e.g. animal cell (e.g. CHOK1SV1 cell), incest cell (e.g. Sf9), cell (e.g. *Escherichia coli*, etc.), yeast (*saccharomyces*, genus *pichia*, etc.) etc.).

In one embodiment, cultured cells, such as CHOK1SV cells, CHO-DG44 cells, HEK293 cells, and NSO cells, etc., can be used as a host cell.

The method of transforming a host cell includes a calcium phosphate method, the electroporation method, etc.

<Method for Producing a One-Armed Anti-Human NR1 Antibody of the Present Invention, and the One-Armed Anti-Human NR1 Antibody Produced Thereby>

The method of producing a one-armed anti-human NR1 antibody includes the method of culturing the transformed host cell of the invention, expressing a one-armed anti-human NR1 antibody, and producing a one-armed anti-human NR1 antibody. In one embodiment, the method of producing a one-armed anti-human NR1 antibody of the invention includes culturing a host cell selected from the group consisting of (a)-(e) below, and expressing a one-armed anti-human NR1 antibody:

(a) a host cell transformed with an expression vector comprising a polynucleotide comprising a nucleotide sequence encoding a heavy chain of a one-armed anti-human NR1 antibody of the invention, a polynucleotide comprising a nucleotide sequence encoding a light chain of the antibody, and a polynucleotide comprising a nucleotide sequence encoding an Fc polypeptide of the antibody;

(b) a host cell transformed with an expression vector comprising a polynucleotide comprising a nucleotide sequence encoding a heavy chain of a one-armed anti-human NR1 antibody and a polynucleotide comprising a nucleotide sequence encoding a light chain of the antibody, as well as an expression vector comprising a polynucleotide comprising a nucleotide sequence encoding an Fc polypeptide of the antibody;

(c) a host cell transformed with an expression vector comprising a polynucleotide comprising a nucleotide sequence encoding a heavy chain of a one-armed anti-human NR1 antibody and a polynucleotide comprising a nucleotide sequence encoding an Fc polypeptide of the antibody, as well as an expression vector comprising a polynucleotide comprising a nucleotide sequence encoding a light chain of the antibody;

(d) a host cell transformed with an expression vector comprising a polynucleotide comprising a nucleotide sequence encoding a light chain of a one-armed anti-human NR1 antibody and a polynucleotide comprising a nucleotide sequence encoding an Fc polypeptide of the antibody, as well as an expression vector comprising a polynucleotide comprising a nucleotide sequence encoding a heavy chain of the antibody;

(e) a host cell transformed with an expression vector comprising a polynucleotide comprising a nucleotide sequence encoding a heavy chain of a one-armed anti-human NR1 antibody of the invention, an expression vector comprising a polynucleotide comprising a nucleotide sequence encoding a light chain of the antibody, and an expression vector comprising a polynucleotide comprising a nucleotide sequence encoding an Fc polypeptide of the antibody.

The method of producing a one-armed anti-human NR1 antibody of the invention is not particularly limited as long as the method includes culturing a transformed host cell of the present invention, and expressing a one-armed anti-human NR1 antibody.

A transformed host cell can be cultured by a known method. The culture conditions, for example, temperature, pH of the culture medium and culture time, are appropriately selected. If a host cell is an animal cell, a medium such as a MEM culture medium comprising a fetal bovine serum of approx. 5-20% (Science, 1959, Vol. 130, pp. 432-437), a DMEM culture medium (Virology, 1959, Vol. 8, p. 396), RPIH1640 culture medium (J. Am. Med. Assoc., 1967, Vol. 199, p. 519), 199 culture medium (Exp. Biol. Med., 1950, Vol. 73, pp. 1-8), etc. can be used as the culture medium. A pH of a culture medium is for example approx. 6-8, and is regularly carried out at approx. 30-40° C. for approx. 15-336 hours, ventilating and agitating cultivation as necessary. If the host cell is an insect cell, a medium such as Grace's culture medium (Proc. Natl. Acad. Sci. USA., 1985, Vol. 82, p. 8404), etc. comprising a fetal bovine serum can be used for example as the culture medium. A pH of a culture medium is for example approx. 5-8, and is regularly carried out at approx. 20-40° C. for approx. 15-100 hours, ventilating and agitating cultivation as necessary. If the host cell is an *Escherichia coli* or a yeast, a liquid medium comprising, for example, a nutrient source is suitable as the medium. The nutrition culture medium comprises for example, the source of carbon, inorganic or organic nitrogen sources necessary in the growth of the transformed host cells. Carbon sources comprise for example, glucose, dextran, soluble starch and sucrose, etc., whereas inorganic or organic nitrogen sources comprise, for example, ammonium salts, nitrates, amino acids, corn steep liquor, peptone, casein, meat extract, soybean meal and potato extract, etc. It may comprise other nutrients (e.g., inorganic salts (e.g., calcium chloride, sodium dihydrogen phosphate, magnesium chloride) and vitamins), antibiotics (e.g., tetracycline, neomycin, ampicillin, kanamycin) etc. if desired. A pH of a culture medium is for example approx. 5-8. If a host cell is

*Escherichia coli*, LB culture medium and M9 culture medium (Molecular Cloning, Cold Spring Harbor Laboratory, Vol. 3, A2.2), etc. can be used for example as the culture medium. A culture medium is regularly carried out at approx. 14-43° C. for approx. 3-24 hours, ventilating and agitating as necessary. If a host cell is yeast, the Burkholder minimal medium (Proc. Natl. Acad. Sci. USA., 1980, Vol. 77, p. 4505) etc. can be used for example as the culture medium.

A culture is regularly carried out at approx. 20-35° C. for approx. 14-144 hours, ventilating and agitating as necessary. A one-armed anti-human NR1 antibody of the invention can be expressed by the above cultivation.

In addition to culturing a transformed host cell and expressing a one-armed anti-human NR1 antibody of the invention, the method of producing a one-armed anti-human NR1 antibody of the invention can also comprise retrieving, isolating or purifying a one-armed anti-human NR1 antibody from the transformed host cell.

The method of isolation or purification comprises, for example, the method of utilizing solubility such as salting-out and solvent precipitation method; the method of utilizing molecular weight difference such as dialysis, ultrafiltration and gel filtration; the method of utilizing electric charge such as ion exchange chromatography and hydroxyapatite chromatography; the method of utilizing specific affinity such as affinity chromatography; the method of utilizing hydrophobicity difference such as reversed-phase high-performance liquid chromatography; and the method of utilizing difference of isoelectric point such as isoelectric point electrophoresis, etc.

In one embodiment, antibodies accumulated in culture supernatant can be purified by various kinds of chromatography, for example, column chromatography using protein A columns or protein G columns.

In the method of producing a one-armed anti-human NR1 antibody of the invention, a one-armed anti-human NR1 antibody can be efficiently obtained by introducing a Knobs-into-holes mutation into a CH3 of a heavy-chain of the one-armed anti-human NR1 antibody and a CH3 of an Fc polypeptide respectively which combines with the heavy-chain and forms the Fc region.

The one-armed anti-human NR1 antibody of the invention also comprises a one-armed anti-human NR1 antibody produced with the method of producing a one-armed anti-human NR1 antibody of the invention.

<Pharmaceutical Compositions Etc. Of the Invention>

Pharmaceutical compositions of the invention comprise compositions comprising a one-armed anti-human NR1 antibody of the invention and a pharmaceutically acceptable excipient. Pharmaceutical compositions of the invention can be prepared by commonly used methods with commonly used excipient in the field i.e., a pharmaceutical excipient or a pharmaceutical carrier etc. The dosage forms of these pharmaceutical compositions comprise, for example, a parenteral dosage form such as injection, drip infusion, etc., and the pharmaceutical compositions can be administered by intravenous administration, subcutaneous administration, etc. In formulating the pharmaceutical compositions, excipients, carriers, additives etc. according to these dosage forms can be used within the pharmaceutically acceptable scope.

Pharmaceutical compositions of the invention may comprise multiple kinds of one-armed anti-human NR1 antibodies of the invention. For example, the invention comprises a one-armed anti-human NR1 antibody which does not have C-terminal lysine deletion and pyroglutamylation of the N-terminus, and/or a one-armed anti-human NR1 antibody which has C-terminal lysine deletion and pyroglutamylation of the N-terminus.

In one embodiment, pharmaceutical compositions of the invention comprise a one-armed anti-human NR1 antibody selected from any of the following (1) to (5) and/or a one-armed anti-human NR1 antibody, resulting from the post-translational modification of the one-armed anti-human NR1 antibody:

(1) a one-armed anti-human NR1 antibody comprising a heavy-chain variable region comprising a CDR1 consisting of the amino acid sequence of amino acid numbers 26 to 34 of SEQ ID NO: 2, a CDR2 consisting of the amino acid sequence of amino acid numbers 52 to 58 of SEQ ID NO: 2, and a CDR3 consisting of the amino acid sequence of amino acid numbers 97 to 109 of SEQ ID NO: 2, and a light-chain variable region comprising a CDR1 consisting of the amino acid sequence of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequence of amino acid numbers 92 to 100 of SEQ ID NO: 4;

(2) a one-armed anti-human NR1 antibody comprising a heavy-chain variable region comprising a CDR1 consisting of the amino acid sequence of amino acid numbers 31 to 35 of SEQ ID NO: 6, a CDR2 consisting of the amino acid sequence of amino acid numbers 50 to 60 of SEQ ID NO: 6, and a CDR3 consisting of the amino acid sequence of amino acid numbers 99 to 110 of SEQ ID NO: 6, and a light-chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8;

(3) a one-armed anti-human NR1 antibody comprising a heavy-chain variable region comprising a CDR1 consisting of the amino acid sequence of amino acid numbers 31 to 35 of SEQ ID NO: 10, a CDR2 consisting of the amino acid sequence of amino acid numbers 50 to 66 of SEQ ID NO: 10, and a CDR3 consisting of the amino acid sequence of amino acid numbers 99 to 111 of SEQ ID NO: 10, and a light-chain variable region comprising a CDR1 consisting of the amino acid sequence of amino acid numbers 24 to 34 of SEQ ID NO: 12, a CDR2 consisting of the amino acid sequence of amino acid numbers 50 to 56 of SEQ ID NO: 12, and a CDR3 consisting of the amino acid sequence of amino acid numbers 89 to 97 of SEQ ID NO: 12;

(4) a one-armed anti-human NR1 antibody comprising a heavy-chain variable region comprising a CDR1 consisting of the amino acid sequence of amino acid numbers 31 to 36 of SEQ ID NO: 14, a CDR2 consisting of the amino acid sequence of amino acid numbers 51 to 66 of SEQ ID NO: 14, and a CDR3 consisting of the amino acid sequence of amino acid numbers 99 to 108 of SEQ ID NO: 14, and a light-chain variable region comprising a CDR1 consisting of the amino acid sequence of amino acid numbers 24 to 34 of SEQ ID NO: 16, a CDR2 consisting of the amino acid sequence of amino acid numbers 50 to 56 of SEQ ID NO: 16, and a CDR3 consisting of the amino acid sequence of amino acid numbers 89 to 97 of SEQ ID NO: 16;

(5) a one-armed anti-human NR1 antibody comprising a heavy-chain variable region comprising a CDR1 consisting of the amino acid sequence of amino acid numbers 31 to 36 of SEQ ID NO: 18, a CDR2 consisting of the amino acid sequence of amino acid numbers 51 to 66 of SEQ ID NO: 18, and a CDR3 consisting of the amino acid sequence of amino acid numbers 99 to 108 of SEQ ID NO: 18, and a light-chain variable region comprising a CDR1 consisting of the amino acid sequence of amino acid numbers 24 to 34 of SEQ ID NO: 20, a CDR2 consisting of the amino acid sequence of amino acid numbers 50 to 56 of SEQ ID NO: 20, and a CDR3 consisting of the amino acid sequence of amino acid numbers 89 to 97 of SEQ ID NO: 20.

In one embodiment, pharmaceutical compositions of the invention comprise a one-armed anti-human NR1 antibody selected from any of the following (1) to (5) and/or a one-armed anti-human NR1 antibody, resulting from the post-translational modification of the one-armed anti-human NR1 antibody:

(1) a one-armed anti-human NR1 antibody comprising a heavy-chain variable region consisting of the amino acid sequence shown in SEQ ID NO: 2, and a light-chain variable region consisting of the amino acid sequence shown in SEQ ID NO: 4; (2) a one-armed anti-human NR1 antibody comprising a heavy-chain variable region consisting of the amino acid sequence shown in SEQ ID NO: 6, and a light-chain variable region consisting of the amino acid sequence shown in SEQ ID NO: 8; (3) a one-armed anti-human NR1 antibody comprising a heavy-chain variable region consisting of the amino acid sequence shown in SEQ ID NO: 10, and a light-chain variable region consisting of the amino acid sequence shown in SEQ ID NO: 12; (4) a one-armed anti-human NR1 antibody comprising a heavy-chain variable region consisting of the amino acid sequence shown in SEQ ID NO: 14, and a light-chain variable region consisting of the amino acid sequence shown in SEQ ID NO: 16; (5) a one-armed anti-human NR1 antibody comprising a heavy-chain variable region consisting of the amino acid sequence shown in SEQ ID NO: 18, and a light-chain variable region consisting of the amino acid sequence shown in SEQ ID NO: 20.

In one embodiment, pharmaceutical compositions of the invention comprise a one-armed anti-human NR1 antibody selected from any of the following (1) to (5) and/or a one-armed anti-human NR1 antibody, resulting from the post-translational modification of the one-armed anti-human NR1 antibody:

(1) a one-armed anti-human NR1 antibody comprising a heavy-chain comprising a heavy-chain variable region comprising a CDR1 consisting of the amino acid sequences of amino acid numbers 26 to 34 of SEQ ID NO: 2, a CDR2 consisting of the amino acid sequences of amino acid numbers 52 to 58 of SEQ ID NO: 2, and a CDR3 consisting of the amino acid sequences of amino acid numbers 97 to 109 of SEQ ID NO: 2, a light-chain comprising a light-chain variable region comprising a CDR1 consisting of the amino acid sequences of amino acid numbers 26 to 33 of SEQ ID NO: 4, a CDR2 consisting of the amino acid sequence of amino acid numbers 51 to 53 of SEQ ID NO: 4, and a CDR3 consisting of the amino acid sequences of amino acid numbers 92 to 100 of SEQ ID NO: 4, as well as an Fc polypeptide;

(2) a one-armed anti-human NR1 antibody comprising a heavy-chain comprising heavy-chain variable region comprising a CDR1 consisting of the amino acid sequence of amino acid numbers 31 to 35 of SEQ ID NO: 6, a CDR2 consisting of the amino acid sequence of amino acid numbers 50 to 66 of SEQ ID NO: 6, and a CDR3 consisting of the amino acid sequence of amino acid numbers 99 to 110 of SEQ ID NO: 6, a light-chain comprising a light-chain variable region comprising a CDR1 consisting of the amino acid sequence of amino acid numbers 24 to 34 of SEQ ID NO: 8, a CDR2 consisting of the amino acid sequence of amino acid numbers 50 to 56 of SEQ ID NO: 8, and a CDR3 consisting of the amino acid sequence of amino acid numbers 89 to 98 of SEQ ID NO: 8, as well as an Fc polypeptide;

(3) a one-armed anti-human NR1 antibody comprising a heavy-chain variable region comprising a CDR1 consisting of the amino acid sequences of amino acid numbers 31 to 35 of SEQ ID NO: 10, a CDR2 consisting of the amino acid sequences of amino acid numbers 50 to 66 of SEQ ID NO: 10, and a CDR3 consisting of the amino acid sequences of amino acid numbers 99 to 111 of SEQ ID NO: 10, a light-chain comprising a light-chain variable region comprising a CDR1 consisting of the amino acid sequences of amino acid numbers 24 to 34 of SEQ ID NO: 12, a CDR2 consisting of the amino acid sequences of amino acid numbers 50 to 56 of SEQ ID NO: 12, and a CDR3 consisting of the amino acid sequences of amino acid numbers 89 to 97 of SEQ ID NO: 12, as well as an Fc polypeptide;

(4) a one-armed anti-human NR1 antibody comprising a heavy-chain comprising a heavy-chain variable region comprising a CDR1 consisting of the amino acid sequences of amino acid numbers 31 to 36 of SEQ ID NO: 14, a CDR2 consisting of the amino acid sequences of amino acid numbers 51 to 66 of SEQ ID NO: 14, and a CDR3 consisting of the amino acid sequences of amino acid numbers 99 to 108 of SEQ ID NO: 14, and a light-chain comprising a light-chain variable region comprising a CDR1 consisting of the amino acid sequences of amino acid numbers 24 to 34 of SEQ ID NO: 16, a CDR2 consisting of the amino acid sequences of amino acid numbers 50 to 56 of SEQ ID NO: 16, and a CDR3 consisting of the amino acid sequences of amino acid numbers 89 to 97 of SEQ ID NO: 16, as well as an Fc polypeptide;

(5) a one-armed anti-human NR1 antibody comprising a heavy-chain comprising a heavy-chain variable region comprising a CDR1 consisting of the amino acid sequences of amino acid numbers 31 to 36 of SEQ ID NO: 18, a CDR2 consisting of the amino acid sequences of amino acid numbers 51 to 66 of SEQ ID NO: 18, and a CDR3 consisting of the amino acid sequences of amino acid numbers 99 to 108 of SEQ ID NO: 18, a light-chain comprising a light-chain variable region comprising a CDR1 consisting of the amino acid sequences of amino acid numbers 24 to 34 of SEQ ID NO: 20, a CDR2 consisting of the amino acid sequences of amino acid numbers 50 to 56 of SEQ ID NO: 20, and a CDR3 consisting of the amino acid sequences of amino acid numbers 89 to 97 of SEQ ID NO: 20; as well as an Fc polypeptide.

In one embodiment, pharmaceutical compositions of the invention comprise a one-armed anti-human NR1 antibody selected from any of the following (1) to (5) and/or a one-armed anti-human NR1 antibody resulting from the post-translational modification of the one-armed anti-human NR1 antibody:

(1) a one-armed anti-human NR1 antibody comprising a heavy-chain comprising a heavy-chain variable region consisting of the amino acid sequence shown in SEQ ID NO: 2, a light-chain comprising a light-chain variable region consisting of the amino acid sequence shown in SEQ ID NO: 4, and an Fc polypeptide;

(2) a one-armed anti-human NR1 antibody comprising a heavy-chain comprising a heavy-chain variable region consisting of the amino acid sequence shown in SEQ ID NO: 6, a light-chain comprising a light-chain variable region consisting of the amino acid sequence shown in SEQ ID NO: 8, and an Fc polypeptide;

(3) a one-armed anti-human NR1 antibody comprising a heavy-chain comprising a heavy-chain variable region consisting of the amino acid sequence shown in SEQ ID NO: 10, a light-chain comprising a light-chain variable region consisting of the amino acid sequence shown in SEQ ID NO: 12, and an Fc polypeptide;

(4) a one-armed anti-human NR1 antibody comprising a heavy-chain comprising a heavy-chain variable region consisting of the amino acid sequence shown in SEQ ID NO: 14, a light-chain comprising a light-chain variable region consisting of the amino acid sequence shown in SEQ ID NO: 16, and an Fc polypeptide;

(5) a one-armed anti-human NR1 antibody comprising a heavy-chain comprising a heavy-chain variable region consisting of the amino acid sequence shown in SEQ ID NO: 18, a light-chain comprising a light-chain variable region consisting of the amino acid sequence shown in SEQ ID NO: 20, and an Fc polypeptide.

In one embodiment, pharmaceutical compositions of the invention comprise a one-armed anti-human NR1 antibody comprising a heavy-chain consisting of the amino acid sequence shown in SEQ ID NO: 22, a light-chain consisting of the amino acid sequence shown in SEQ ID NO: 24, and an Fc polypeptide consisting of the amino acid sequence shown in SEQ ID NO: 42, and/or a one-armed anti-human NR1 antibody resulting from the post-translational modification of the one-armed anti-human NR1 antibody.

In one embodiment, pharmaceutical compositions of the invention comprise a one-armed anti-human NR1 antibody comprising a heavy-chain consisting of the amino acid sequence shown in SEQ ID NO: 26, a light-chain consisting of the amino acid sequence shown in SEQ ID NO: 28, and an Fc polypeptide consisting of the amino acid sequence shown in SEQ ID NO: 42, and/or a one-armed anti-human NR1 antibody resulting from the post-translational modification of the one-armed anti-human NR1 antibody.

In one embodiment, pharmaceutical compositions of the invention comprise a one-armed anti-human NR1 antibody comprising a heavy-chain consisting of the amino acid sequence shown in SEQ ID NO: 30, a light-chain consisting of the amino acid sequence shown in SEQ ID NO: 32, and an Fc polypeptide consisting of the amino acid sequence shown in SEQ ID NO: 42, and/or a one-armed anti-human NR1 antibody resulting from the post-translational modification of the one-armed anti-human NR1 antibody comprising.

In one embodiment, pharmaceutical compositions of the invention comprise a one-armed anti-human NR1 antibody comprising a heavy-chain consisting of the amino acid sequence shown in SEQ ID NO: 34, a light-chain consisting of the amino acid sequence shown in SEQ ID NO: 36, and an Fc polypeptide consisting of the amino acid sequence shown in SEQ ID NO: 42, and/or a one-armed anti-human NR1 antibody resulting from the post-translational modification of the one-armed anti-human NR1 antibody comprising.

In one embodiment, pharmaceutical compositions of the invention comprise a one-armed anti-human NR1 antibody comprising a heavy-chain consisting of the amino acid sequence shown in SEQ ID NO: 38, a light-chain consisting of the amino acid sequence shown in SEQ ID NO: 40, and an Fc polypeptide consisting of the amino acid sequence shown in SEQ ID NO: 42, and/or a one-armed anti-human NR1 antibody resulting from the post-translational modification of the one-armed anti-human NR1 antibody comprising.

In one embodiment, pharmaceutical compositions of the invention comprise a one-armed anti-human NR1 antibody, that binds to human NR1 competitively with an anti-human NR1 antibody comprising a heavy-chain variable region consisting of the amino acid sequence shown in SEQ ID NO: 2 and a light-chain variable region consisting of the amino acid sequence shown in SEQ ID NO: 4, and inhibits NMDAR cell internalization by a pathogenic anti-human NR1 antibody derived from an anti-NMDAR encephalitis patient, and/or a one-armed anti-human NR1 antibody resulting from the post-translational modification of the one-armed anti-human NR1 antibody.

The dosage of a one-armed anti-human NR1 antibody of the invention differs according to the condition of disease, the age of patient, or the dosage form to be used. For example, the dosage of about 0.001 mg/kg to 100 mg/kg can be used.

Furthermore, the dosage of a one-armed anti-human NR1 antibody of the invention corresponding to such dose can be adjusted and formulated.

Pharmaceutical compositions of the invention can be used as a therapeutic agent for anti-NMDAR encephalitis.

The invention comprises pharmaceutical compositions of a one-armed anti-human NR1 antibody comprising a one-armed anti-human NR1 antibody of the invention and a pharmaceutically acceptable excipient, for treatment. Moreover, the invention comprises a method of treating anti-NMDAR encephalitis which comprises administering a therapeutically effective amount of a one-armed anti-human NR1 antibody of the invention. Moreover, the invention comprises a one-armed anti-human NR1 antibody of the invention used as the treatment of anti-NMDAR encephalitis.

Moreover, the invention comprises the use of a one-armed anti-human NR1 antibody of the invention in the manufacturing of pharmaceutical compositions for treating anti-NMDAR encephalitis.

<Monovalent Anti-Human NRA Antibody Derivative of the Invention>

In the specification of the invention, a "monovalent anti-human NR1 antibody derivative" is a monovalent antibody derivative binding to human NRA, which comprises an antigen binding site for human NR1 derived from an anti-human NR1 antibody.

A monovalent anti-human NR1 antibody derivative of the invention comprises, for example, scFc derived from an anti-human NR1 antibody, Fab fragment, F(ab')₂ fragment, etc.

A monovalent anti-human NR1 antibody derivative of the invention is a monovalent anti-human NR1 antibody derivative comprising a heavy chain variable region and a light chain variable region selected from any of the following (1) to (4):

(1) A monovalent anti-human NR1 antibody derivative comprising a heavy-chain variable region comprising a CDR1 consisting of the amino acid sequences of amino acid numbers 31 to 35 of SEQ ID NO: 6, a CDR2 consisting of the amino acid sequences of amino acid numbers 50 to 66 of SEQ ID NO: 6, and a CDR3 consisting of the amino acid sequence of amino acid numbers 99 to 110 of SEQ ID NO: 6, and a light-chain variable region comprising a CDR1 consisting of the amino acid sequences of amino acid numbers 24 to 34 of SEQ ID NO: 8, a CDR2 consisting of the amino acid sequences of amino acid numbers 50 to 56 of SEQ ID NO: 8, and a CDR3 consisting of the amino acid sequences of amino acid numbers 89 to 98 of SEQ ID NO: 8;

(2) A monovalent anti-human NR1 antibody derivative comprising a heavy-chain variable region comprising a CDR1 consisting of the amino acid sequences of amino acid numbers 31 to 35 of SEQ ID NO: 10, a CDR2 consisting of the amino acid sequences of amino acid numbers 50 to 66 of SEQ ID NO: 10, and a CDR3 consisting of the amino acid sequences of amino acid numbers 99 to 111 of SEQ ID NO: 10, and a light-chain variable region comprising a CDR1 consisting of the amino acid sequences of amino acid numbers 24 to 34 of SEQ ID NO: 12, a CDR2 consisting of the amino acid sequences of amino acid numbers 50 to 56 of SEQ ID NO: 12, and a CDR3 consisting of the amino acid sequences of amino acid numbers 89 to 97 of SEQ ID NO: 12;

(3) A monovalent anti-human NR1 antibody derivative comprising a heavy-chain variable region comprising a CDR1 consisting of the amino acid sequences of amino acid number 31 to 36 of SEQ ID NO: 14, a CDR2 consisting of the amino acid sequences of amino acid numbers 51 to 66 of SEQ ID NO: 14, and a CDR3 consisting of the amino acid sequence of amino acid numbers 99 to 108 of SEQ ID NO: 14, and a light-chain variable region comprising a CDR1 consisting of the amino acid sequences of amino acid numbers 24 to 34 of SEQ ID NO: 16, a CDR2 consisting of the amino acid sequences of amino acid numbers 50 to 56 of SEQ ID NO: 16, and a CDR3 consisting of the amino acid sequences of amino acid numbers 89 to 97 of SEQ ID NO: 16;

(4) A monovalent anti-human NR1 antibody derivative comprising a heavy-chain variable region comprising a CDR1 consisting of the amino acid sequences of amino acid numbers 31 to 36 of SEQ ID NO: 18, a CDR2 consisting of the amino acid sequences of amino acid numbers 51 to 66 of SEQ ID NO: 18, and a CDR3 consisting of the amino acid sequences of amino acid numbers 99 to 108 of SEQ ID NO: 18, and a light-chain variable region comprising a CDR1 consisting of the amino acid sequences of amino acid numbers 24 to 34 of SEQ ID NO: 20, a CDR2 consisting of the amino acid sequences of amino acid numbers 50 to 56 of SEQ ID NO: 20, and a CDR3 consisting of the amino acid sequences of amino acid numbers 89 to 97 of SEQ ID NO: 20.

In one embodiment, a monovalent anti-human NR1 antibody derivative of the invention is a monovalent anti-human NR1 antibody derivative comprising a heavy chain variable region and a light chain variable region selected from any of the following (5) to (8):

(5) A monovalent anti-human NR1 antibody derivative comprising a heavy chain variable region consisting of the amino acid sequence shown in SEQ ID NO: 6, and a light chain variable region consisting of the amino acid sequence shown in SEQ ID NO: 8;

(6) A monovalent anti-human NR1 antibody derivative comprising a heavy chain variable region consisting of the amino acid sequence shown in SEQ ID NO: 10, and a light chain variable region consisting of the amino acid sequence shown in SEQ ID NO: 12;

(7) A monovalent anti-human NR1 antibody derivative comprising a heavy-chain variable region consisting of the amino acid sequence shown in SEQ ID NO: 14, and a light chain variable region consisting of the amino acid sequence shown in SEQ ID NO: 16;

(8) A monovalent anti-human NR1 antibody derivative comprising a heavy chain variable region consisting of the amino acid sequence shown in SEQ ID NO: 18, and a light chain variable region consisting of the amino acid sequence shown in SEQ ID NO: 20.

A monovalent anti-human NR1 antibody derivative of the invention comprises a monovalent anti-human NR1 antibody derivative that competitively binds to human NR1 with an anti-human NR1 antibody comprising a heavy chain variable region consisting of the amino acid sequence shown in SEQ ID NO: 2 and a light chain variable region consisting of the amino acid sequence shown in SEQ ID NO: 4, and inhibits NMDAR internalization by a pathogenic anti-human NR1 antibody derived from an anti-NMDA receptor encephalitis patient. The monovalent anti-human NR1 antibody derivative of the invention is obtainable for a person skilled in the art as described in the section <One-armed anti-human NR1 antibody of the invention>.

The modification of a monovalent anti-human NR1 antibody derivative of the invention may be performed to improve its stability in vivo.

The modification comprises, for example, PEGylation.

The invention further comprises a polynucleotide encoding the antibody derivative, an expression vector comprising the polynucleotide, a host cell transformed by the expression vector, the method of producing the antibody derivative, pharmaceutical compositions comprising the antibody derivative, the use of the antibody derivative in manufacturing of the pharmaceutical composition, and the method for treating anti-NMDAR encephalitis patients with the antibody derivative.

Specific examples are provided here to provide a further understanding of the invention; however, these examples are provided for an illustrative purpose and not for limiting the invention.

EXAMPLES

Unless otherwise specified, the steps described in the examples below are enabled according to the well-known methods. Moreover, regarding the part of the examples using a commercially available kit or reagent etc., unless otherwise specified, the experiments are conducted according to the attached protocols.

Examples 1: Obtaining an Antibody Derived from Anti-NMDAR Encephalitis Patient Based on the sequence information described in patent document 2 (see Claim 1 of the document, and the description of the examples), an anti-human NR1 monoclonal antibody (003-109, 007-168, 007-169, 007-124, 007-142, 008-218, P003-102, hereinafter referred to as a "pathogenic anti-human NR1 antibody") having the same heavy chain variable region and light chain variable region of the antibody isolated from an anti-NMDAR encephalitis patient described in the patent document, was prepared according to the ordinary method. In particular, a polynucleotide encoding a heavy chain polypeptide was inserted into pcDNA3.4 (Thermo Fisher Scientific) to prepare the expression vector, wherein the heavy-chain polypeptide contains a signal sequence added to the N-terminus portion, and a CH1 sequence, a hinge sequence and a Fc sequence added to the C-terminus portion of the heavy chain variable region sequence of a pathogenic anti-human NR1 antibody. Similarly, a polynucleotide encoding a polypeptide is inserted into pcDNA3.4 to prepare the expression vector, wherein a light chain variable region sequence of the polynucleotide encoding the polypeptide contains a signal sequence added to the N-terminus portion, and a CH1 sequence added to the C-terminus portion of a pathogenic anti-human NR1 antibody. The expression vector was transfected in ExpiCHO-S cells (Thermo Fisher Scientific, A29127), and an antibody was obtained according to the ordinary method.

The binding activities of seven pathogenic anti-human NR1 antibodies described above were evaluated by the flow cytometry measurement.

This flow cytometry testing (Becton, Dickinson and Company, FACS Verse) is performed (same as in Example 7) in NMDAR expressing HEK cells (described below). As a result, all of the seven pathogenic anti-human NR1 antibodies showed high binding activities in NMDAR expressing HEK cells.

P003-102 (having a heavy-chain variable region consisting of the amino acid sequence shown in SEQ ID NO: 2, and a light-chain variable region consisting of the amino acid sequence shown in SEQ ID NO: 4) showed the highest binding activity in NMDAR expressing HEK cells (data not shown).

Note that NMDAR expressing HEK cells used in the Example is a human NMDAR (NR1/NR2B) expressing HEK cell line (Charles River Laboratories, CTN6121), and, unless otherwise specified, was cultured at 37° C. and in the presence of 50% CO2, using 10% FBS (GE Healthcare Life Sciences, SH30070.03), 50 units/mL Penicillin-Streptomycin (Penicillin-Streptomycin, Thermo Fisher Scientific, 15070063), 0.5 mg/mL Geneticin (Geneticin, Thermo Fisher Scientific, 10131027), 0.005 mg/mL Blasticidin (Blasticidin, InvivoGen, ant-bl-05) and 0.1 mg/mL Zeocin (Zeocin, Thermo Fisher Scientific, R25001)-contenting DMEIF12 (Thermo Fisher Scientific, 11320033) (hereinafter, referred to as a "NMDAR expressing HEK cell culture medium).

Example 2: Confirming the NMDAR Binding Activity of a One-Armed Pathogenic Anti-Human NR1 Antibody P003-102

A monovalent anti-human NR1 antibody derivative derived from P003-102 showing high stability and the highest binding activity to an NMDAR expressing HEK cells was prepared.

A monovalent anti-human NR1 antibody derived from P003-102 was prepared based on the description of prior patent document (WO1998/050431). In particular, an antibody heavy-chain expression vector was prepared wherein a polynucleotide (SEQ ID NO: 21) encoding a heavy chain polypeptide (SEQ ID NO: 22) having a Knobs-into-holes mutation (hereinafter referred to as a "KIH mutation") in the constant region of a heavy chain of P003-102 is inserted into pcDNA3.4. An FC expression vector was prepared, wherein an FC polypeptide (SEQ ID NO: 42) encoding a polynucleotide (SEQ ID NO: 41) wherein an KIH mutation and the above mentioned KIH mutation are inserted into pcDNA3.4. An antibody light chain expression vector was prepared, wherein a polynucleotide (SEQ ID NO: 23) encoding a light chain polypeptide (SEQ ID NO: 24) of P003-102 is inserted into pcDNA3.4. A monovalent antibody (one-armed antibody) having an antigen-binding site derived from P003-102 (hereinafter, referred to as "ABN-5") was obtained by transfecting three vectors of an antibody heavy chain expression vector, an antibody light chain expression vector, and an FC expression vector into ExpiCHO-S cells, and purifying the antibody molecule expressed in the cell, according to the ordinary method.

Figure 1:
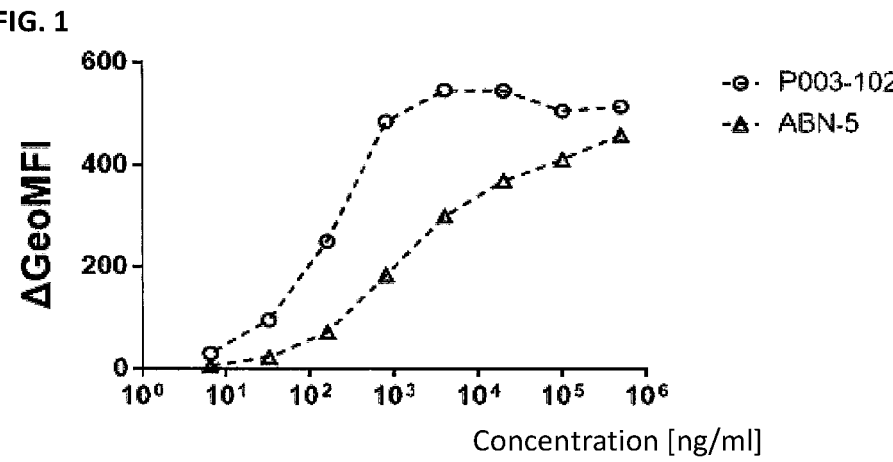
FIG. 1 illustrates binding activity of a pathogenic anti-human NR1 antibody P003-102 and a one-armed anti-human NR1 antibody (ABN-5) derived from P003-102 to an NMDAR-expressing HEK cell. The vertical axis indicates binding activity (ΔGeoMFI: difference between the geometric mean fluorescence intensity when the test antibody is added and the geometric mean fluorescence intensity when the test antibody is not added (fluorescence-labeled secondary antibody only)) and the horizontal axis indicates the antibody concentration.

As described in Example 1, the binding activity of ABN-5 to human NMDAR was evaluated by the flow cytometry testing in NMDAR expressing HEK cells. ABN-5, a one-armed antibody, showed binding activity to NMDAR expressed in HEK cells although it is weaker than that of P003-102, a bivalent antibody (FIG. 1). Moreover, ABN-5 showed a higher binding activity to human NMDAR than the other six pathogenic anti-human NR1 antibodies (data not shown).

(Example 3: Internalizing NMDAR into a cell by a pathogenic anti-human NR1 antibody) A pathogenic anti-human NR1 antibody induces the internalization of NMDAR by crosslinking the NMDAR on the cell surface. As a result, it is reported that the expression level of NMDAR on the surface of a cell is reduced (non patent document 1).
A pathogenic anti-human NR1 antibody prepared in Example 1 also reduces the expression level of NMDAR on the cell surface of HEK cells.

NMDAR expressing HEK cells was cultured overnight by exchanging NMDAR expression cell culture medium with 10% Dialyzed FBS (Thermo Fisher Scientific, 26400-044), 50 units/mL Penicillin-Streptomycin, 2.0 µg/mL Tetracycline (Tetracycline, Sigma-Aldrich, T7660) and 0.2 mM Memantine (Memantine, Sigma-Aldrich, M9292)-containing Neurobasal (Neurobasal) culture medium (Thermo Fisher Scientific, 21103049) (hereinafter, referred to as an "inducing medium"). A pathogenic anti-human NR1 antibody 007-142 was added at a concentration of 100 µg/mL. 24 hours after the addition of the antibody, the expression level of NMDAR on the cell surface was evaluated by the flow cytometry measurement with FACS Verse. From the dot plot of the 2D expansion of the forward-scattered light (FSC) and side-scattered light (CCS) signals, single cells, followed by HEK cells or a group of cells corresponding to NMDAR-expressing HEK cells, were extracted by gating. The geometric mean fluorescence intensity (GeoMFI) per 5000 cells of the extracted group of cells was measured and used for the evaluation. As a control antibody of the same isotype, an in-house anti-KLH antibody (3G6) was used. 007-142 reduced the expression of NMDAR on the cell surface to less than 50%, when added to the medium (data not shown).

Example 4: Maintaining the Function of NMDAR Expressed in HEK Cells by Adding ABN-5 in Advance Whether ABN-5, a one-armed antibody, can rescue the reduction of the expression level of NMDAR on the cell surface by a pathogenic anti-human NR1 antibody and the hypofunction of NMDAR was determined by two evaluation methods below.

First, the inhibitory effect of ABN-5 on the expression level of NMDAR was evaluated. Different concentration of ABN-5 via serial dilution was added to the culture media of NMDAR expressing HEK cells overnight.

Two hours after the addition, 007-142, a pathogenic human NR1 antibody, is added to the medium at the concentration of 100 µg/mL, and the expression level of NMDAR on the cell surface 24 hours after the addition of 007-142 was evaluated by the flow cytometry measurement as well as Example 3. 007-142 reduced the expression level of NMDAR on the cell surface of HEK cells to less than 50%. However, the expression level of NMDAR by 007-142 on the surface of a cell was restored in a concentration-dependent manner by ABN-5 (data not shown).

To evaluate if ABN-5 can prevent the hypofunction of NMDAR by a P003-102 antibody, calcium influx was used as an index in NMDAR expressing HEK cells. In particular, different concentration of ABN-5 via serial dilution was added to the culture media of NMDAR expressing HEK cells which was cultured overnight before the treatment. After adding ABN-5 for 15 minutes, P003-102 was added to the culture medium at a concentration of 0.1 µg/mL. ABN-5 was cultured for 6 hours.

After removing the media, 100 µL/well of the prepared solution of FLIPR Calcium 6 Assay Kit (Molecular Device, R8190) was added to the ABN-5, and cultured for two hours. NMDA (TOCRIS, 0114) with a final concentration of 30 µM was used to stimulate NMDAR. The intracellular calcium concentration was measured by Fluorometric Imaging Plate Reader (Molecular Devices, FLIPR TETRA) with FLIPR Calcium 6 Assay Kit (Molecular Devices, R6133). As a result, the addition of a P003-102 antibody to the media causes the hypofunction of NMDAR on NMDAR expressing HEK celld, and that the hypofunction is inhibited in a concentration-dependent manner by ABN-5 (data not shown).

From the above, both one-armed anti-human NR1 antibody and pathogenic anti-human NR1 antibody bind to cell surface NMDAR, as well as a. However, the one-armed anti-human NR1 antibody does not induce the internalization of NMDAR, unlike the pathogenic anti-human NR1 antibody. Moreover, the one-armed anti-human NR1 antibody antagonistically acts on the pathogenic anti-human NR1 antibody, and prevents the hypofunction of NMDAR by the pathogenic anti-human NR1 antibody, by maintaining the expression level of NMDAR on the cell surface.

Example 5: Isolating a Murine Antibody which Binds to Human NR1 Antagonistically Against the Pathogenic Anti-Human NR1 Antibody P003-102

At first, an anti-human NR1 antibody which binds potently to P003-102 and strongly to human NR1, was isolated to generate a one-armed anti-human NR1 antibody having stronger binding activity to human NMDAR than ABN-5.

In particular, a murine antibody which has a high binding activity to human NR1 was isolated by using a BALB/cAJc1 mouse and a Jcl:BDF mouse (both purchased from CLEA Japan). According to the ordinary method, human NR1 protein was injected into a mouse together with an adjuvant which elicits an immune reaction.
Human NR1 protein used for the immunization was prepared by the following methods.

A linker, a HisTag sequence (His*8), an AviTag sequence (Avidity) and a nucleotide sequence encoding a stop codon were added to the 3' terminus of a polynucleotide encoding the extracellular domain of human NR1 (SEQ ID NO: 43, corresponding amino acid sequences is shown in SEQ ID NO: 44), by gene engineering techniques, and inserted into pcDNA3.1 (Thermo Fisher Scientific), and became an expression vector of fusion protein of human NR1 and HisTag (hereinafter referred to as "human NR1-His protein"). The expression vector was transfected in Expi293F cells (Thermo Fisher Scientific, A14528). Human NR1-His protein was purified from the culture supernatant.

After injecting mice with the purified human NR1-His protein and an adjuvant for several times according to the ordinary method, lymphocytes were collected from mouse spleen or lymph node.

Human NR1-His protein was fluorescently labeled using the Alexa Fluor 647 Antibody Labeling Kit (Thermo Fisher Scientific, A20186). Based on the description of the prior non-patent document (BMC Biol., 2012, Vol. 10, Art. No. 80), B cells bound to the fluorescently labeled human NR1-His protein from the mouse lymphocytes were sorted with the cell sorter (Becton Dickinson, FACSmelody). Following the method, nucleic acid encoding the antibody extracted from the sorted B cells was cloned, and used to produce mouse antibody that binds to the human NR1. The human NR1-His protein was used and ELISA binding assay was carried out for evaluating the binding activity of NR1 of the produced mouse antibody following the ordinary method (the specific conditions are the same as that of the ELISA competitive assay described below). As a result, a larger number of mouse antibodies with a higher binding activity to human NR1 than a P003-102 antibody could be isolated (data not shown).

An ELISA competitive assay was performed to determine which antibody has antagonistic activity against P003-102 from the isolated mouse. Specifically, 15 µL of the human NR1-His protein solution (1 µg/mL in Tris Buffered Saline (herein referred to as "TBS")) was added to the 384 well plate (Thermo Fisher Scientific, 460372) and incubated overnight at 4° C. Then, the human NRA-His protein solution was removed and washed with 0.5% Tween-20 comprising TBS, NIPPON GENE, 310-07375 (referred to as "TBS-T"). After the wash, 50 uL of Blocking One (Nacalai Tesque, Inc., 03953-95) was added and incubated at room temperature for 1 hour or more.

The blocking solution was removed and washed as described above. 15 uL of mouse anti-human NR1 antibodies with a concentration from 100,000 ng/mL to 0.1 ng/mL (TBS-T containing 5% BlockingOne) or comparative antibodies (P003-102) were added to each well and incubated at room temperature for 10 to 20 minutes.

P003-102 was biotin labeled using Biotin Labeling kit-NH2 (DOJINDO and LK03). 15 uL of Biotin labeled P003-102 (600 ng/mL in dilute solution) was added and incubated at room temperature for one hour. After the wash, 15 µL is added to the HRP-labelled streptavidin (Funakoshi Co., Ltd., 21130) diluted 8,000 times using diluent, and incubated at room temperature for 30 minutes. After the wash, 15 µL is added to the BM Chemiluminescence ELISA Substrate (POD) (Roche Diagnotics 11 582 950 001, which is a chemiluminescence detection reagent used to determine the chemiluminescence in the multi-labeled plate reader (PerkinElmer, 2103 EnVision). The inhibition rate ranged from the measured value of 100,000 ng/mL of a comparative antibody is 100% to the measured value of 0 ng/mL is 0%.

The inhibition rate was analyzed by four-parameter logistic curve fitting. The inhibition rate of each sample was calculated by the following calculation formulas.

Inhibition rate (%)=(1−(sample measured value−100% measured value)/(0% measured value−100% measured value))×100 and samples with a negative value for the inhibition rate are regarded as 0%.

Figure 2:
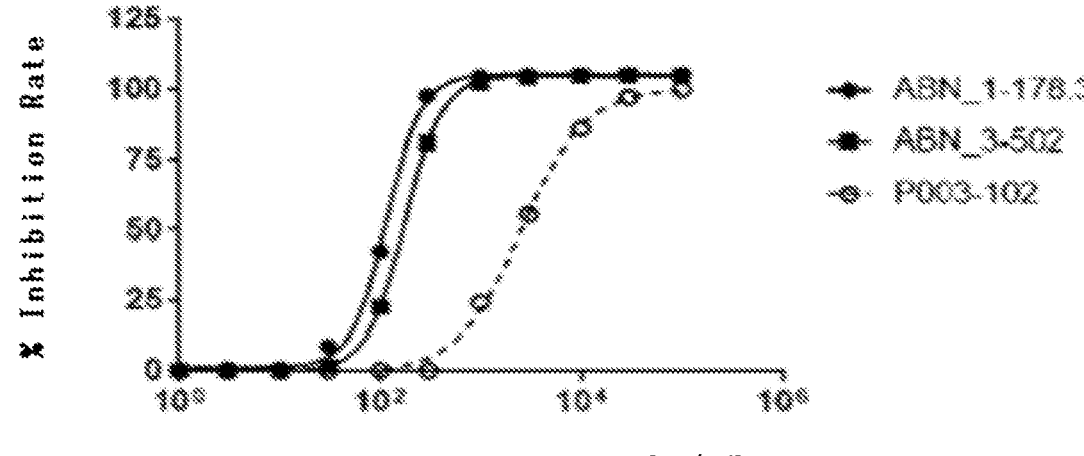
FIG. 2 illustrates inhibitory activity of a novel mouse anti-human NR1 antibody isolated in Example 5 to the binding of a pathogenic anti-human NRA antibody P003-102 to a human NRA. The vertical axis indicates the inhibitory activity (inhibition rate) of the mouse anti-human NR1 antibody to the binding of a biotin-labeled P003-102 to the human NR1 protein. The horizontal axis indicates the antibody concentration.

The anti-mouse anti-human NR1 monoclonal antibodies having antagonistic activity against biotin labeled P003-102 were analyzed. Among the anti-mouse anti-human NR1 antibodies, ABN_1-175, ABN_1-178.3, ABN_3-385 and ABN_3-502 showed stronger antagonistic activity against P003-102. In particular, ABN_1-178.3 and ABN_3-502 had the strongest antagonistic activity against P003-102 (FIG. 2).

Example 6: Method for Producing a One-Armed Anti-Human NR1 Antibody of the Invention Since four mice anti-NR1 monoclonal antibodies (ABN 1-175, ABN_1-178.3, and ABN_3-385, ABN_3-502) showed strong antagonistic activity against P003-102, humanized one-armed anti-human NR1 antibodies were produced.

The amino acid sequence of the heavy chain variable region (VH) and a light chain variable region (VL) of ABN_1-175, ABN_1-178.3, ABN 3-385, or ABN_3-502 was designed using the technique described in the prior non patent document (Front Biosci., 2008, Vol. 13, pp. 1619-1633). Based on a well-known technique, a human antibody framework sequence having a highly homologous amino acid sequence against the amino acid sequence of the framework region (FR) of the VH and VL of the mouse antibody based on the template human antibody as the transplant place of the complementarity-determining region (CDR) amino acid in VH and VL, is plurality selected from the framework data base of a human germ line. Using this sequence information, the amino acid sequence of the plurality of humanized antibodies from one mouse antibody was designed. The CDR sequence was determined and referenced from the Kabat data base ("Sequences of Proteins of Immunological Interest", US Department of Health and Human Services, US Government Printing Office) from amino acid sequence obtained in example 5. Furthermore, ABN-5 (example 2) is a plurality of humanized one-armed anti-human NR1 monoclonal antibodies from each mouse respectively produced by combining with the constant region sequence having KIH mutant. These humanized one-armed anti-human NR1 monoclonal antibodies are one-armed antibodies consisting of one heavy chain polypeptide and one light chain polypeptide that humanized any one of ABN_1-175, ABN_1-178.3, ABN_3-385 and ABN_3-502, as well as one Fc polypeptide.

Example 7: Measuring the NMDAR Binding Activity of the Humanized One-Armed Anti-Human NR1 Antibodies The binding activity of the produced humanized one-armed anti-human NR1 monoclonal antibodies was evaluated in a flow cytometry trial using the NMDAR expressing HEK cell.

The NMDAR expressing HEK cells were induced overnight and collected. After recovery, per $1.5 \times 10^5$ cell count, a humanized one-arm anti-human NR1 antibody and ABN-5 derived from a mouse antibody was added starting at a concentration of 30 ug/mL and serially diluted 3-fold to produce 11 different concentrations and incubated with the cells at 4° C. for 30 mins. After staining, the cells were sedimented at 1,200 rpm for 5 minutes and the supernatant was removed. After adding 2% Dialyzed FBS to the cells, the cells were centrifuged and sedimented. After the supernatant was removed, the PE labeled anti-human IgG antibody (Jackson ImmunoResearch Laboratories, 109-116-098) was diluted 100 times with 2% Dialyzed FBS and added to cells for 30 minutes at 4° C. After staining, the cells were centrifuged and sedimented as described above. After removing the supernatant, the cells were suspended in 2% Dialyzed FBS and the steps after secondary staining were repeated. The flow cytometry (FACS Verse) was measured as described in Example 3. each antibody binds with the cell surface NMDAR from GeoMFI showing the PE Fluorescence intensity value was analyzed using FlowJo (Becton Dickinson, Ver. 10.0.8).

Figure 3:
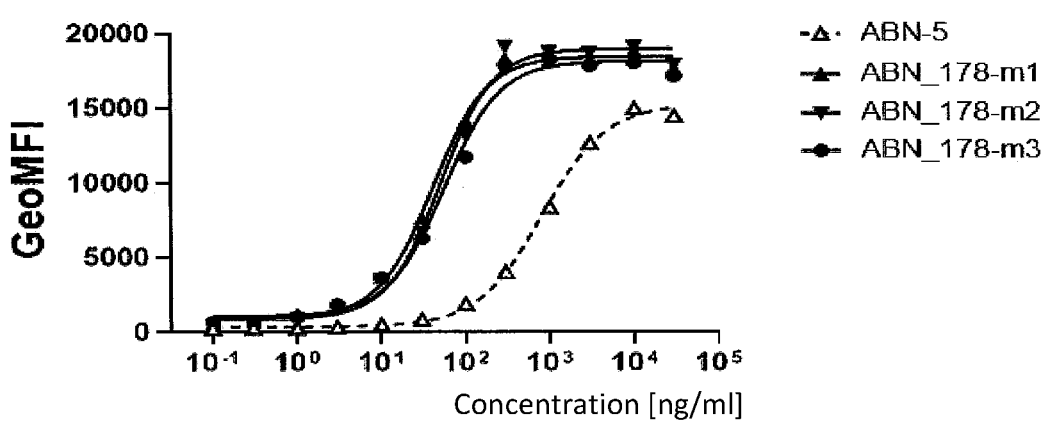
FIG. 3 illustrates binding activity of a humanized one-armed anti-human NR1 antibody to an NMDAR-expressing HEK cell. The vertical axis indicates the geometric mean

The result was consistent that the plurality of humanized one-armed anti-human NR1 antibodies produced in Example 6 had greater binding to NMDAR than the P003-102 antibody. For example, three types of humanized one-armed anti-human NR1 antibodies (ABN_178-m1, ABN_178-m2, ABN_178-m3) derived from mouse antibody ABN_1-178.3 origin had very strong binding to NMDAR compared to ABN-5 (FIG. 3).

The representative humanized one-armed anti-human NR1 antibody was selected from the base mouse anti-human NR1 antibody ABN_1-1-175, ABN 1-1-178.3, ABN_3-385 ABN_1-178.3, and ABN_3-385, and ABN_3-502, which were named as ABN-1, ABN-2 (the same antibody as the above-mentioned ABN_178-m3), ABN-3, and ABN-4, respectively. The amino acid sequence and nucleotide sequence of the VH, VL, heavy chain, light chain, and Fc polypeptide of ABN-5 described in Example 2 and each newly produced humanized one-arm anti-human NR1 antibody are shown in Table 1 (in Table 1, a heavy chain, a light chain, a Fc polypeptide, amino acid sequence and nucleotide sequence are abbreviated to HC, LC, Fc, AA and NA, respectively).

TABLE 1

| | | SEQ ID NO | | | | |
| | | ABN-1 | ABN-2 | ABN-3 | ABN-4 | ABN-5 |
|---|---|---|---|---|---|---|
| VH | AA | 6 | 10 | 14 | 18 | 2 |
| | NA | 5 | 9 | 13 | 17 | 1 |
| VL | AA | 8 | 12 | 16 | 20 | 4 |
| | NA | 7 | 11 | 15 | 19 | 3 |
| HC | AA | 26 | 30 | 34 | 38 | 22 |
| | NA | 25 | 29 | 33 | 37 | 21 |
| LC | AA | 28 | 32 | 36 | 40 | 24 |
| | NA | 27 | 31 | 35 | 39 | 23 |
| FC | AA | 42 | 42 | 42 | 42 | 42 |
| | NA | 41 | 41 | 41 | 41 | 41 |

CDR1, CDR2 and CDR3 of VH shown in SEQ ID NO: 2 consisting of the amino acid sequence of amino acid numbers 26 to 34, 52 to 58 and 97 to 109 of SEQ ID NO: 2 respectively. CDR1, CDR2 and CDR3 of VL shown in SEQ ID NO: 4 consisting of the amino acid sequence of amino acid numbers 26 to 33, 51 to 53 and 92 to 100 of SEQ ID NO: 4 respectively.

CDR1, CDR2 and CDR3 of VH shown in SEQ ID NO: 6 consisting of the amino acid sequence of amino acid numbers 31 to 35, 50 to 66 and 99 to 110 of SEQ ID NO: 6 respectively. CDR1, CDR2 and CDR3 of VL shown in SEQ ID NO: 8 consisting of the amino acid sequence of amino acid numbers 24 to 34, 50 to 56 and 89 to 98 of SEQ ID NO: 8 respectively.

CDR1, CDR2 and CDR3 of VH shown in SEQ ID NO: 10 consisting of the amino acid sequence of amino acid numbers 31 to 35, 50 to 66 and 99 to 111 of SEQ ID NO: 10 respectively.

CDR1, CDR2 and CDR3 of VL shown in SEQ ID NO: 12 consisting of the amino acid sequence of amino acid numbers 24 to 34, 50 to 56 and 89 to 97 of SEQ ID NO: 12 respectively.

CDR1, CDR2 and CDR3 of VH shown in SEQ ID NO: 14 consisting of the amino acid sequence of amino acid numbers 31 to 36, 51 to 66 and 99 to 108 of SEQ ID NO: 14 respectively.

CDR1, CDR2 and CDR3 of VL shown in SEQ ID NO: 16 consisting of the amino acid sequence of amino acid numbers 24 to 34, 50 to 56 and 89 to 97 of SEQ ID NO: 16 respectively.

CDR1, CDR2 and CDR3 of VH shown in SEQ ID NO: 18 consisting of the amino acid sequence of amino acid numbers 31 to 36, 51 to 66 and 99 to 108 of SEQ ID NO: 18 respectively.

CDR1, CDR2 and CDR3 of VL shown in SEQ ID NO: 20 consisting of the amino acid sequence of amino acid numbers 24 to 34, 50 to 56 and 89 to 97 of SEQ ID NO: 20 respectively.

To evaluate the binding activity to the human NMDAR of ABN-2, ABN-4, and ABN-5, Surface Plasmon Resonance (SPR) analysis was performed. Biacore T200 (GE Healthcare) was used for this SPR analysis.

Human Antibody Capture Kit (GE Healthcare, BR-1008-39) was fixed to a CM5 sensor chip (GE Healthcare, BR-1005-30) and Amine Coupling Kit (GE Healthcare, BR-1 000-50) using the Anti-Human IgG (Human Antibody Capture Kit).

Flow channel No. 1 was used as a reference, and no humanized one-armed anti-human NR1 antibody was bound to this flow channel. The humanized anti-human NR1 antibody at the concentration of 2, 5, and 10 μg/mL was prepared in HBS-EP+ buffer (GE Healthcare, BR-1006-69) was added in the other stream (No. 2, No. 3 and No. 4) at a flow rate of 10 μL/min for 50 seconds, respectively, and the antibody is solidified. Then, the human NR1-His protein diluted in the HBS-EP+ buffer to 0.5 μg/mL was added at a flow rate of 50 μL/min for 2 minutes. The binding of a humanized one-armed anti-human NR1 antibody and a humanized NR1-His protein was measured. After adding the HBS-EP+ buffer at a flow rate of 50 μL/min for 5 minutes, the dissociation of a humanized one-armed anti-human NR1 antibody and human NR1-His protein was measured. The dissociation constant (KD) was calculated by analyzing with a 1:1 Binding model, calculating the binding rate constant (ka) and dissociation rate constant (kd), and dividing the kd by the ka. Finally, for the KD value of the humanized one-armed anti-human NR1 antibody, 10 μL/mL of the KD value was used under solid phase conditions of this antibody.

As a result of the SPR analysis, a KD (M) of ABN-2 is 6.92E-10, which has the highest binding activity among ABN-2, ABN-4, and ABN-5] against human NR-His protein. The KD value against the human NRA-His protein of ABN-2, ABN-4, and ABN-5 is shown in Table 2. The KD value of ABN-2 and ABN-4 was much smaller than that of ABN-5's.

TABLE 2

|  | ABN-2 | ABN-4 | ABN-5 |
|---|---|---|---|
| KD(M) | 6.92E–10 | 8.78E–10 | E97E–07 |

Example 8: Competitive Binding Activity of ABN-2, ABN-4, and ABN-5 Against P003-102

Competitive binding activity of ABN-2, ABN-4, and ABN-5 to human NR1 against P003-102 was measured by ELISA competitive assay in a similar manner to Example 5. The result suggest that ABN-2 had stronger antagonistic activity against P003-102 than ABN-4 and ABN-5 in binding to NMDAR. (FIG. 4).

Example 9: Restoration of Cell Surface Expression Levels of NMDAR by Adding ABN-2, ABN-4, and ABN-5

To evaluate the inhibitory effect (inhibition of NMDAR internalization) of ABN-2 and ABN-5 against the internalization of cell surface NMDAR by a pathogenic anti-human NR1 antibody such as P003-102, etc., NMDAR internalization was evaluated using flow cytometry.

The Pathogenic anti-human NR1 antibody mixture used to stimulate NMDAR internalization was prepared at the concentration shown in Table 3 using induction culture media.

TABLE 3

|  | P003-102 | 008-218 | 007-168 |
|---|---|---|---|
| Pathogenic anti-human NR1 antibody mixture (μg/mL) | 0.43 | 0.95 | 4.63 |

The Pathogenic anti-human NR1 antibody mixture was added in 20 μL/well to a 96 well plate (IWAKI, 3860-096). NMDAR-expressing HEK cells were prepared at $2.5 \times 10^6$ cells/mL. in the induction media and seeded at 60 μL/well and cultured overnight under the conditions of 37° C., and 5% $CO_2$. 20 μL/well of serially diluted ABN-2 or ABN-5 was added and incubated overnight, serial dilutions were 3-fold to produce 10 different measurement points. The recovered cells were then treated with ABN-2 in the ABN-2 treatment group, using P003-102 in the ABN-5 treatment group, primary staining each at 5.0 μg/mL for 30 minutes at 4° C. After staining, the cells were sedimented at 1,200 rpm for 5 minute, The supernatant fluid was removed and D-PBS (–) comprising 2% Dialyzed FBS was added to the cells. After adding D-PBS, the cells were centrifuged and the supernatant fluid was removed. Secondary staining was carried out at 4° C. for 30 minutes using a PE-labeled anti-human IgG antibody diluted 100-fold with 2% Dialyzed FBS-comprising D-PBS (–). After staining, the cells were centrifuged and the supernatant fluid was removed as described above. The cells were suspended in 2% Dialyzed FBS-comprising D-PBS (–) and the steps after the secondary staining were repeated. The flow cytometry using FACA Verse was measured as described in Example 3. The NMDAR expression level on the cell surface was analyzed by GeoMFI determining PE fluorescence intensity values using the flow cytometry analysis software FlowJo.

The NMDAR expression level on the cell surface was evaluated as a cell surface NR1 expression rate. The cell surface NR1 expression rate used the PE fluorescence intensity of the NMDAR-expressing HEK cells as an indicator, and calculated the relative values based on the value of 100% when stained with ABN-2 and P003-102 under conditions without pathogenic anti-human NR1 antibody mixture and the value of 0% when stained with isotype control antibody (3G6, an anti-KLH antibody produced in-house).

When ABN-2 and ABN-5 were used, the cell surface NR1 expression rate is shown in FIG. 5. ABN-2 showed a much higher recovery effect than ABN-5 against the pathogenic anti-human NR1 antibody-dependent reduction in cell surface NMDAR expression level. ABN-4 also showed high recovery effect, although less than ABN-2, against the pathogenic anti-human NR1 antibody-dependent reduction in cell surface NMDAR expression levels (data not shown).

Example 10: Evaluation of Recovery of the NMDAR Function by ABN-2 and ABN-4

Cellular calcium concentration was measured to evaluate the effect of ABN-2 and ABN-4 against the hypofunction of NMDAR by the pathogenic antibody P003-102.

100 uL of NMDAR expressing HEK cells were seeded at $1.5 \times 10^5$ cells/well in poly-D lysine-coated 96-well plates (Corning, 356640) in assay media (0.2 mM memantine, 10% FBS comprising NeuroBasal medium). After overnight incubation in the conditions of 37° C. and 5% $CO_2$, 25 uL of P003-102 diluted to a final concentration of 1 μg/mL in the above assay media was added to each well. After incubating for 15 minutes in the conditions of 37° C. and 5% $CO_2$, 25 uL of ABN-2 diluted to final concentration from 10 to 0.01 μg/mL were added to each well. After incubating for 6 hours in the conditions of 37° C. and 5% $CO_2$, the media was removed. 100 ul of FLIPR Calcium 6 Assay Kit (Molecular Device, R8190) of the prepared solution was added to each well and incubated for 2 hours in the conditions of 37° C. and 5% $CO_2$ as described in Example 4. $Ca^{2+}$ influx was measured using FLIPR TETRA. The function of the NMDAR was evaluated using $Ca^{2+}$ influx as an indicator.

The result suggest that ABN-2 had a dose-dependent inhibitory effect on the hypofunction of the NMDAR induced by P003-102 (FIG. 6). The same test was also performed using ABN-4 and ABN-5. ABN-4 showed a weaker inhibitory effect than ABN-2 (the data not shown).

Example 11: Preparing P003-102, and ABN-2 for Testing in Animals

P003-102 and ABN-2 used in Example 12 were prepared.

An expression vector of P003-102 was prepared. For the heavy-chain expression of P003-102, a polynucleotide (SEQ ID NO: 45) encoding a heavy-chain polypeptide (SEQ ID NO: 46) consisting of the heavy-chain variable region sequence of P003-102 (SEQ ID NO: 2), a CH1 sequence, a hinge sequence, and an FC sequence, was connected to the 3' side of a polynucleotide encoding a signal sequence (MEWSWVFLFFLSVTTGVHS; SEQ ID NO: 49), and the connected polynucleotide was inserted into a GS vector pEE6.4 (Lonza). Moreover, for the light-chain expression of P003-102, polynucleotides (SEQ ID NO: 47) encoding a polypeptide (SEQ ID NO: 48) in which a light-chain variable region sequence (SEQ ID NO: 4) and a CL sequence were added to the 3' side of a polynucleotide encoding a signal sequence (MSVPTQVLGLLLLWLTDARC; SEQ ID NO: 50), were connected, and the connected polynucleotides were inserted into a GS vector pEE12.4 (Lonza). The restriction enzyme treatment of these GS vectors was performed with NotI-HF (New England Biolabs, R3189L) and PvuI-HF (New England Biolabs, R3150L). The ligation of those restriction enzyme treatment fragments was performed with DNA Ligation Kit (Ligation-Convenience Kit, NIP-PON GENE, 319-05961). Dual GS vector (DGV) of both genes containing a heavy chain and a light chain was constructed. The transfection of the DGV in CHO-K1SV cells (Lonza) was performed, and a stable cell line express-ing P003-102 was prepared. According to the ordinary method, P003-102 was purified from the culture supernatant of the cells.

For the heavy-chain expression of ABN-2, polynucle-otides (SEQ ID NO: 29) encoding a heavy-chain polypep-tide (SEQ ID NO: 30) in which an FC sequence having the heavy-chain variable region sequence of ABN-2 (SEQ ID NO: 10), a CH1 sequence, a hinge sequence, and a KIH mutation added to the 3' side of a polynucleotide encoding a signal sequence (MEWSWVFLFFLSVTTGVHS; SEQ ID NO: 49), were connected, and the connected polynucleotides were inserted into a GS vector pEE6.4. Moreover, for the light-chain expression of ABN-2, polynucleotides (SEQ ID NO: 31) encoding a polypeptide (SEQ ID NO: 32) in which the light-chain variable region sequence (SEQ ID NO: 12) and a CH1 sequence were added to the 3' side of a poly-nucleotide encoding a signal sequence (MSVPTQVLGLLLLWLTDARC; SEQ ID NO: 50), were inserted into a GS vector pEE12.4. The restriction enzyme treatment of these GS vectors was performed with NotI-HF and PvuI-HF. The ligation of those restriction enzyme treatment fragments was performed with Mighty Mix, and a dual GS vector (DGV) of both genes containing a heavy chain and a light chain was constructed. Moreover, for the expression of an FC polypeptide (SEQ ID NO: 42) to which a KIH mutation paired with a KIH mutation of a heavy-chain polypeptide was added, a polynucleotide (SEQ ID NO: 41) encoding the said FC polypeptide was connected to the 3' side of a polynucleotide encoding a signal sequence (MEWSWVFLFFLSVTTGVHS; SEQ ID NO: 49), and the connected polynucleotide was inserted into a GS vector pEE 12.4. The transfection of two types of expression vectors of pEE12.4 comprising a polynucleotide encoding the DGV and an Fc polypeptide, was performed, and a stable cell line expressing ABN-2 was prepared. According to the ordinary method, ABN-2 was purified from the culture supernatant of the cells Example 12: Preparing an Anti-NMDAR Encephalitic-Like Marmoset Model, and Evaluating the Therapeutic Effect of ABN-2 on the Marmoset Model An anti-NMDAR encephalitic model was prepared with common marmoset (hereinafter referred to as "marmoset"), and the therapeutic effect of ABN-2 was evaluated in the model. The model was prepared by the passive immuniza-tion of P003-102 as described in Example 11. In order to perform the infusion of P003-102, a marmoset was fixed to a brain stereotaxis apparatus (NARISHIGE, SR-6C-HT) with an artificial respirator (SHINANO, SN-480-7) under isoflurane anesthesia (Mylan Inc., 871119). A cannula (Plas-tics One (registered trademark), 813220PSPCLC) was placed at the target within the cerebral ventricles (A/P: 3.5 mm, M/L: ±0.0 mm, Dept: 6.95 mm (from the dura mater)). Regarding the target where the cannula was placed, a marmoset brain map (Stereotaxic Atlas of the Marmoset Brain, NCBI Bookshelf ID:NBK55612) was used as refer-ence. Secondly, a cannula within cerebral ventricles and a micro infusion pump (PRIMETECH, iPRECIO (registered trademark) SMP-200) were connected. The said pump was set at a jacket pocket (in-house) which does not affect the behavior observation. PBS (FUJIFILM Wako Pure Chemi-cal Corporation, 045-29795) was flowed at the flow velocity of 2 µL/hr from a micro infusion pump for a week after the placement of a cannula within the cerebral ventricles. Sub-sequently, the pump was exchanged with a micro infusion pump filled with P003-102 (5,000 µg/mL), and the infusion of P003-102 at the flow velocity of 2 µL/hr (10 g/hr) into the cerebral ventricles. This time point is set as administration day 0. The single treatment of P003-102 had been performed for 14 days. Subsequently, the pump was exchanged with a micro infusion pump filled with the mixture of the equal amount of P003-102 and a therapeutic antibody (ABN-2) (each 2,500 g/mL). The two types of antibodies had been infused at the flow velocity 4 µL/hr (each 10 g/hr) into the cerebral ventricles for 14 days. The treated group of mar-mosets is called "ABN-2 administration group" (n=9). The group of marmosets treated with a control antibody (3G6 which is an in-house anti-KLH antibody) is called "control antibody administration group" (n=3). The following obser-vations were performed.

Method for the Observation of Abnormal Behavior

A video was recorded with a camera at predetermined times for about five minutes, before the administration of P003-102 into cerebral ventricles (day 0), on the fourteenth day (day 14) from the administration of P003-102 had begun, and, on the fourteenth day (day 28) from the admin-istration of ABN-2 or a control antibody together with P003-102.

An abnormal behavior score was evaluated based on the videos with the marmoset version of the abnormal rating scale (Abnormal Rating Scale: ARS) which is an improved Parkinson's disease unified rating scale (UPDRS, Behav Brain Res., 2008, Vol. 194, pp. 152-161). This evaluation was performed by a person experienced in the observation of marmoset behavior under blinded condition. ARS is a scor-ing method with a maximum score of 22 points, using psychological abnormality listings (concentration, motiva-tion, fear/anxiety) and mobility impairment listings (the speed of voluntary movement, the harmony of movement, the presence or absence of jumping, stereotyped behavior, the abnormalities of arms and legs) as evaluation indexes.

The evaluation of abnormal behavior with ARS: it was recognized that the ARS value increased since the admin-istration of P003-102 into the cerebral ventricles of marmo-sets (data not shown). Comparing with day 0, the ARS value (the expression of abnormal behavior) was significantly increased on day 14 (in the center of FIG. 7). In the ABN-2 administration group, a significant decrease of the ARS value was observed on day 28. On the other hand, the control antibody administration group showed a high ARS value even on day 28 (on the right of FIG. 7). Compared with the control antibody administration group, the ABN-2 adminis-tration group showed a significant improvement of abnormal behavior induced by P003-102 (indicated by the decrease of the ARS value). FIG. 8 shows the transition of ARS of each individual marmoset of the ABN-2 administration group on day 0, day 14, and day 28.

A monovalent anti-human NR1 antibody derivative of the invention is expected to be useful for treating anti-NMDAR encephalitis. Moreover, the method of producing a poly-nucleotide, an expression vector, a transformed host cell, and an antibody of the invention is useful for the production of the anti-human NR1 antibody derivative.

Sequence Listing Free Text

In the case of "Artificial Sequence," the description is given in the numerical heading <223> in the following sequence listing. Specifically, the sequence shown in SEQ ID NOS: 1 and 3 in the sequence listing is a codon-optimized nucleotide sequence encoding a heavy chain variable region and a light chain variable region of ABN-5. The nucleotide sequence shown in SEQ ID NOS: 5 and 7 encodes a heavy chain variable region and a light chain variable region of ABN-1. The nucleotide sequence shown in SEQ ID NOS: 9 and 11 in the sequence listing encodes a heavy chain variable region and a light chain variable region of ABN-2. The nucleotide sequence shown in SEQ ID NOS: 13 and 15 in the sequence listing encodes a heavy chain variable region and a light chain variable region of ABN-3. The nucleotide sequence shown in SEQ ID NOS: 17 and 19 in the sequence listing encodes a heavy chain variable region and a light chain variable region of ABN-4. Each amino acid sequence shown in SEQ ID NOS: 6, 8, 10, 12, 14, 16, 18 or 20 is the amino acid sequence of a heavy chain variable region or a light chain variable region encoded by the nucleotide sequence shown in SEQ ID NOS: 5, 7, 9, 11, 13, 15, 17 or 19, respectively. The nucleotide sequence shown in SEQ ID NOS: 21 and 23 encodes a heavy chain and a light chain of ABN-5. The nucleotide sequence shown in SEQ ID NOS: 25 and 27 encodes a heavy chain and a light chain of ABN-1. The nucleotide sequence shown in SEQ ID NOS: 29 and 31 are nucleotide sequences encodes a heavy chain and a light chain of ABN-2. The nucleotide sequence shown in SEQ ID NOS: 33 and 35 encodes a heavy chain and a light chain of ABN-3. The nucleotide sequence shown in SEQ ID NOS: 37 and 39 encodes a heavy chain and a light chain of ABN-4. The amino acid sequence shown in SEQ ID NOS: 22, 24, 26, 28, 30, 32, 34, 36, 38, or 40 are the amino acid sequence of a heavy chain or a light chain encoded by the nucleotide sequence shown in SEQ ID NOS:21, 23, 25, 27, 29, 31, 33, 35, 37 or 39, respectively. The nucleotide sequence shown in SEQ ID NO: 41 encodes a Fc polypeptide of ABN-1-5 and the amino acid sequence shown in a SEQ ID NO: 42 is the amino acid sequence encoded by the nucleotide sequence shown in SEQ ID NO: 41. The nucleotide sequence shown in SEQ ID NO: 43 encodes the extracellular domain of the human NR1 used in the production of human NRA-His protein in Example 5. The amino acid sequence shown in SEQ ID NO: 46 is the amino acid sequence of a heavy chain of P003-102 encoded by the nucleotide sequence shown in SEQ ID NO: 45. The amino acid sequence shown in SEQ ID NO: 48 is the amino acid sequence of a light chain of P003-102 encoded by the nucleotide sequence shown in SEQ ID NO: 47. The amino acid sequence shown in SEQ ID NO: 49 is the signal sequence for expressing P003-12 and a heavy chain of ABN-2, as well as a Fc polypeptide, used in Example 11. The amino acid sequence shown in SEQ ID NO: 50 is a signal sequence for expressing P003-12 and a light chain of ABN-2, used in Example 11.

---

The invention claimed is:

1. An anti-human NR1 antibody comprising an NR1 binding region, the NR1 binding region comprising a heavy chain complementarity determining region 1 (HCDR1), a heavy chain complementarity determining region 2 (HCDR2), a heavy chain complementarity determining region 3 (HCDR3), a light chain complementarity determining region 1 (LCDR1), a light chain complementarity determining region 2 (LCDR2), and a light chain complementarity determining region 3 (LCDR3), selected from:

(1) the HCDR1 consisting of amino acids 31 to 35 of SEQ ID NO: 6, the HCDR2 consisting of amino acids 50 to 66 of SEQ ID NO: 6, the HCDR3 consisting of amino acids 99 to 110 of SEQ ID NO: 6, the LCDR1 consisting of amino acids 24 to 34 of SEQ ID NO: 8, the LCDR2 consisting of amino acids 50 to 56 of SEQ ID NO: 8, and the LCDR3 consisting of amino acid numbers 89 to 98 of SEQ ID NO: 8;

(2) the HCDR1 consisting of amino acids 31 to 36 of SEQ ID NO: 14, the HCDR2 consisting of amino acids 51 to 66 of SEQ ID NO: 14, and the HCDR3 consisting of amino acids of amino acids 99 to 108 of SEQ ID NO: 14, the LCDR1 consisting of amino acids 24 to 34 of SEQ ID NO: 16, the LCDR2 consisting of amino acids 50 to 56 of SEQ ID NO: 16, and the LCDR3 consisting of amino acids 89-97 of SEQ ID NO: 16; or (3) the HCDR1 consisting of amino acids 31 to 36 of SEQ ID NO: 18, the HCDR2 consisting of amino acids 51 to 66 of SEQ ID NO: 18, the HCDR3 consisting of amino acids 99 to 108 of SEQ ID NO: 18, the LCDR1 consisting of amino acids 24 to 34 of SEQ ID NO: 20, the LCDR2 consisting of amino acids 50 to 56 of SEQ ID NO: 20, and the LCDR3 consisting of amino acids 89-97 of SEQ ID NO: 20.

2. The anti-human NR1 antibody according to claim 1, wherein the NR1 binding region comprises a heavy chain variable region and a light chain variable region selected from:

(1) the heavy chain variable region comprises the amino acid sequence set forth in SEQ ID NO: 6 and the light chain variable region comprises the amino acid sequence set forth in SEQ ID NO: 8;

(2) the heavy chain variable region comprises the amino acid sequence set forth in SEQ ID NO: 14 and the light chain variable region comprises the amino acid sequence set forth in SEQ ID NO: 16; or (3) the heavy chain variable region comprises the amino acid sequence set forth in SEQ ID NO: 18 and the light chain variable region comprises the amino acid sequence set forth in SEQ ID NO: 20.

3. The anti-human NR1 antibody according to claim 1, wherein the NR1 binding region comprises a single chain variable region fragment (scFv), Fab fragment, or Fab' fragment.

4. The anti-human NR1 antibody according to claim 1, wherein the NR1 binding region is coupled to an Fc region, wherein the Fc region further comprises L234A and L235A per EU numbering, a Knobs into holes mutation, or both L234A and L235A and a Knobs into holes mutation.

5. The anti-human NR1 antibody according to claim 1, wherein the anti-human NR1 antibody is a humanized antibody.

6. The anti-human NR1 antibody according to claim 1, wherein the NR1 binding region is coupled to an Fc region comprising the amino acid sequence of SEQ ID NO: 42.

7. The anti-human NR1 antibody according to claim 1, wherein the anti-human NR1 antibody inhibits the intracellular internalization of an NMDA receptor by a patient-derived pathogenic anti-human NR1 antibody.

8. A polynucleotide encoding the anti-human NR1 antibody of claim 1.

9. An expression vector comprising the polynucleotide of claim 8.

10. A cell comprising the expression vector of claim 9.

11. A pharmaceutical composition comprising the anti-human NR1 antibody of claim 1 and a pharmaceutically acceptable excipient.

12. A method of treating anti-NMDAR encephalitis in an individual in need thereof, the method comprising administering a therapeutically effective amount of the anti-human NR1 antibody of claim 1 to the individual, thereby treating the anti-NMDAR encephalitis.

13. The anti-human NR1 antibody according to claim 1, wherein the antibody is a monospecific antibody that exhibits monovalent binding to NMDAR.

14. The anti-human NR1 antibody according to claim 1, wherein the antibody is a one-armed anti-human NR1 antibody.

15. The anti-human NR1 antibody according to claim 14, wherein the NR1 binding region comprises a single chain variable region fragment (scFv) or a Fab.

16. A polynucleotide encoding the anti-human NR1 antibody of claim 14.

17. An expression vector comprising the polynucleotide of claim 16.

18. A cell comprising the expression vector of claim 17.

19. A pharmaceutical composition comprising the anti-human NR1 antibody of claim 14 and a pharmaceutically acceptable excipient.

20. A method of treating anti-NMDAR encephalitis in an individual in need thereof, the method comprising administering a therapeutically effective amount of the anti-human NR1 antibody of claim 14 to the individual, thereby treating the anti-NMDAR encephalitis.

* * * * *

```
                        SEQUENCE LISTING

Sequence total quantity: 50
SEQ ID NO: 1              moltype = DNA  length = 360
FEATURE                  Location/Qualifiers
misc_feature             1..360
                         note = codon optimized
source                   1..360
                         mol_type = other DNA
                         organism = synthetic construct
CDS                      1..360
SEQUENCE: 1
caggtccagc tgcaagagtc tggccctgga ctggtcaagc cttctggcac cctgtctctg   60
acatgtgctg tgtccggcgg ctccatctcc tcctctaatt ggtggtcttg ggtccgacag  120
cctcctggca aaggactgga atggatcggc gagatctacc actccggcaa caccaactac  180
aaccccagcc tgaagtccag agtgaccgtg tccgtggaca agtccaagaa ccagttctcc  240
ctgaagctga cctctgtgac cgctgccgat accgccgtgt actactgtgc tagagatgtg  300
tctggcggag tgaattggtt cgatccttgg ggccagggca cactggttac cgtgtcctct  360

SEQ ID NO: 2              moltype = AA  length = 120
FEATURE                  Location/Qualifiers
source                   1..120
                         mol_type = protein
                         organism = Homo sapiens
SEQUENCE: 2
QVQLQESGPG LVKPSGTLSL TCAVSGGSIS SSNWWSWVRQ PPGKGLEWIG EIYHSGNTNY   60
NPSLKSRVTV SVDKSKNQFS LKLTSVTAAD TAVYYCARDV SGGVNWFDPW GQGTLVTVSS  120

SEQ ID NO: 3              moltype = DNA  length = 330
FEATURE                  Location/Qualifiers
misc_feature             1..330
                         note = codon optimized
source                   1..330
                         mol_type = other DNA
                         organism = synthetic construct
CDS                      1..330
SEQUENCE: 3
aactttatgc tgacccagcc tcactccgtg tccgagtctc caggcaagac cgtgaccatc   60
tcctgtacca gatcctccgg ctctatcgcc tccaactacg tgcagtggta tcagcagagg  120
cctggctctg ctcctaccac cgtgatctac gaggacaacc agaggccttc tggcgtgccc  180
gataggttct ctggctccat cgactcctct tccaactccg cctctctgac catcagcggc  240
ctgaaaaccg aggacgaggc cgactactac tgccagtcct acgactcttc caccgtggtg  300
```

-continued

```
tttggcggcg gaacaaagct gacagtgctg                                        330

SEQ ID NO: 4                    moltype = AA   length = 110
FEATURE                         Location/Qualifiers
source                          1..110
                                mol_type = protein
                                organism = Homo sapiens
SEQUENCE: 4
NFMLTQPHSV SESPGKTVTI SCTRSSGSIA SNYVQWYQQR PGSAPTTVIY EDNQRPSGVP        60
DRFSGSIDSS SNSASLTISG LKTEDEADYY CQSYDSSTVV FGGGTKLTVL                   110

SEQ ID NO: 5                    moltype = DNA   length = 363
FEATURE                         Location/Qualifiers
misc_feature                    1..363
                                note = mouse antibody/ humanized
source                          1..363
                                mol_type = other DNA
                                organism = synthetic construct
CDS                             1..363
SEQUENCE: 5
gaagttcagc tggttcagtc tggcgccgaa gtgaagaagc tggcgagtc cctgaagatc         60
tcctgcaaag gctccggcta cacctacacc agctactgga tgaactgggt ccgacagatg       120
cctggcaaag gcctggaatg gatgggcaga atcgaccct acgactccga gacacactac        180
gaccagaaat tcaaggacca agtgaccctg agcgtggaca gtccatctc caccgcttac        240
ctgcagtggt cctctctgaa ggcctctgac accgccatgt actactgtgc tggcggcatc       300
accaccatcc tcggcggcta ctttgattac tggggccagg gcacactggt caccgtttct       360
tcc                                                                     363

SEQ ID NO: 6                    moltype = AA   length = 121
FEATURE                         Location/Qualifiers
REGION                          1..121
                                note = Synthetic Construct
source                          1..121
                                mol_type = protein
                                organism = synthetic construct
SEQUENCE: 6
EVQLVQSGAE VKKPGESLKI SCKGSGYTYT SYWMNWVRQM PGKGLEWMGR IDPYDSETHY        60
DQKFKDQVTL SVDKSISTAY LQWSSLKASD TAMYYCAGGI TTILGGYFDY WGQGTLVTVS       120
S                                                                       121

SEQ ID NO: 7                    moltype = DNA   length = 327
FEATURE                         Location/Qualifiers
misc_feature                    1..327
                                note = mouse antibody/ humanized
source                          1..327
                                mol_type = other DNA
                                organism = synthetic construct
CDS                             1..327
SEQUENCE: 7
gacatccaga tgacccagtc tccatcctct ctgtccgcct ctgtgggcga cagagtgacc        60
atcacctgta gagccagcca ggacatctcc aactacctga actggtatca gcagaagccc       120
ggcaaggccc ctaagctgct gatctactac acctctcggc tgcactctgg cgtgccctct       180
agattttctg gctccggctc tggcaccgac tataccctga caatctccag cctgcagcct       240
gaggacttcg ccacctacta ttgccagcag ggcaacaccc tgcctccata cacatttggc       300
cagggcacca aggtggaaat caagcgt                                           327

SEQ ID NO: 8                    moltype = AA   length = 109
FEATURE                         Location/Qualifiers
REGION                          1..109
                                note = Synthetic Construct
source                          1..109
                                mol_type = protein
                                organism = synthetic construct
SEQUENCE: 8
DIQMTQSPSS LSASVGDRVT ITCRASQDIS NYLNWYQQKP GKAPKLLIYY TSRLHSGVPS        60
RFSGSGSGTD YTLTISSLQP EDFATYYCQQ GNTLPPYTFG QGTKVEIKR                   109

SEQ ID NO: 9                    moltype = DNA   length = 366
FEATURE                         Location/Qualifiers
misc_feature                    1..366
                                note = mouse antibody/ humanized
source                          1..366
                                mol_type = other DNA
                                organism = synthetic construct
CDS                             1..366
SEQUENCE: 9
gaagtgcagc tggttgaatc tggcggcgga ttggttcagc ctggcggatc tctgagactg        60
tcctgcaagg cttctggcta cgcctacacc tcctactgga tgaactgggt ccgacaggct       120
cctggcaaag gactcgtgtg ggtcggaaga atcgacccct acgactccga gacacactac       180
```

-continued

```
aaccagaagt tcaaggaccg gttcaccctg agcgtggaca aggccaagtc taccacctac  240
ctgcagatga actccctgag agccgaggac accgccgtgt actattgcgc taccctgatc  300
accacactga gaggcgaggg cgccatggaa tattggggac agggaaccct ggtcaccgtg  360
tcctct                                                                366

SEQ ID NO: 10               moltype = AA   length = 122
FEATURE                     Location/Qualifiers
REGION                      1..122
                            note = Synthetic Construct
source                      1..122
                            mol_type = protein
                            organism = synthetic construct
SEQUENCE: 10
EVQLVESGGG LVQPGGSLRL SCKASGYAYT SYWMNWVRQA PGKGLVWVGR IDPYDSETHY  60
NQKFKDRFTL SVDKAKSTTY LQMNSLRAED TAVYYCATLI TTLRGEGAME YWGQGTLVTV  120
SS                                                                  122

SEQ ID NO: 11               moltype = DNA   length = 324
FEATURE                     Location/Qualifiers
misc_feature                1..324
                            note = mouse antibody/ humanized
source                      1..324
                            mol_type = other DNA
                            organism = synthetic construct
CDS                         1..324
SEQUENCE: 11
gacctgcaga tgacccagtc tccttccagc ctgtctgcct ctgtgggcga cagagtgacc  60
atcacatgca aggccagcca ggacgtgaac accgccgttg cttggtatca gcagaagcct  120
ggcaaggccc ctaagctgct gatctactgg gcctccacca gacataccgg cgtgccctct  180
agattctccg gctctggctc tggcaccgac tataccctga caatctccag cctgcagcct  240
gaggacttcg ccacctacta ctgccagcag cactacagca ccccttttcac ctttggccag  300
ggcaccaagg tggaaatcaa gcgt                                          324

SEQ ID NO: 12               moltype = AA   length = 108
FEATURE                     Location/Qualifiers
REGION                      1..108
                            note = Synthetic Construct
source                      1..108
                            mol_type = protein
                            organism = synthetic construct
SEQUENCE: 12
DLQMTQSPSS LSASVGDRVT ITCKASQDVN TAVAWYQQKP GKAPKLLIYW ASTRHTGVPS  60
RFSGSGSGTD YTLTISSLQP EDFATYYCQQ HYSTPFTFGQ GTKVEIKR                108

SEQ ID NO: 13               moltype = DNA   length = 357
FEATURE                     Location/Qualifiers
misc_feature                1..357
                            note = mouse antibody/ humanized
source                      1..357
                            mol_type = other DNA
                            organism = synthetic construct
CDS                         1..357
SEQUENCE: 13
caggttcagc tgcaagagtc tggccctggc ctggtcaagc cttccgaaac actgtccctg  60
acctgcagcg tgaccggcta ctctatcacc tccgactact actggcactg gatcagacag  120
cctccaggca aaggcctgga atggatcgcc tacatcagat acgacggccg gaacgactac  180
aaccccagcc tgaagaacag agtgaccatc agccgggaca cctccaagaa ccagttctcc  240
ctgaagctgt cctccgtgac cgctgctgat accgccgtgt actactgcgc cagagaggac  300
tacggctcct cctcctttga ttactggggc cagggcaccc tggtcaccgt tagttct     357

SEQ ID NO: 14               moltype = AA   length = 119
FEATURE                     Location/Qualifiers
REGION                      1..119
                            note = Synthetic Construct
source                      1..119
                            mol_type = protein
                            organism = synthetic construct
SEQUENCE: 14
QVQLQESGPG LVKPSETLSL TCSVTGYSIT SDYYWHWIRQ PPGKGLEWIA YIRYDGRNDY  60
NPSLKNRVTI SRDTSKNQFS LKLSSVTAAD TAVYYCARED YGSSSFDYWG QGTLVTVSS   119

SEQ ID NO: 15               moltype = DNA   length = 324
FEATURE                     Location/Qualifiers
misc_feature                1..324
                            note = mouse antibody/ humanized
source                      1..324
                            mol_type = other DNA
                            organism = synthetic construct
CDS                         1..324
```

```
SEQUENCE: 15
gacatccaga tgacccagtc tccatcctct ctgtccgcct ctgtgggcga cagagtgacc    60
atcacctgtc gggcctccga gaacatctac tccaacctgg cctggtatca gcagaagcct   120
ggcaaggctc ctaagctgct ggtgtacgcc gctaccaatc tggctgatgg cgtgccctct   180
agattctccg gctctggctc tggcaccgac tataccctga caatctccag cctgcagcct   240
gaggacttcg ccacctacta ctgccagcac ttctgggaca gccctccaac ctttggccag   300
ggcaccaagg tggaaatcaa gcgt                                          324

SEQ ID NO: 16          moltype = AA  length = 108
FEATURE                Location/Qualifiers
REGION                 1..108
                       note = Synthetic Construct
source                 1..108
                       mol_type = protein
                       organism = synthetic construct
SEQUENCE: 16
DIQMTQSPSS LSASVGDRVT ITCRASENIY SNLAWYQQKP GKAPKLLVYA ATNLADGVPS    60
RFSGSGSGTD YTLTISSLQP EDFATYYCQH FWDSPPTFGQ GTKVEIKR               108

SEQ ID NO: 17          moltype = DNA  length = 357
FEATURE                Location/Qualifiers
misc_feature           1..357
                       note = mouse antibody/ humanized
source                 1..357
                       mol_type = other DNA
                       organism = synthetic construct
CDS                    1..357
SEQUENCE: 17
caggttcagc tgcaagagtc tggccctggc ctggtcaagc cttctcagac cctgtctctg    60
acctgcagcg tgaccggcta ctccatcacc tccgactact actggcactg gatcagacag   120
cctccaggca aaggcctgga atggatcgc tacatcagat acgacggccg gaacgacagc   180
aaccccagcc tgaagaacag agtgaccatc agccgggaca cctccaagaa ccagttctcc   240
ctgaagctgt cctccgtgac cgctgctgat accgccgtgt actactgcgc cagagaggac   300
tacgcctcct cctcctttga ttactggggc cagggcaccc tggtcaccgt tagttct     357

SEQ ID NO: 18          moltype = AA  length = 119
FEATURE                Location/Qualifiers
REGION                 1..119
                       note = Synthetic Construct
source                 1..119
                       mol_type = protein
                       organism = synthetic construct
SEQUENCE: 18
QVQLQESGPG LVKPSQTLSL TCSVTGYSIT SDYYWHWIRQ PPGKGLEWIA YIRYDGRNDS    60
NPSLKNRVTI SRDTSKNQFS LKLSSVTAAD TAVYYCARED YASSSFDYWG QGTLVTVSS    119

SEQ ID NO: 19          moltype = DNA  length = 324
FEATURE                Location/Qualifiers
misc_feature           1..324
                       note = mouse antibody/ humanized
source                 1..324
                       mol_type = other DNA
                       organism = synthetic construct
CDS                    1..324
SEQUENCE: 19
gacatccaga tgacccagtc tccatcctct ctgtccgcct ctgtgggcga cagagtgacc    60
atcacctgtc ggccttccga gaacatctac tccaacctgg cctggtatca gcagaagcct   120
ggcaaggctc ctaagctgct ggtgtacgcc gctaccaatc tggctgatgg cgtgccctct   180
agattctccg gctctggctc tggcaccgac tataccctga caatctccag cctgcagcct   240
gaggatatcg ccacctacta ctgccagcac ttctgggaca gccctccaac ctttggccag   300
ggcaccaagc tggaaatcaa gcgt                                          324

SEQ ID NO: 20          moltype = AA  length = 108
FEATURE                Location/Qualifiers
REGION                 1..108
                       note = Synthetic Construct
source                 1..108
                       mol_type = protein
                       organism = synthetic construct
SEQUENCE: 20
DIQMTQSPSS LSASVGDRVT ITCRPSENIY SNLAWYQQKP GKAPKLLVYA ATNLADGVPS    60
RFSGSGSGTD YTLTISSLQP EDIATYYCQH FWDSPPTFGQ GTKLEIKR               108

SEQ ID NO: 21          moltype = DNA  length = 1350
FEATURE                Location/Qualifiers
misc_feature           1..1350
                       note = modified antibody
source                 1..1350
                       mol_type = other DNA
```

-continued

```
                       organism = synthetic construct
CDS                    1..1350
SEQUENCE: 21
caggtccagc tgcaagagtc tggccctgga ctggtcaagc cttctggcac cctgtctctg     60
acatgtgctg tgtccggcgg ctccatctcc tcctctaatt ggtggtcttg ggtccgacag    120
cctcctggca aaggactgga atggatcggc gagatctacc actccggcaa caccaactac    180
aaccccagcc tgaagtccag agtgaccgtg tccgtggaca agtccaagaa ccagttctcc    240
ctgaagctga cctctgtgac cgctgccgat accgccgtgt actactgtgc tagagatgtg    300
tctggcggag tgaattggtt cgatccttgg ggccagggca cactggttac cgtgtcctct    360
gcttctacca agggaccctc tgtgttccct ctggctcctt ccagcaagtc tacctctggt    420
ggaaccgctg ctctgggctg cctggtcaag gattactttc ctgagcctgt gacagtgtcc    480
tggaactctg gtgctctgac atccggcgtg cacacctttc cagctgtgct gcagtcctct    540
ggcctgtact ctctgtcctc tgtcgtgacc gtgccttcta gctctctggg cacccagacc    600
tacatctgca acgtgaacca caagccttcc aacaccaagg tggacaagaa ggtggaaccc    660
aagtcctgcg acaagaccca cacctgtcct ccatgtcctg ctccagaagc tgctggcggt    720
ccctccgttt tcctgtttcc acctaagcct aaggacaccc tgatgatctc tcggaccect    780
gaagtgacat gcgtggtggt ggatgtgtcc cacgaggatc ccgaagtgaa gttcaattgg    840
tacgtggacg gcgtggaagt gcacaacgcc aagaccaagc ctagagagga acagtacaac    900
tccacctaca gtgtggtgtc cgtgctgacc gtgctgcacc aggattggct gaacggcaaa    960
gagtacaagt gcaaggtgtc caacaaggcc ctgcctgctc ctatcgaaaa gaccatctcc   1020
aaggctaagg gccagcctcg ggaacctcag gtttacacac tgcctccatc tcgggacgag   1080
ctgaccaaga tcaggtgtc cctgtcttgc gccgtgaagg gcttctaccc ttctgatatc   1140
gccgtggaat gggagtccaa cggccagcct gagaacaact acaagacaac ccctcctgtg   1200
ctggactccg acggctcatt cttcctggtg tccaagctga cagtggataa gtctcggtgg   1260
cagcagggca acgtgttctc ctgttctgtg atgcacgagg ccctgcacaa ccactacacc   1320
cagaagagtc tgtctctgtc ccctggcaag                                    1350

SEQ ID NO: 22        moltype = AA   length = 450
FEATURE              Location/Qualifiers
REGION               1..450
                     note = Synthetic Construct
source               1..450
                     mol_type = protein
                     organism = synthetic construct
SEQUENCE: 22
QVQLQESGPG LVKPSGTLSL TCAVSGGSIS SSNWWSWVRQ PPGKGLEWIG EIYHSGNTNY     60
NPSLKSRVTV SVDKSKNQFS LKLTSVTAAD TAVYYCARDV SGGVNWFDPW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLSC AVKGFYPSDI AVEWESNGQP ENNYKTTPPV LDSDGSFFLV SKLTVDKSRW    420
QQGNVFSCSV MHEALHNHYT QKSLSLSPGK                                     450

SEQ ID NO: 23        moltype = DNA   length = 648
FEATURE              Location/Qualifiers
misc_feature         1..648
                     note = modified antibody
source               1..648
                     mol_type = other DNA
                     organism = synthetic construct
CDS                  1..648
SEQUENCE: 23
aactttatgc tgacccagcc tcactccgtg tccgagtctc caggcaagac cgtgaccatc     60
tcctgtacca gatcctccgg ctctatcgcc tccaactacg tgcagtggta tcagcagagg    120
cctggctctg ctcctaccac cgtgatctac gaggacaacc agaggccttc tggcgtgccc    180
gataggttct ctggctccat cgactcctct tccaactccg cctctctgac catcagcggc    240
ctgaaaaccg aggacgaggc cgactactac tgccagtcct acgactcttc caccgtggtg    300
tttggcggcg gaacaaagct gacagtgctg ggccagcca aggccaatcc taccgtgaca    360
ctgttccctc catcctccga ggaactgcag gctaacaagg ctaccctcgt gtgcctgatc    420
tccgatttt accctggcgc tgtgaccgtg gcttggaagg ctgatggatc tcctgtgaag    480
gccggcgtgg aaaccaccaa gcctagcaag cagtccaaca caaatacgc cgcctcctcc    540
tacctgtctc tgaccctga acagtggaag tcccaccggt cctactcttg ccaagtgacc    600
catgagggca gcaccgtgga aaagacagtg gcccctaccg agtgctct                648

SEQ ID NO: 24        moltype = AA   length = 216
FEATURE              Location/Qualifiers
REGION               1..216
                     note = Synthetic Construct
source               1..216
                     mol_type = protein
                     organism = synthetic construct
SEQUENCE: 24
NFMLTQPHSV SESPGKTVTI SCTRSSGSIA SNYVQWYQQR PGSAPTTVIY EDNQRPSGVP     60
DRFSGSIDSS SNSASLTISG LKTEDEADYY CQSYDSSTVV FGGGTKLTVL GQPKANPTVT    120
LFPPSSEELQ ANKATLVCLI SDFYPGAVTV AWKADGSPVK AGVETTKPSK QSNNKYAASS    180
YLSLTPEQWK SHRSYSCQVT HEGSTVEKTV APTECS                              216

SEQ ID NO: 25        moltype = DNA   length = 1353
```

-continued

```
FEATURE               Location/Qualifiers
misc_feature          1..1353
                      note = mouse antibody/ humanized
source                1..1353
                      mol_type = other DNA
                      organism = synthetic construct
CDS                   1..1353
SEQUENCE: 25
gaagttcagc tggttcagtc tggcgccgaa gtgaagaagc ctggcgagtc cctgaagatc     60
tcctgcaaag gctccggcta cacctacacc agctactgga tgaactgggt ccgacagatg    120
cctggcaaag gcctggaatg gatgggcaga atcgacccct acgactccga gacacactac    180
gaccagaaat tcaaggacca agtgaccctg agcgtggaca agtccatctc caccgcttac    240
ctgcagtggt cctctctgaa ggcctctgac accgccatgt actactgtgc tggcggcatc    300
accaccatcc tcggcggcta ctttgattac tggggccagg gcacactggt caccgtttct    360
tccgctagca ccaagggacc cagcgtgttc cctctggctc cttccagcaa gtctacctct    420
ggcggaacac tgctctgggg ctgcctggtc aaggactact tcctgagcc tgtgaccgtg     480
tcctggaact ctggcgctct gacatctggc gtgcacacct tccagctgt gctgcagtcc     540
tccggcctgt actctctgtc ctctgtcgtg accgtgcctt ccagctctct gggaacccag    600
acctacatct gcaatgtgaa ccacaagcct tccaacacca aggtggacaa gaaggtggaa    660
cccaagtcct gcgacaagac ccacacctgt cctccatgtc ctgctccaga gctgctggc     720
ggaccttccg tgtttctgtt ccctccaaag cctaaggaca ccctgatgat ctctcggacc    780
cctgaagtga cctgcgtggt ggtggatgtg tctcacgagg accagaagt gaagttcaat    840
tggtacgtgg acggcgtgga agtgcacaac gccaagacca gcctagaga ggaacagtac    900
aactccacct acagagtggt gtccgtgctg accgtgctgc accaggattg gctgaacggc    960
aaagagtaca agtgcaaggt gtccaacaag gccctgcctg ctcctatcga aaagaccatc   1020
tccaaggcca agggccagcc tagggaaccc caggtttaca ccttgcctcc atctcgggac   1080
gagctgacca gaaccaggt gtccctgtct tgtgccgtga agggcttcta ccctccgat    1140
atcgctgtgg aatgggagag caatggccag cctgagaaca actacaagac aaccctcct    1200
gtgctggact ccgacggctc attcttcctg gtgtccaagc tgacagtgga taagtccaga   1260
tggcagcagg gcaacgtgtt ctcctgcagc gtgatgcacg aggccctgca caatcactac   1320
acacagaagt ctctgtctct gagccccggc aag                                1353

SEQ ID NO: 26           moltype = AA  length = 451
FEATURE                 Location/Qualifiers
REGION                  1..451
                        note = Synthetic Construct
source                  1..451
                        mol_type = protein
                        organism = synthetic construct
SEQUENCE: 26
EVQLVQSGAE VKKPGESLKI SCKGSGYTYT SYWMNWVRQM PGKGLEWMGR IDPYDSETHY     60
DQKFKDQVTL SVDKSISTAY LQWSSLKASD TAMYYCAGGI TTILGGYFDY WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLS CAVKGFYPSD IAVEWESNGQ PENNYKTTPP VLDSDGSFFL VSKLTVDKSR    420
WQQGNVFSCS VMHEALHNHY TQKSLSLSPG K                                   451

SEQ ID NO: 27           moltype = DNA  length = 645
FEATURE                 Location/Qualifiers
misc_feature            1..645
                        note = mouse antibody/ humanized
source                  1..645
                        mol_type = other DNA
                        organism = synthetic construct
CDS                     1..645
SEQUENCE: 27
gacatccaga tgacccagtc tccatcctct ctgtccgcct ctgtgggcga cagagtgacc     60
atcacctgta gagccagcca ggacatctcc aactacctga actggtatca gcagaagccc    120
ggcaaggccc ctaagctgct gatctactac acctctcggc tgcactctgg cgtgccctct    180
agatttctg gctccggctc tggcaccgac tataccctga caatctccag cctgcagcct    240
gaggacttcg ccacctacta ttgccagcag ggcaacaccc tgcctccata cacatttggc    300
cagggcacca aggtggaaat caagcgtacg gtggccgctc cttccgtgtt catcttccca    360
ccttccgacg agcagctgaa gtccggcaca gcttctgtcg tgtgcctgct gaacaacttc    420
taccctcggg aagccaaggt gcagtggaag gtggacaatg ccctgcagtc cggcaactcc    480
caagagtctg tgaccgagca ggactccaag gacagcacct acagcctgtc ctccacactg    540
accctgtcca aggccgacta cgagaagcac aaggtgtacg cctgcgaagt gacccatcag    600
ggcctgtcta gccctgtgac caagtctttc aaccggggcg agtgc                    645

SEQ ID NO: 28           moltype = AA  length = 215
FEATURE                 Location/Qualifiers
REGION                  1..215
                        note = Synthetic Construct
source                  1..215
                        mol_type = protein
                        organism = synthetic construct
SEQUENCE: 28
DIQMTQSPSS LSASVGDRVT ITCRASQDIS NYLNWYQQKP GKAPKLLIYY TSRLHSGVPS     60
```

```
RFSGSGSGTD YTLTISSLQP EDFATYYCQQ GNTLPPYTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 29           moltype = DNA  length = 1356
FEATURE                 Location/Qualifiers
misc_feature            1..1356
                        note = mouse antibody/ humanized
source                  1..1356
                        mol_type = other DNA
                        organism = synthetic construct
CDS                     1..1356
SEQUENCE: 29
gaagtgcagc tggttgaatc tggcggcgga ttggttcagc ctggcggatc tctgagactg   60
tcctgcaagg cttctggcta cgcctacacc tcctactgga tgaactgggt ccgacaggct   120
cctggcaaag gactcgtgtg ggtcggaaga atcgacccct acgactccga gacacactac   180
aaccagaagt tcaaggaccg gttcaccctg agcgtggaca aggccaagtc taccacctac   240
ctgcagatga actccctgag agccgaggac accgccgtgt actattgcgc taccctgatc   300
accacactga gaggcgaggg cgccatggaa tattgggggac agggaaccct ggtcaccgtg   360
tcctctgcta gcaccaaggg accctctgtg ttccctctgg ctccttccag caagtccacc   420
tctggtggaa cagctgctct gggctgcctg gtcaaggact actttcctga gcctgtgacc   480
gtgtcttgga actctggcgc tctgacatct ggcgtgcaca cctttccagc tgtgctgcag   540
tcctccggcc tgtactctct gtcctctgtc gtgaccgtgc cttccagctc tctgggaacc   600
cagacctaca tctgcaatgt gaaccacaag ccttccaaca ccaaggtcga caagaaggtg   660
gaacccaagt cctgcgacaa gacccacacc tgtcctccat gtcctgctcc agaagctgct   720
ggcggccctt ccgtgtttct gttccctcca aagcctaagg acaccctgat gatctctcgg   780
acccctgaag tgacctgcgt ggtggtggat gtgtctcacg aggatcccga agtgaagttc   840
aattggtacg tggacggcgt ggaagtgcac aacgccaaga ccaagcctag agaggaacag   900
tacaactcca cctacagagt ggtgtccgtg ctgaccgtgc tgcaccagga ttggctgaac   960
ggcaaagagt acaagtgcaa ggtgtccaac aaggccctgc ctgctcctat cgaaaagacc   1020
atctctaagg ccaagggcca gcctcgggaa cctcaggttt acaccttgcc tccatctcgg   1080
gacgagctga ccaagaacca ggtgtccctg tcttgtgccg tgaagggctt ctaccctcc   1140
gatatcgctg tggaatggga gagcaatggc cagcctgaga caactacaa gacaacccct   1200
cctgtgctgg actccgacgg ctcattcttc ctggtgtcca agctgacagt ggacaagtcc   1260
agatggcagc agggcaacgt gttctcctgc agcgtgatgc acgaggccct gcacaatcac   1320
tacccagaga gtctctgtc tctgagcccc ggcaag                            1356

SEQ ID NO: 30           moltype = AA  length = 452
FEATURE                 Location/Qualifiers
REGION                  1..452
                        note = Synthetic Construct
source                  1..452
                        mol_type = protein
                        organism = synthetic construct
SEQUENCE: 30
EVQLVESGGG LVQPGGSLRL SCKASGYAYT SYWMNWVRQA PGKGLVWVGR IDPYDSETHY   60
NQKFKDRFTL SVDKAKSTTY LQMNSLRAED TAVYYCATLI TTLRGEGAME YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL SCAVKGFYPS DIAVEWESNG QPENNYKTTP PVLDSDGSFF LVSKLTVDKS   420
RWQQGNVFSC SVMHEALHNH YTQKSLSLSP GK                                452

SEQ ID NO: 31           moltype = DNA  length = 642
FEATURE                 Location/Qualifiers
misc_feature            1..642
                        note = mouse antibody/ humanized
source                  1..642
                        mol_type = other DNA
                        organism = synthetic construct
CDS                     1..642
SEQUENCE: 31
gacctgcaga tgacccagtc tccttccagc ctgtctgcct ctgtgggcga cagagtgacc   60
atcacatgca aggccagcca ggacgtgaac accgccgttg cttggtatca gcagaagcct   120
ggcaaggccc ctaagctgct gatctactgg gcctccacca gacataccgg cgtgccctct   180
agattctccg gctctggctc tggcaccgac tatacc..tga caatctccag cctgcagcct   240
gaggacttcg ccacctacta ctgccagcag cactacagca cccctttcac ctttggccag   300
ggcaccaagg tggaaatcaa gcgtacggtg gccgctcctt ccgtgttcat cttcccacct   360
tccgacgagc agctgaagtc cggcacagct tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctata gcctgtcctc cacactgacc   540
ctgtccaagg ccgactacga gaagcacaag gtgtacgcct gcgaagtgac ccatcagggc   600
tgtctagtc cgtgaccaa gtctttcaac cggggcgagt gc                     642

SEQ ID NO: 32           moltype = AA  length = 214
FEATURE                 Location/Qualifiers
REGION                  1..214
                        note = Synthetic Construct
```

-continued

```
source                    1..214
                          mol_type = protein
                          organism = synthetic construct
SEQUENCE: 32
DLQMTQSPSS LSASVGDRVT ITCKASQDVN TAVAWYQQKP GKAPKLLIYW ASTRHTGVPS   60
RFSGSGSGTD YTLTISSLQP EDFATYYCQQ HYSTPFTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 33              moltype = DNA   length = 1347
FEATURE                   Location/Qualifiers
misc_feature              1..1347
                          note = mouse antibody/ humanized
source                    1..1347
                          mol_type = other DNA
                          organism = synthetic construct
CDS                       1..1347
SEQUENCE: 33
caggttcagc tgcaagagtc tggccctggc ctggtcaagc cttccgaaac actgtccctg   60
acctgcagcg tgaccggcta ctctatcacc tccgactact actggcactg gatcagacag  120
cctccaggca aaggcctgga atggatcgcc tacatcagat acgacggccg gaacgactac  180
aaccccagcc tgaagaacag agtgaccatc agccggacca cctccaagaa ccagttctcc  240
ctgaagctgt cctccgtgac cgctgctgat accgccgtgt actactgcgc cagagaggac  300
tacggctcct cctcctttga ttactggggc cagggcaccc tggtcaccgt tagttctgct  360
agcaccaagg gacccagcgt gttccctctg gctccttcca gcaagtctac ctctggcgga  420
acagctgctc tgggctgtct ggtcaaggac tacttccctg agcctgtgac cgtgtcctgg  480
aactctggcg ctctgacatc tggcgtgcac accttccag ctgtgctgca gtcctccggc  540
ctgtactctc tgtcctctgt cgtgaccgtg ccttccagct ctctgggaac ccagacctac  600
atctgcaatg tgaaccacaa gcctagcaac accaaggtgg acaagaaggt ggaacccaag  660
tcctgcgaca gacccacac ctgtcctcca tgtcctgctc cagaagctgc tggcggccct  720
tccgtgtttc tgttccctcc aaagcctaag gacaccctga tgatctctcg gacccctgaa  780
gtgacctgcg tggtggtgga tgtgtctcac gaggatcccg aagtgaagtt caattggtac  840
gtggacggcg tggaagtgca caacgccaag accaagccta gagaggaaca gtacaactcc  900
acctacagag tggtgtccgt gctgaccgtg ctgcaccagg attggctgaa cggcaaagag  960
tacaagtgca aggtgtccaa caaggccctg cctgctccta tcgaaaagac catctccaag 1020
gctaagggcc agcctcggga acctcaggtg tacacattgc ctccatctcg ggacgagctg 1080
accaagaatc aggtgtccct gtcttgcgcc gtgaagggct ctacccttc cgatatcgcc 1140
gtggaatggg agtccaatgg ccagccagag aacaactaca agacaacccc tcctgtgctg 1200
gactccgacg gctcattctt cctggtgtcc aagctgacag tggacaagtc cagatggcag 1260
cagggcaacg tgttctcctg ctctgtgatg cacgaggccc tgcacaacca ctacacccag 1320
aagtctctgt ctctgagccc cggcaag                                     1347

SEQ ID NO: 34              moltype = AA   length = 449
FEATURE                   Location/Qualifiers
REGION                    1..449
                          note = Synthetic Construct
source                    1..449
                          mol_type = protein
                          organism = synthetic construct
SEQUENCE: 34
QVQLQESGPG LVKPSETLSL TCSVTGYSIT SDYYWHWIRQ PPGKGLEWIA YIRYDGRNDY   60
NPSLKNRVTI SRDTSKNQFS LKLSSVTAAD TAVYYCARED YGSSSFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                    449

SEQ ID NO: 35              moltype = DNA   length = 642
FEATURE                   Location/Qualifiers
misc_feature              1..642
                          note = mouse antibody/ humanized
source                    1..642
                          mol_type = other DNA
                          organism = synthetic construct
CDS                       1..642
SEQUENCE: 35
gacatccaga tgacccagtc tccatcctct ctgtccgcct ctgtgggcga cagagtgacc   60
atcacctgtc gggcctccga gaacatctac tccaacctgg cctggtatca gcagaagcct  120
ggcaaggctc ctaagctgct ggtgtacgcc gctaccaatc tggctgatgg cgtgccctct  180
agattctccg gctctggctc tggcaccgac tataccctga caatctccag cctgcagcct  240
gaggacttcg ccacctacta ctgccagcac ttctgggaca gccctccaac ctttggccag  300
ggcaccaagg tggaaatcaa gcgtacggtg gccgctcctt ccgtgttcat cttcccacct  360
tccgacgagc agctgaagtc cggcacagct tctgtcgtgt gcctgctgaa caacttctac  420
cctcgggaag ccaaggtgca gtggaaggtg gacaatgccc tgcagtccgg caactcccaa  480
gagtctgtga ccgagcagga ctccaaggac agcacctaca gcctgtcctc cacactgacc  540
ctgtccaagg ccgactacga gaagcacaag gtgtacgctt gcgaagtgac ccaccagggc  600
ctgtctagcc ctgtgaccaa gtccttcaac cggggcgagt gc                    642
```

-continued

```
SEQ ID NO: 36            moltype = AA   length = 214
FEATURE                  Location/Qualifiers
REGION                   1..214
                         note = Synthetic Construct
source                   1..214
                         mol_type = protein
                         organism = synthetic construct
SEQUENCE: 36
DIQMTQSPSS LSASVGDRVT ITCRASENIY SNLAWYQQKP GKAPKLLVYA ATNLADGVPS   60
RFSGSGSGTD YTLTISSLQP EDFATYYCQH FWDSPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 37            moltype = DNA   length = 1347
FEATURE                  Location/Qualifiers
misc_feature             1..1347
                         note = mouse antibody/ humanized
source                   1..1347
                         mol_type = other DNA
                         organism = synthetic construct
CDS                      1..1347
SEQUENCE: 37
caggttcagc tgcaagagtc tggccctggc ctggtcaagc cttctcagac cctgtctctg   60
acctgcagcg tgaccggcta ctccatcacc tccgactact actggcactg gatcagacag  120
cctccaggca aaggcctgga atggatcgcc tacatcgtat acgacggccg gaacgacagc  180
aaccccagcc tgaagaacag agtgaccatc agccgggaca cctccaagaa ccagttctcc  240
ctgaagctgt cctccgtgac cgctgctgat accgccgtgt actactgcgc cagagaggac  300
tacgcctcct cctcctttga ttactggggc cagggcaccc tggtcaccgt tagttctgct  360
agcaccaagg gacccagcgt gttccctctg gctccttcca gcaagtctac ctctggcgga  420
acagctgctc tgggctgtct ggtcaaggac tacttccctg agcctgtgac cgtgtcctgg  480
aactctggcg ctctgacatc tggcgtgcac acctttccag ctgtgctgca gtcctccggc  540
ctgtactctc tgtcctctgt cgtgaccgtg ccttccagct ctctgggaac ccagacctac  600
atctgcaatg tgaaccacaa gccttccaac accaaggtgg acaagaaggt ggaacccaag  660
tcctgcgaca gaccccacac ctgtcctcca tgtcctgctc cagaagctgc tggcggccct  720
tccgtgtttc tgttccctcc aaagcctaag gacaccctga tgatctctcg gacccctgaa  780
gtgacctgcg tggtggtgga tgtgtctcac gaggatcccg aagtgaagtt caattggtac  840
gtggacggcg tggaagtgca caacgccaag accaagccta gagaggaaca gtacaactcc  900
acctacagag tggtgtccgt gctgaccgtg ctgcaccagg attggctgaa cggcaaagag  960
tacaagtgca aggtgtccaa caaggccctg cctgctccta tcgaaaagac catctccaag  1020
gctaagggcc agcctcggga acctcaggtg tacacattgc ctccatctcg ggacgagctg  1080
accaagaatc aggtgtccct gtcctgtgcc gtgaagggct ctacccttc cgatatcgcc  1140
gtggaatggg agtccaatgg ccagccagag aacaactaca agacaacccc tcctgtgctg  1200
gactccgacg gctcattctt cctggtgtcc aagctgacag tggacaagtc cagatggcag  1260
cagggcaacg tgttctcctg ctctgtgatg cacgaggccc tgcacaacca ctacacccag  1320
aagagtctgt ctctgtcccc tggcaag                                     1347

SEQ ID NO: 38            moltype = AA   length = 449
FEATURE                  Location/Qualifiers
REGION                   1..449
                         note = Synthetic Construct
source                   1..449
                         mol_type = protein
                         organism = synthetic construct
SEQUENCE: 38
QVQLQESGPG LVKPSQTLSL TCSVTGYSIT SDYYWHWIRQ PPGKGLEWIA YIRYDGRNDS   60
NPSLKNRVTI SRDTSKNQFS LKLSSVTAAD TAVYYCARED YASSSFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGK                                    449

SEQ ID NO: 39            moltype = DNA   length = 642
FEATURE                  Location/Qualifiers
misc_feature             1..642
                         note = mouse antibody/ humanized
source                   1..642
                         mol_type = other DNA
                         organism = synthetic construct
CDS                      1..642
SEQUENCE: 39
gacatccaga tgacccagtc tccatcctct ctgtccgcct ctgtgggcga cagagtgacc   60
atcacctgtc ggccttccga gaacatctac tccaacctgg cctggtatca gcagaagcct  120
ggcaaggctc ctaagctgct ggtgtacgcc gctaccaatc tggctgatgg cgtgccctct  180
agattctccg gctctggctc tggcaccgac tataccctga caatctccag cctgcagcct  240
gaggatatcc ccacctacta ctgccagcac ttctgggaca ccctccaac ctttggccag  300
ggcaccaagc tggaaatcaa gcgtacggtg gccgctcctt ccgtgttcat cttcccacct  360
```

-continued

```
tccgacgagc agctgaagtc cggcacagct tctgtcgtgt gcctgctgaa caacttctac  420
cctcgggaag ccaaggtgca gtggaaggtg gacaatgccc tgcagtccgg caactcccaa  480
gagtctgtga ccgagcagga ctccaaggac agcacctaca gcctgtcctc cacactgacc  540
ctgtccaagg ccgactacga gaagcacaag gtgtacgctt gcgaagtgac ccaccagggc  600
ctgtctagcc ctgtgaccaa gtccttcaac cggggcgagt gc                     642

SEQ ID NO: 40             moltype = AA   length = 214
FEATURE                   Location/Qualifiers
REGION                    1..214
                          note = Synthetic Construct
source                    1..214
                          mol_type = protein
                          organism = synthetic construct
SEQUENCE: 40
DIQMTQSPSS LSASVGDRVT ITCRPSENIY SNLAWYQQKP GKAPKLLVYA ATNLADGVPS  60
RFSGSGSGTD YTLTISSLQP EDIATYYCQH FWDSPPTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 41             moltype = DNA   length = 666
FEATURE                   Location/Qualifiers
misc_feature              1..666
                          note = modified Fc fragment
source                    1..666
                          mol_type = other DNA
                          organism = synthetic construct
CDS                       1..666
SEQUENCE: 41
tgccctccat gtcctgctcc agaagccgct ggcggaccct ctgtgtttct gttccctcca  60
aagcctaagg acaccctgat gatctctcgg acccctgaag tgacctgcgt ggtggtggat  120
gtgtctcacg aggatcccga agtgaagttc aattggtacg tggacggcgt ggaagtgcac  180
aacgccaaga ccaagcctag agaggaacag tacaactcca cctacagagt ggtgtccgtg  240
ctgaccgtgc tgcaccagga ttggctgaac ggcaaagagt acaagtgcaa ggtgtccaac  300
aaggccctgc ctgctcctat cgaaaagacc atctccaagg ctaagggcca gcctcgggaa  360
cctcaggttt acacactgcc tccatctcgg gacgagctga ccaagaatca ggtgtccctg  420
tggtgcctgg tcaagggctt ctaccttcc gatatcgccg tggaatggga gtccaatggc  480
cagcctgaga caactacaa gaccacacct cctgtgctgg actccgacgg ctcattcttc  540
ctgtactcca agctgacagt ggacaagtct cggtggcagc agggcaacgt gttctcctgt  600
tctgtgatgc acgaggccct gcacaaccac tacacccaga agtccctgtc tctgtcccct  660
ggcaaa                                                            666

SEQ ID NO: 42             moltype = AA   length = 222
FEATURE                   Location/Qualifiers
REGION                    1..222
                          note = Synthetic Construct
source                    1..222
                          mol_type = protein
                          organism = synthetic construct
SEQUENCE: 42
CPPCPAPEAA GGPSVFLFPP KPKDTLMISR TPEVTCVVVD VSHEDPEVKF NWYVDGVEVH  60
NAKTKPREEQ YNSTYRVVSV LTVLHQDWLN GKEYKCKVSN KALPAPIEKT ISKAKGQPRE  120
PQVYTLPPSR DELTKNQVSL WCLVKGFYPS DIAVEWESNG QPENNYKTTP PVLDSDGSFF  180
LYSKLTVDKS RWQQGNVFSC SVMHEALHNH YTQKSLSLSP GK                     222

SEQ ID NO: 43             moltype = DNA   length = 1176
FEATURE                   Location/Qualifiers
misc_feature              1..1176
                          note = codon optimized
source                    1..1176
                          mol_type = other DNA
                          organism = synthetic construct
CDS                       1..1176
SEQUENCE: 43
atggtcaacga tgaggctcct gaccccttgct ctgctgttca gctgctcagt tgccagggct  60
gcttgtgacc ccaaaatcgt gaacattggc gccgtgctgt ctaccagaaa gcacgagcag  120
atgtttaggg aagccgtgaa ccaggcaaac aagaggcatg ggtcttggaa aattcagctg  180
aatgcaacct ctgtgacaca caagccaaat gccattcaaa tggcactgtc cgtctgcgag  240
gacttgatta gcagccaggt ttacgccata ctcgtgagcc atcctcccac gcccaatgac  300
cacttcactc caactcctgt ttcctatacc gctggctttt accggattcc tgtcttgggc  360
ctcaccacaa gaatgagtat ctacagtgac aagagcatac acctgagttt cctccgcact  420
gtgcctccct atagtcacca gtcctctgtg tggttcgaaa tgatgagggt ctactcctgg  480
aatcacatca ttctgttggt gtccgatgac acgaaggac gtgcagccca gaaaaggctg  540
gaaactctgc tcgaagaacg agagtcaaaa gcggaaaagg tgctgcaatt cgacccagga  600
acaaagaacg tcactgcgtt gctgatggag gcaaaagagc tggaagcacg ggtgatcatc  660
ctcagcgcat cagaggacga tgccgccact gtgtatcgag ctgctgcgat gctgaatatg  720
acagggtccg gctacgtctg gcttgtcggc gagagagaga ttagcggtaa tgctctgcgg  780
tatgctcccg atggcatctt ggggcttcag ctcatcaatg gcaagaacga aagcgcccat  840
atttctgacg ccgttggggt agtagcccaa gcagttcacg agctgcttga aaggagaac  900
ataaccgatc cacctagagg gtgtgtgggg aacaccaaca tttggaaaac aggaccgctg  960
```

```
ttcaaacgag ttctgatgtc tagcaagtat gctgatggcg tgacaggcag agtggagttc  1020
aacgaggatg gtgatcggaa atttgctaac tacagcatta tgaatctgca aaatcgcaaa  1080
ctggtacagg ttgggatata caatggaacc cacgtgatcc cgaacgaccg gaagataatc  1140
tggcctggag gcgaaacgga gaaaccccgc ggttat                            1176

SEQ ID NO: 44          moltype = AA   length = 392
FEATURE                Location/Qualifiers
source                 1..392
                       mol_type = protein
                       organism = Homo sapiens
SEQUENCE: 44
MSTMRLLTLA LLFSCSVARA ACDPKIVNIG AVLSTRKHEQ MFREAVNQAN KRHGSWKIQL   60
NATSVTHKPN AIQMALSVCE DLISSQVYAI LVSHPPTPND HFTPTPVSYT AGFYRIPVLG  120
LTTRMSIYSD KSIHLSFLRT VPPYSHQSSV WFEMMRVYSW NHIILLVSDD HEGRAAQKRL  180
ETLLEERESK AEKVLQFDPG TKNVTALLME AKELEARVII LSASEDDAAT VYRAAAMLNM  240
TGSGYVWLVG EREISGNALR YAPDGILGLQ LINGKNESAH ISDAVGVVAQ AVHELLEKEN  300
ITDPPRGCVG NTNIWKTGPL FKRVLMSSKY ADGVTGRVEF NEDGDRKFAN YSIMNLQNRK  360
LVQVGIYNGT HVIPNDRKII WPGGETEKPR GY                               392

SEQ ID NO: 45          moltype = DNA   length = 1350
FEATURE                Location/Qualifiers
misc_feature           1..1350
                       note = pathogenic anti-human NR1 antibody
source                 1..1350
                       mol_type = other DNA
                       organism = synthetic construct
CDS                    1..1350
SEQUENCE: 45
caggtccagc tgcaagagtc tggccctgga ctggtcaagc cttctggcac cctgtctctg   60
acatgtgctg tgtccggcgg ctccatctcc tcctctaatt ggtggtcttg ggtccgacag  120
cctcctggca aaggactgga atggatcggc gagatctacc actccggcaa caccaactac  180
aaccccagcc tgaagtccag agtgaccgtg tccgtggaca agtccaagaa ccagttctcc  240
ctgaagctga cctctgtgac cgctgccgat accgccgtgt actactgtgc tagagatgtg  300
tctggcggag tgaattggtt cgatccttgg ggccagggca cactggttac cgtgtcctct  360
gcttctacca agggaccctc tgtgttccct ctggctcctt ccagcaagtc tacctctggt  420
ggaaccgctg ctctgggctg cctggtcaag gattactttc ctgagcctgt gacagtgtcc  480
tggaactctg gtgctctgac atccggcgtg cacacctttc cagctgtgct gcagtcctct  540
ggcctgtact ctctgtcctc tgtcgtgacc gtgccttcta gctctctggg cacccagacc  600
tacatctgca acgtgaacca caagccttcc aacaccaagg tggacaagaa ggtggaaccc  660
aagtcctgcg acaagaccca cacctgtcct ccatgtcctg ctccagaact gctcggcggt  720
ccctccgttt cctgtttcc acctaagcct aaggacaccc tgatgatctc tcggacccct  780
gaagtgacat gcgtggtggt ggatgtgtcc cacgaggatc ccgaagtgaa gttcaattgg  840
tacgtggacg gcgtggaagt gcacaacgcc aagaccaagc ctagagagga acagtacaac  900
tccacctaca gtggtgtgtc cgtgctgacc gtgctgcacc aggattggct gaacggcaaa  960
gagtacaagt gcaaggtgtc caacaaggcc ctgcctgctc ctatcgaaaa gaccatctcc  1020
aaggctaagg gccagcctcg ggaacctcag gtttacacac tgcctccatc tcgggacgag  1080
ctgaccaaga atcaggtgtc cctgacctgc ctcgtgaagg gcttctaccc ttctgatatc  1140
gccgtggaat gggagtccaa cggccagcct gagaacaact acaagacaac ccctcctgtg  1200
ctggactccg acggctcatt cttcctgtac tccaagctga cagtggataa gtcccggtgg  1260
cagcagggca cgtgttctc ttgttctgtg atgcacgagg ccctgcacaa ccactacacc  1320
cagaagagtc tgtctctgtc ccctggcaag                                  1350

SEQ ID NO: 46          moltype = AA   length = 450
FEATURE                Location/Qualifiers
REGION                 1..450
                       note = Synthetic Construct
source                 1..450
                       mol_type = protein
                       organism = synthetic construct
SEQUENCE: 46
QVQLQESGPG LVKPSGTLSL TCAVSGGSIS SSNWWSWVRQ PPGKGLEWIG EIYHSGNTNY   60
NPSLKSRVTV SVDKSKNQFS LKLTSVTAAD TAVYYCARDV SGGVNWFDPW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 47          moltype = DNA   length = 648
FEATURE                Location/Qualifiers
misc_feature           1..648
                       note = Pathogenic anti-human NR1 antibody
source                 1..648
                       mol_type = other DNA
                       organism = synthetic construct
CDS                    1..648
SEQUENCE: 47
aactttatgc tgacccagcc tcactccgtg tccgagtctc caggcaagac cgtgaccatc   60
```

-continued

```
tcctgtacca gatcctccgg ctctatcgcc tccaactacg tgcagtggta tcagcagagg   120
cctggctctg ctcctaccac cgtgatctac gaggacaacc agaggccttc tggcgtgccc   180
gataggttct ctggctccat cgactcctct tccaactccg cctctctgac catcagcggc   240
ctgaaaaccg aggacgaggc cgactactac tgccagtcct acgactcttc caccgtggtg   300
tttggcggcg gaacaaagct gacagtgctg ggccagccta aggccaatcc taccgtgaca   360
ctgttccctc catcctccga ggaactgcag gctaacaagg ctaccctcgt gtgcctgatc   420
tccgattttt accctggcgc tgtgaccgtg gcttggaagg ctgatggatc tcctgtgaag   480
gccggcgtgg aaaccaccaa gcctagcaag cagtccaaca acaaatacgc cgcctcctcc   540
tacctgtctc tgacccctga acagtggaag tcccaccggt cctactcttg ccaagtgacc   600
catgagggca gcaccgtgga aaagacagtg gcccctaccg agtgctct              648
```

```
SEQ ID NO: 48          moltype = AA  length = 216
FEATURE                Location/Qualifiers
REGION                 1..216
                       note = Synthetic Construct
source                 1..216
                       mol_type = protein
                       organism = synthetic construct
SEQUENCE: 48
NFMLTQPHSV SESPGKTVTI SCTRSSGSIA SNYVQWYQQR PGSAPTTVIY EDNQRPSGVP    60
DRFSGSIDSS SNSASLTISG LKTEDEADYY CQSYDSSTVV FGGGTKLTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                            216
```

```
SEQ ID NO: 49          moltype = AA  length = 19
FEATURE                Location/Qualifiers
REGION                 1..19
                       note = Synthetic Construct
source                 1..19
                       mol_type = protein
                       organism = synthetic construct
SEQUENCE: 49
MEWSWVFLFF LSVTTGVHS                                                19
```

```
SEQ ID NO: 50          moltype = AA  length = 20
FEATURE                Location/Qualifiers
REGION                 1..20
                       note = Synthetic Construct
source                 1..20
                       mol_type = protein
                       organism = synthetic construct
SEQUENCE: 50
MSVPTQVLGL LLLWLTDARC                                               20
```